United States Patent [19]

Kramer et al.

[11] Patent Number: 5,250,524
[45] Date of Patent: Oct. 5, 1993

[54] BILE ACID DERIVATIVES, PROCESS FOR THEIR PREPARATION AND USE OF THESE COMPOUNDS AS PHARMACEUTICALS

[75] Inventors: Werner Kramer, Mainz; Günther Wess, Erlensee; Stefan Müllner, Hochheim; Horst Neubauer, Königstein/Taunus, all of Fed. Rep. of Germany

[73] Assignee: Hoechst Aktiengesellschaft, Frankfurt am Main, Fed. Rep. of Germany

[21] Appl. No.: 802,413

[22] Filed: Dec. 4, 1991

[30] Foreign Application Priority Data

Dec. 6, 1990 [DE] Fed. Rep. of Germany ....... 4038833

[51] Int. Cl.$^5$ .................. A61K 31/56; C07J 53/00
[52] U.S. Cl. .................. 514/177; 514/179; 514/182; 552/509
[58] Field of Search ............. 552/509; 514/182, 179, 514/177

[56] References Cited

U.S. PATENT DOCUMENTS 4,418,059 11/1983 Lalezari .............................. 552/509

FOREIGN PATENT DOCUMENTS 0092073 10/1983 European Pat. Off. .
0202703 11/1986 European Pat. Off. .
3742798 6/1989 Fed. Rep. of Germany .

OTHER PUBLICATIONS

A. Graham Cairns-Smith et al., *Reactions of p-Nitrophenyl Dodecanoate in Normal and Modified Cholic Acid Micelles*, Journal of the Chemical Society, Perkin Transactions, 2. No. 10, 1978, pp. 1007–1010.

Joanne F. Kinneary, *Progress Toward Artificial Metalloenzymes: New Ligands for Transition Metal Ions and Neutral Molecules*, Journal of Inclusion Phenomena and Molecular Recognition in Chemistry, No. 7, 1989, pp. 155–168.

P. P. Nair et al., *Lithocholic Acid in Human Liver: Identification of E-Lithocholyl Lysine in Tissue Protein*, Lipids, vol. 12, No. 11, Nov. 1977, pp. 922–929.

Chemical Abstracts, vol. 108, No. 7, 1988, abstract No. 56445.
Chemical Abstracts, vol. 64, No. 5, 1966, abstract No. 6718A.
Chemical Abstracts, vol. 63, No. 13, 1965, abstract No. 18614H.
Chemical Abstracts, vol. 62, No. 6, 1965, abstract No. 6542D.
Chemical Abstracts, vol. 60, No. 5, 1964, abstract No. 5591A.
Chem. Abs. 108: 56445q, vol. 108, No. 7 (1988).
Kinneary, et al., *J. of Inclusion Phenomena & Molecular Recognition in Chemistry*, No. 7, pp. 155–168 (1989).

*Primary Examiner*—Marianne M. Cintins
*Assistant Examiner*—Kimberly J. Kestler
*Attorney, Agent, or Firm*—Finnegan, Henderson, Farabow, Garrett & Dunner

[57] ABSTRACT

The invention relates to bile acid derivatives of the formula I $$G1-X-G2 \quad (I)$$

in which
G1 and G2 are bile acid radicals or modified bile acid radicals in the form of the free acids, the esters or amides, the salt forms and also the forms derivatized on the alcohol groups and
X is a bridge group or a single covalent bond, it being possible for G1 and G2 to be optionally bonded via X.

The compounds according to the invention have a high affinity for the specific bile acid transport system of the small intestine and inhibit bile acid absorption in a concentration-dependent and competitive manner.

9 Claims, No Drawings

BILE ACID DERIVATIVES, PROCESS FOR THEIR PREPARATION AND USE OF THESE COMPOUNDS AS PHARMACEUTICALS

Bile acids have an important physiological the digestion of fat, for example as cofactors of pancreatic lipases and as natural detergents for the solubilization of fats and fat-soluble vitamins. As the final product of cholesterol metabolism, they are synthesized in the liver, stored in the gall bladder and released from the latter by means of contraction into the small intestine, where they display their physiological effect. The largest part of the secreted bile acids is recovered again by means of the enterohepatic circulation. They pass back to the liver again via the mesenterial veins of the small intestine and the portal vein system. During reabsorption in the intestine, both active and passive transport processes play a role. The main amount of the bile acids is reabsorbed by a specific $Na^+$-dependent transport system at the end of the small intestine, the terminal ileum, and they pass back to the liver with the blood of the mesenterial veins via the portal vein, in order to be secreted into the cell again by the liver cells. In the enterohepatic circulation, the bile acids appear both as free acids, but also in the form of glycerol and taurine conjugates.

Non-absorbable, insoluble, basic, cross-linked polymers have been used for some time for the binding of bile acids and are utilized therapeutically on the basis of these properties. The object of therapy is regarded as all diseases in which inhibition of gallic acid reabsorption in the intestine, in particular in the small intestine, appears desirable. For example, chologenic diarrhea after resection of the ileum, also increased cholesterol blood levels, are treated in this manner.

In the case of increased cholesterol blood level, a reduction in this level can be achieved by intervention in the enterohepatic circulation. The corresponding new synthesis of bile acids from cholesterol in the liver is forced by reduction of the bile acid pool in the enterohepatic circulation. To cover the need for cholesterol in the liver, resort is made to the LDL cholesterol (low density lipoprotein) in the blood circulation, the hepatic LDL receptors coming into effect in increased number. The acceleration of LDL catabolism thus taking place results in the reduction of the atherogenic cholesterol content in the blood. Until now, these polymeric, insoluble ion exchanger resins (known in the following as "resins") represented the only possibility of influencing the enterohepatic circulation with respect to increased bile acid excretion and consequent reduction of the cholesterol level.

In this case, the effective daily dose for the "resins" used as pharmaceuticals, for example colestyramine (contains quaternary ammonium groups) or colestipol (contains secondary or tertiary amino groups) is very high. For example, for colestyramine it is 12–24 g l highest daily dose 32 g, and 15–30 g is the recommended colestipol dose. In addition to the high dosage, taste and odor make patients, compliance difficult.

The known side effects of the "resins" originate from deficient selectivity (for example avitaminoses), which also have to be taken into account in the dosage of medicoments given simultaneously, but also from bile acid depletion which produce various gastrointestinal disorders (constipation, steatorrhea) to differing degrees. A therapeutic importance for both preparations has been described by combination with other pharmaceuticals having a hypolipidemic effect such as fibrates, HMG-CoA reductase inhibitors, probucol (cf., for example M. N. Cayen, Pharmac. Ther. 29, 187 (1985) and 8th International Symposium on Atherosclerosis, Rome, Oct. 9–13, 1988, Abstracts pp. 544, 608, 710), the effects achieved also making possible the treatment of severe hyperlipidemias. It therefore appears meaningful to find suitable substances with the given principle of action and without the disadvantages of the preparations used at present.

The following features of said preparations and in particular of colestipol are to be regarded as worthy of improvement:

The high daily doses, which are to be traced back to a relatively low binding rate in the case of neutral pH in isotonic medium and the (in some cases) rerelease of the adsorbed bile acids.

The qualitative shift in the bile acid composition of the bile with a decreasing tendency for chenodesoxycholic acid and the increasing risk of cholelithiasis associated with it.

The absence of a damping effect on the cholesterol metabolism of the intestinal bacteria.

The overhigh binding rate of vitamins and pharmaceuticals makes a need for substitution of these substances and blood level controls possibly necessary.

Due to the binding of the bile acids to the "resins" already in the duodenum and upper small intestine, bile acids are available in insufficient amount for the digestion of fats, so that fat digestion disorders occur.

The administration form has until now been regarded as unsatisfactory.

The object was therefore to find a pharmaceutical which was able to reduce the atherogenic cholesterol content in the blood or to influence the enterohepatic circulation with respect to increased bile acid excretion and consequent reduction of the cholesterol level, but which does not have the disadvantages of the "resins" used until now.

Surprisingly, bile acid derivatives of the formula I $$G1-X-G2 \qquad (I)$$

have now been found in which

G1 and G2 are bile acid radicals or modified bile acid radicals in the form of the free acids, the esters or amides, the salt forms and also the forms derivatized on the alcohol groups and is a bridge group or a single covalent bond, it being possible for G1 and G2 to be optionally bonded via X.

The compounds of the formula I according to the invention have a high affinity for the specific bile acid transport system of the small intestine and inhibit bile acid absorption in a concentration-dependent and competitive manner.

Furthermore, the compounds according to the invention are themselves not absorbed and thus do not pass into the blood circulation. The enterohepatic circulation of the bile acids can be interrupted very much more specifically and efficiently by the use of this new active compound principle. Intervention into the enterohepatic circulation can now be made with higher efficiency by the use of this completely new active compound principle than the "resins" have allowed until now.

The listed deficiencies of the "resins" on the market intervening in the enterohepatic circulation can be completely avoided by the use of the compounds according to the invention which work according to the new principle of action. The bile acid concentration in the enterohepatic circulation is also reduced in a substantially more effective manner by reversible inhibition of the bile acid reabsorption in the small intestine, so that a reduction in the cholesterol level in the serum takes place. Avitaminoses are then to be expected just as little on using the compounds according to the invention as the influence on the absorption of other medicoments or also the negative effect on the intestinal flora. The known side effects (constipation, steatorrhea) are additionally not observed, i.e. the digestion of fat is not influenced negatively. Because of the high affinity of the compounds according to the invention for the highly specific bile acid transport system in the small intestine, it is possible to manage with very much lower daily doses in contrast to the "resins", so that the acceptance of such pharmaceuticals by doctor and patient and the compliance of the patients is very high.

Preferred compounds of the formula I are those in which the ring A of the bile acid radical G2, which is a bile acid or a modified bile acid, in particular a form modified on the alcohol groups, is not linked with the ring A of the bile acid radical G1, which is also a bile acid or a modified bile acid.

An unsymmetrical linkage of the radicals G1 and G2 is moreover preferred, i.e. a linkage via different rings.

Particularly preferred compounds of the formula I are those in which the bile acid radical G1, which is a bile acid or a modified bile acid, in particular a form modified on the alcohol groups, is linked to the connecting member X via the carbon atom C24 (ring D), X is a bridge group and the bile acid radical G2, which is a bile acid or a modified bile acid, in particular a form modified on the alcohol groups, is linked to X via one of the positions C3 (ring A), C7 (ring B) or C12 (ring C).

Particularly preferred compounds of the general formula I are those in which

G1 is a compound of the general formula II

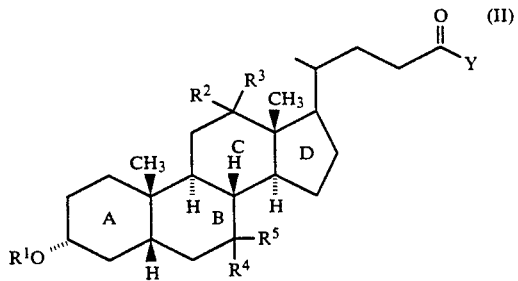

in which

Y is a free valency for bonding the group X or has the following meaning —OL, —NHL, —NL$_2$, an amino acid or aminosulfonic acid bonded via the amino group, such as, for example

—NHCH$_2$—CO$_2$H, —NH—CH$_2$CH$_2$—SO$_3$H,

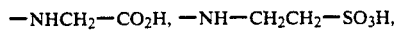
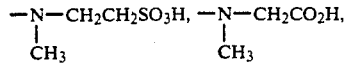

-continued

—NH—CHCO$_2$H
       |
       R$^6$ and their (C$_1$-C$_4$) alkyl esters and alkali metal and alkaline earth metal salts, —OKa, where Ka is a cation, such as, for example, an alkali metal or alkaline earth metal ion or alternatively a quaternary ammonium ion and in which L is H, a saturated or unsaturated alkyl radical having 1-10 carbon atoms, which is branched or unbranched, a cycloalkyl radical having 3-8 carbon atoms, a phenyl radical which is unsubstituted or monosubstituted to trisubstituted by F, Cl, Br, (C$_1$-C$_4$)alkyl or (C$_{1-4}$)-alkoxy, a benzyl radical which is unsubstituted or monosubstituted to trisubstituted by F, Cl, Br, (C$_1$-C$_4$)-alkyl or (C$_1$-C$_4$)-alkoxy, and R$^6$ is methyl, isopropyl, isobutyl, 2-butyl, benzyl, 4-hydroxybenzyl, hydroxymethyl, 1-hydroxyethyl, H$_3$CSCH$_2$CH$_2$—, HO$_2$CCH$_2$— or HO$_2$CCH$_2$CH$_2$—, R$^1$ is a free valency for bonding the group X or H, a saturated or unsaturated alkyl radical having 1-10 carbon atoms, which is branched or unbranched, a cycloalkyl radical having 3-8 carbon atoms, a phenyl radical which is unsubstituted or monosubstituted to trisubstituted by F, Cl, Br, (C$_1$-C$_4$)-alkyl or (C$_1$-C$_4$)-alkoxy, —N⊕H$_3$, —OPO$_3$⊕, a benzyl radical which is unsubstituted in the ring or monosubstituted to trisubstituted by F, Cl, Br, (C$_1$-C$_4$)-alkyl, (C$_1$-C$_4$)-alkoxy, —N⊕H$_3$, —OPO$_3$⊕, or phenyl, which can in turn be monosubstituted to trisubstituted by F, Cl, Br, (C$_1$-C$_4$)-alkyl or (C$_1$-C$_4$)-alkoxy, —N⊕H$_3$, —OPO$_3$⊕, a biphenylmethyl radical which is unsubstituted or monosubstituted to trisubstituted by F, Cl, Br, (C$_1$-C$_4$)-alkyl or (C$_1$-C$_4$)-alkoxy, —N⊕H$_3$, —OPO$_3$⊕, a triphenylmethyl radical which is unsubstituted or monosubstituted to trisubstituted by F, Cl, Br, (C$_1$-C$_4$)-alkyl or (C$_1$-C$_4$)-alkoxy, —N⊕H$_3$, —OPO$_3$⊕, a 1- or 2-naphthylmethyl radical which is unsubstituted or monosubstituted to trisubstituted by F, Cl, Br, (C$_1$-C$_4$)-alkyl or (C$_1$-C$_4$)-alkoxy, —N⊕H$_3$, —OPO$_3$⊕, a 9-fluorenyl radical which is unsubstituted or monosubstituted to trisubstituted by F, Cl, Br, (C$_1$-C$_4$)-alkyl or (C$_1$-C$_4$)-alkoxy, a 2-, 3- or 4-pyridyl radical, $$-\underset{\underset{OL}{|}}{\overset{\overset{O}{\|}}{P}}-OL, \quad -\underset{\underset{O}{\|}}{\overset{\overset{O}{\|}}{S}}-OL \text{ or } -\overset{\overset{O}{\|}}{C}-L$$

where L has the abovementioned meaning

R$^2$ to R$^5$, where R$^2$ and R$^3$ or R$^4$ and R$^5$ in each case together are the oxygen of a carbonyl group, or individually and in each case independently of one another are

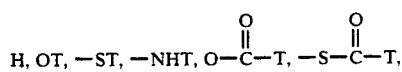
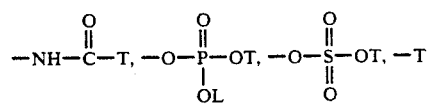

where L has the abovementioned meaning and T has the meaning of L or a free valency for bonding the group X, with the restriction that altogether only one free valency for bonding the group X starts from G1, X is a single bond or a group of the general formula III

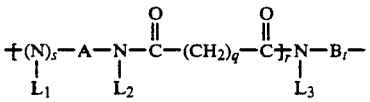 (III)

where

A is an alkylene chain which is branched or unbranched, saturated or unsaturated and can be optionally interrupted in the chain by —O—, —S— or arylene, in particular phenylene, where the linkage

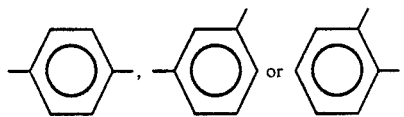

takes place and the chain includes altogether 2 to 12, preferably 2 to 6 chain members p.

B is an alkylene chain which is branched or unbranched, saturated or unsaturated and can be optionally interrupted in the chain by —O—, —S— or arylene, in particular phenylene, where the linkage

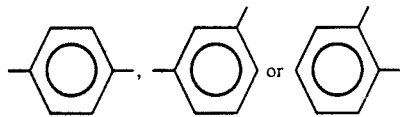

takes place and the chain contains altogether 2 to 18, preferably 2 to 12 chain members n, $L_1$, $L_2$ and $L_3$ are identical or different and have the meaning of L, and q is 0-5,
r is 0 or 1 and
s is 0 or 1
t is 0 or 1, G2 is a compound of the general formula IV

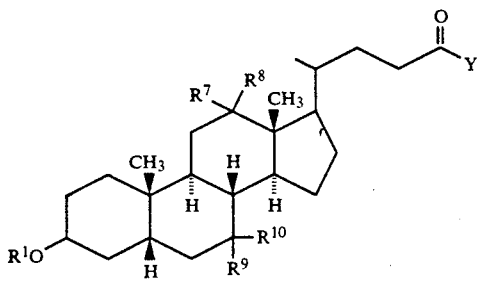

in which

Y and $R^1$ have the meaning indicated under G1 and $R^7$ to $R^{10}$, where $R^7$ and $R^8$ or $R^9$ and $R^{10}$) in each case together are the oxygen of a carbonyl group or individually and in each case independently of one another are H, OT, —ST, —NHT,

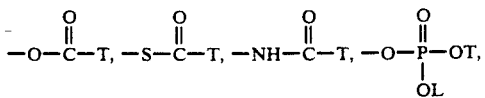

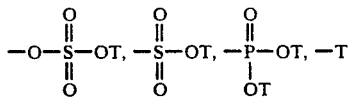

where L and T have the meaning indicated under G1, likewise with the restriction that altogether only one free valency for bonding the groups X starts from G2.

Preferred compounds are those of the general formula I in which the linkage of the two compounds G1 and G2 by the group X does not take place by the rings A of both compounds G1 and G2.

Particularly preferred compounds of the general formula I are those in which the linkage via the group X does not take place via identical rings of the compounds G1 and G2.

Particularly preferred compounds of the general formula I are those in which the linkage by the group X takes place unsymmetrically via the rings A or D of the compounds G1 and G2.

The invention further relates to a process for the preparation of compounds of the general formula I, which comprises a) if X=a single bond, bringing suitable reactive forms of G1 and G2 to reaction with one another by processes known in principle or b) if X=a bridging group α) bringing reactive forms of G1-X to reaction with G2 or β) reactive forms of G2-X to reaction with G1 by processes known in principle or c) preparing compounds of the general formula I (G1-X-G2) from G1-X1 by known or, if not known, by the processes described below in more detail, X being formed from X1 and X2 by construction of a covalent bond, in particular in the course of a condensation or substitution reaction.

a) X=single bond The bile acids G1 are employed either in free form or in protected form. After linkage with G2, which is is likewise present in free or protected form, removal of the protective groups and conversion of the C24 carboxyl function into an abovementioned derivative is optionally carried out. Suitable protective groups for the alcohol groups are expediently formyl, acetyl, tetrahydropyranyl or t-butyldimethylsilyl. Suitable protective groups for the C24 carboxyl group are various alkyl or benzyl esters, but also, for example, orthoesters.

For example, bile acid preferably reacts in position 3, but also in position 7, with activated forms of carboxylic acids, such as acid chlorides or mixed anhydrides with the addition of bases such as trialkylamine or pyridine, but also NAOH at room temperature in suitable solvents such as tetrahydrofuran, methylene chloride or ethyl acetate, but also dimethylformamide (DMF) or dimethoxyethane (DME).

The various isomers can be separated, for example, by gas chromatography.

The reaction can be carried out selectively by the use of suitable protective groups. Analogously, appropriate amino bile acids can be converted into corresponding amides. Here too, the reaction can either be carried out with protected or free bile acids.

Other compounds according to the invention can also be linked analogously according to known standard processes.

b) X=a bridge group The processes indicated under a) are also used to carry out the linkage of G1-X with G2 or G1 with X-G2. Expediently, the bile acid moiety is also either employed here in protected form or unprotected form.

A preferred preparation process comprises reacting reactive forms of G1 with reactive forms X-G2. If appropriate, the linkage is followed by the removal of protective groups and the conversion of C24 carboxyl to derivatives.

The preparation of reactive bile acid building blocks X-G is indicated in reaction schemes 1-4 as exemplified by cholic acid (for example r=0). Preparation of reactive bile acid building blocks X-G2 as exemplified by cholic acid, Schemes 1-4

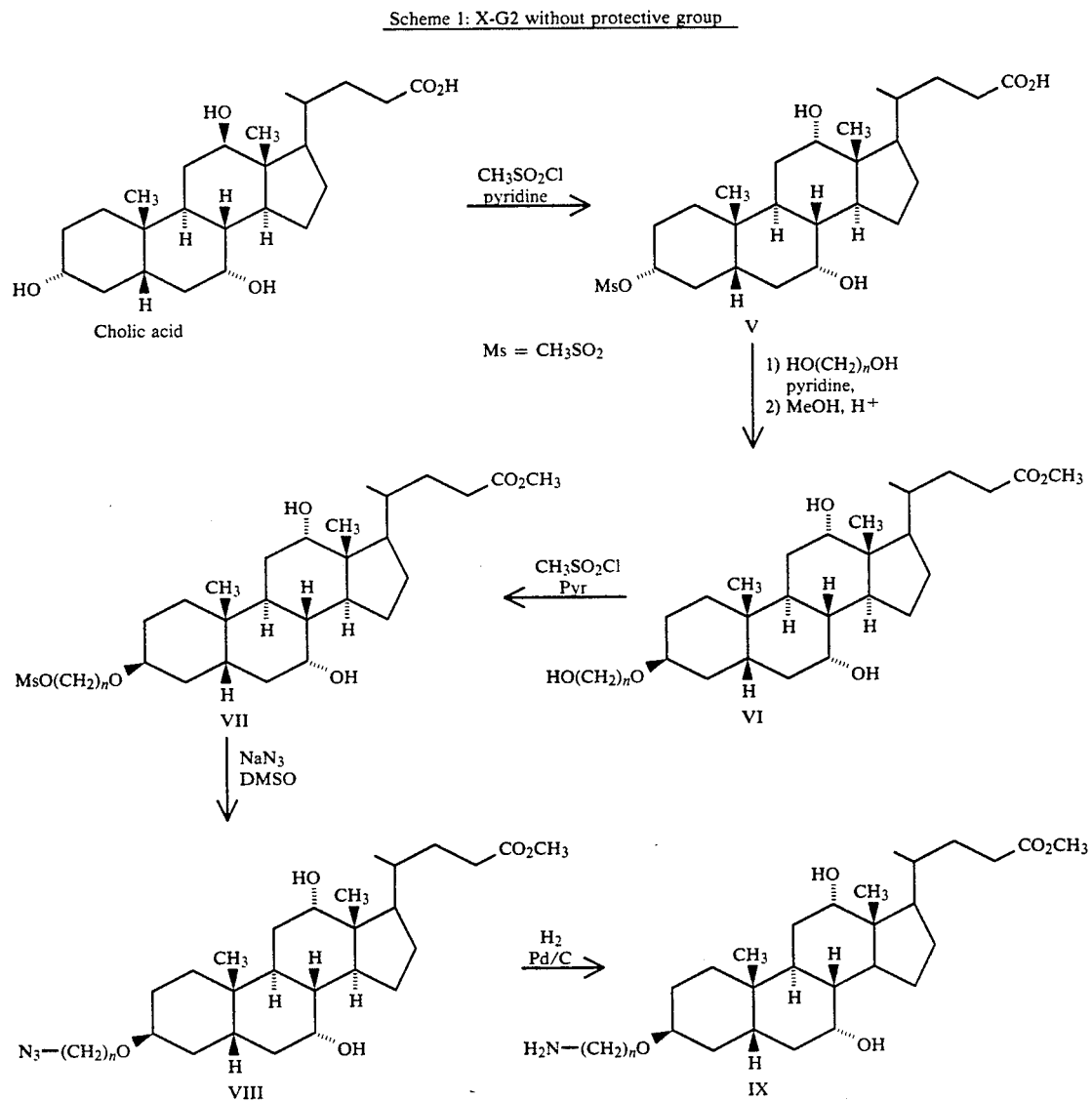

Scheme 1: X-G2 without protective group

Scheme 2: X-G2 with THP protective group (THP = tetrahydropyranyl)
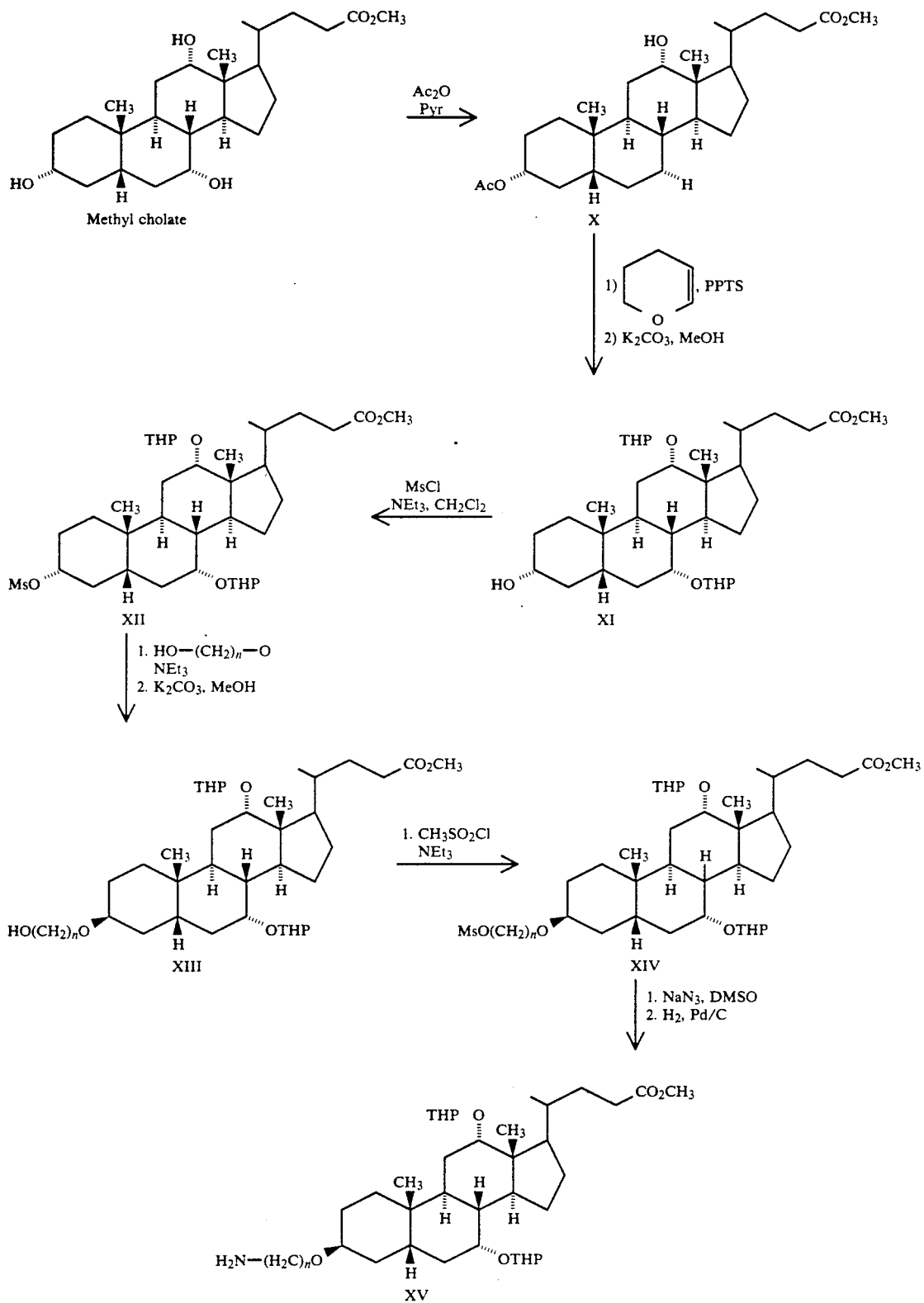

Scheme 3: X-G2 with t-BuMe2Si protective group
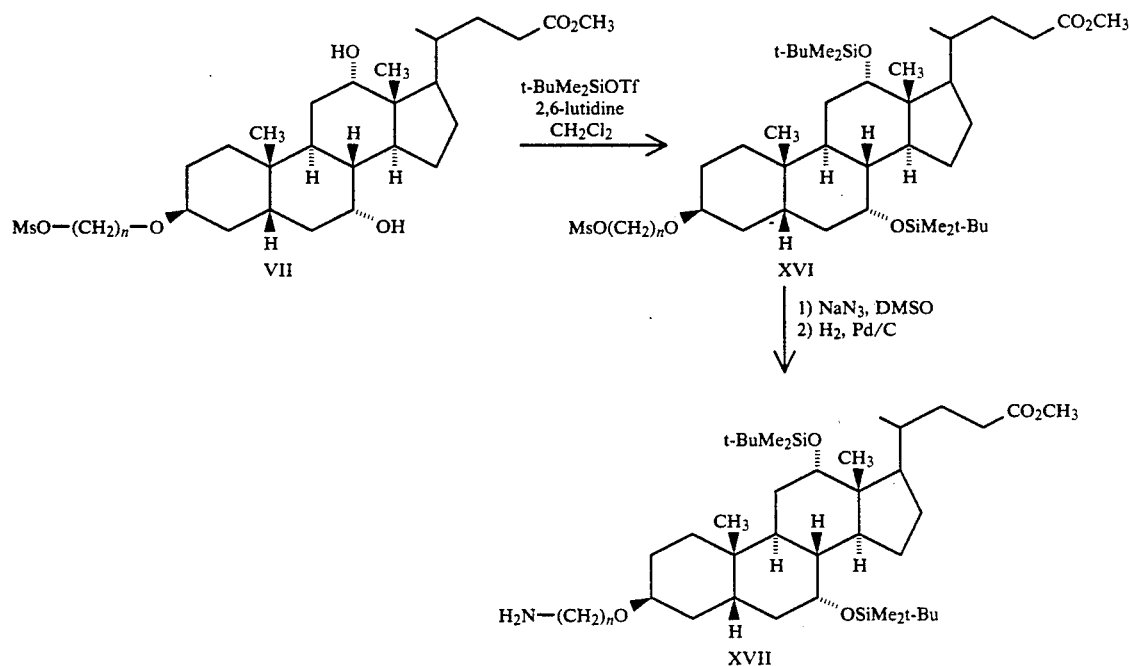
Scheme 4: X-G2 with α-configuration on C3
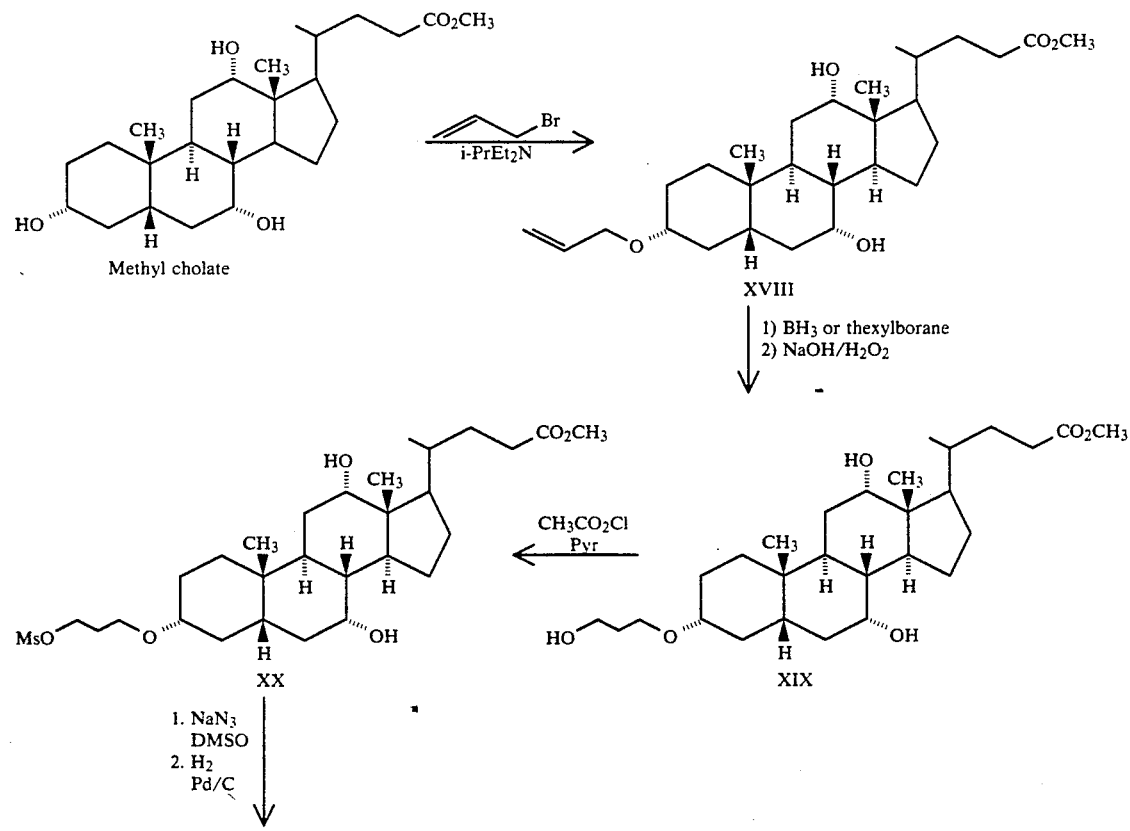

-continued
Scheme 4: X-G2 with α-configuration on C3

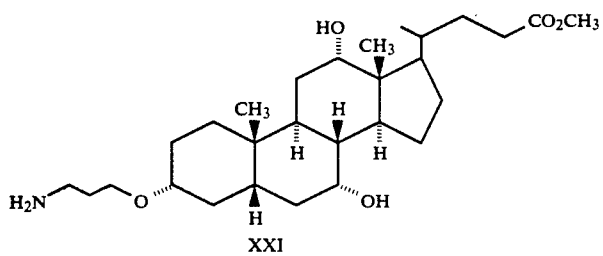

The replacement of the 3—OH groups by diols HO(CH$_2$)$_n$OH is carried out by reaction of the appropriate mesylates with the appropriate diols, which are preferably employed in excess, with the addition of bases such as pyridine or lutidine, but also triethylamine.

The primary OH groups of the compounds VI and XIII can be further reacted by standard methods. Thus, for example, XIII can be converted into the corresponding carboxylic acid XXII (where R(11) is equal to THP] with oxidants, preferably with chromium(VI) reagents or various potassium permanganate systems.

according to the general formula I (G1-X-G2) using an appropriately modified G1-X1.

The latter case is described in part c).

c) To prepare a compound of the type X2-G2, one of the compounds IX, XV, XVII or XXI is reacted to give carboxylic acids XXIII, as here in the example, with reactive forms of carboxylic acids, for example mixed anhydrides, acid chlorides or, for example, if q=2, with succinic anhydride in a suitable solvent, such as, for example, dichloromethane, toluene or pyridine and in the presence of triethylamine at −20° to room temperature.

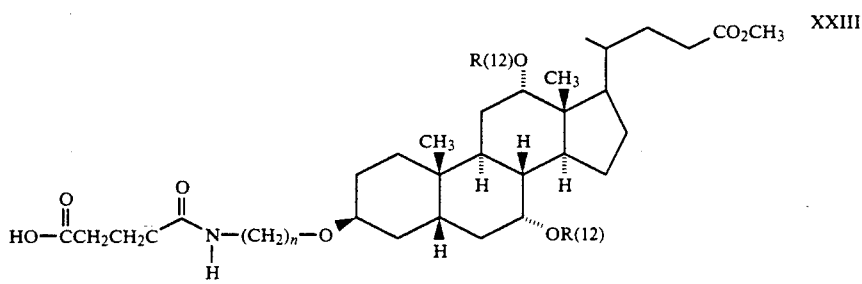

Correspondingly, other protective groups are also suitable.

R(12)=H, THP, t-BuMe$_2$Si acetyl, benzyl, benzyloxycarbonyl (Z)

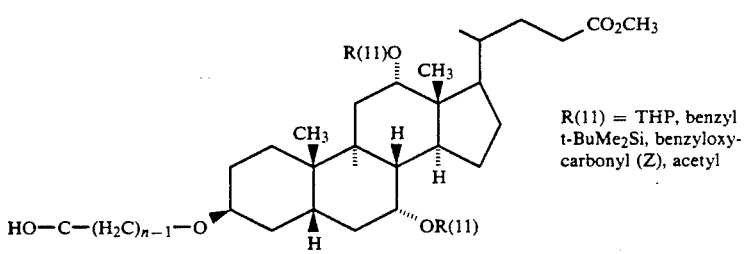

R(11) = THP, benzyl
t-BuMe$_2$Si, benzyloxycarbonyl (Z), acetyl

The compounds XG2 (IX, XV, XVII or XXI) can only be reacted directly with G1 or its derivatives, or after conversion into X2-G2, converted into a compound The compound (XXIII) can now in turn be reacted again with compounds IX, XV, XVII or XXI (in this case: type G1-X1) to give compounds of the general formula I in which s=O (in this case compound XXIV).

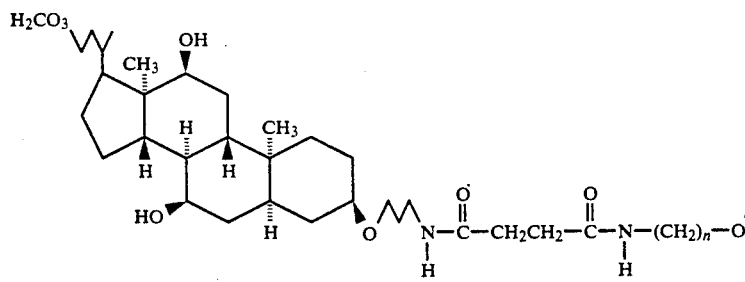
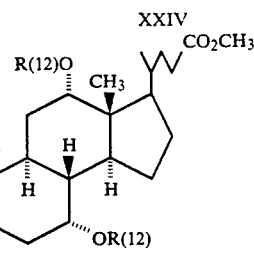

If it is intended to prepare compounds of the general formula I in which s=1, compounds of the general formula II, for example, are reacted with compounds

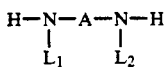

in which A, $L_1$ and $L_2$ have the abovementioned meaning. In the case of the ester (i.e.

is an ester function), this is directly reacted with

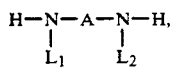

in the case of the free acid

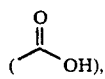

this must additionally be employed in the form of reactive acid derivatives, such as, for example, mixed anhydrides or acid chlorides. The compounds of the type G1-X1 formed in this manner are then converted into compounds of the type G1-X-G2 using compounds of the type G2-X2.

The abovementioned embodiments for the preparation of the compounds of the type G1-X-G2 in which the linkage of the two bile acids G1 and G2 is effected via their respective A rings also apply in modified methods correspondingly known to the person skilled in the art for linkages A-D, A-B or A-C, and also D-D, B-B, C-C, B-D, B-C or C-D.

The substituents of the bile acid G1 or G2, $R^1$ to $R^{10}$, can be introduced either before the linkage of G1 with G2 via X or else afterwards. Introduction of the substituents taking place after the linkage of G1 with G2 is only possible if the corresponding substituents are not directly involved themselves in the bridge formation between G1 or G2 and X. These substitutions are therefore preferably performed before the actual linkage reactions of G1 and G2 via X.

The invention furthermore relates to the use of the compounds according to the invention for the production of a medicoment.

For this purpose, the compounds of the general formula I are dissolved or suspended in pharmacologically acceptable organic solvents, such as mono- or polyhydric alcohols, such as, for example, ethanol or glycerol, in triacetin, oils such as, for example, sunflower oil, cod liver oil, ethers, such as, for example, diethylene glycol dimethyl ether or alternatively polyethers such as, for example, polyethylene glycol, or alternatively in the presence of other pharmacologically acceptable polymer excipients, such as, for example, polyvinylpyrrolidone, or other pharmaceutically acceptable additives such as starch, cyclodextrin or polysaccharides. The compounds according to the invention can additionally be given in combination with other pharmaceutical substances.

The compounds of the formula I are administered in various dosage forms, preferably orally in the form of tablets, capsules or liquids. The daily dose varies in the range from 3 mg to 5000 mg depending on the body weight and constitution of the patient, but preferably in the dose range 10-1000 mg.

The pharmacological data include a series of tests in which the interaction of the compounds according to the invention with the intestinal bile acid transport system was investigated in the terminal small intestine:

1. Preparation of brush-border membrane vesicles from the ileum of rabbits

The preparation of brush-border membrane vesicles from the intestinal cells of the small intestine was carried out using the so-called $Mg^{2+}$ precipitation method. Male New Zealand rabbits (2-2.5 kg body weight) were sacrificed by intravenous injection of 0.5 ml of an aqueous solution of 2.5 mg of tetracaine HCl, 100 T 61 ® and 25 mg of mebezonium iodide. The small intestine was removed and rinsed with ice-cold physiological saline solution. The terminal 7/10 of the small intestine (measured in the oral-rectal direction, i.e. the terminall ileum, which contains the active $Na^+$-dependent bile acid transport system) were used for preparation of the brush-border membrane vesicles. The intestines were frozen at $-80°$ C. under nitrogen in plastic bags. The frozen intestines were thawed in a water bath at 30° C. in order to prepare the membrane vesicles. The mucosa was scraped off and suspended in 60 ml of ice-cold 12 mM trio/HCl buffer (pH 7.1)/300 mM mannitol, 5 mM EGTA/10 mg/l of phenylmethylsulfonyl fluoride/1 mg/l of soybean trypsin inhibitor (32 U/mg)/0.5 mg/l of bovine lung trypsin inhibitor (193 U/mg)/0.5 mg/l of bacitracin. After diluting to 300 ml with ice-cold distilled water, the suspension was homogenized with ice-cooling for 3 minutes at 75% of maximum power using an Ultraturrax (18 rod, IKA Werk Staufen, Federal Republic of Germany). After addition of 3 ml of 1M $MgCl_2$ solution (final Concentration 10 mM), the homogenate was allowed to stand at 0° C. for exactly 1 minute. As a result of addition of $Mg^{2+}$, the cell membranes aggregate and precipitate with the exception of the brush-border membranes. After centrifugation at 3,000×g (5,000 rpm, SS-34 rotor) for 15 minutes, the precipitate is discarded and the supernatant which contains the brush-border membranes is centrifuged at 26,700×g (15,000 rpm, SS-34 rotor) for 30 minutes. The supernatant was discarded, and the precipitate was rehomogenized in 60 ml of 12 mM tris/HCl buffer (pH 7.1)/60 mM mannitol, 5 mM EGTA using a Potter Elvejhem homogenizer (Braun Melsungen, 900 rpm, 10 strokes). After addition of 0.1 ml of 1M $MgCl_2$ solution and an incubation time of 15 minutes at 0° C., the mixture was again centrifuged at 3,000×g for 15 minutes. The supernatant was then again centrifuged at 46,000×g (15,000 rpm, SS-34 rotor) for 30 minutes. The precipitate was taken up in 30 ml of 10 mM tris/hepes buffer (pH 7.4) /300 mM mannitol and homogeneously resuspended by 20 strokes in a Potter Elvejhem homogenizer at 1,000 rpm. After centrifugation at 48,000×g (20,000 rpm, SS-34 rotor) for 30 minutes, the precipitate was taken up in 0.5 to 2 ml of tris/hepes buffer (pH 7.4)/280 mM mannitol (final concentration 20 mg/ml) and resuspended with the aid of a tuberculin syringe using a 27 gauge needle. The vesicles were either used immediately after preparation for transport investigations or stored at −196° C. in liquid nitrogen in 4 mg portions.

2. Inhibition of $Na^+$-dependent [$^3$H]taurocholate absorption into brush-border membrane vesicles of the ileum The absorption of substrates into brush-border membrane vesicles was determined by means of the so-called membrane filtration technique. 10 μl of the vesicle suspension (100 μg of protein) were pipetted on the wall of a polystyrene incubation tube (11×70 mm) as a drop which contained the incubation medium together with the corresponding ligands (90 μl). The incubation medium contained 0.75 μl=0.75 μCi [$^3$H(G)]-taurocholate (specific activity: 2.1 Ci/mmol), /0.5 μl 10 mM taurocholate/ 8.75 μl of sodium transport buffer (10 mM tris/hepes, (pH 7.4)/100 mM mannitol/100mM NaCl) (Na-T-B) or 8.75 μl of potassium transport buffer (10 mM tris/hepes (pH 7.4)/ 100 mM mannitol/100 mM KCl) (K-T-B) and 80 μl of the relevant inhibitor solution, depending on the experiment, in Na-T buffer or K-T buffer. The incubation medium was filtered through a polyvinylidene fluoride membrane filter (SYHV LO 4NS, 0.45 μm, 4 mm φ, Millipore, Eschborn, Federal Republic of Germany). The transport measurement was begun by mixing the vesicles with the incubation medium. The concentration of taurocholate in the incubation batch was 50 μM. After the desired incubation time (customarily 1 min), the transport was stopped by addition of 1 ml of ice-cold stop solution (10 mM tris/hepes, (pH 7.4)/150 mM KCl). The resulting mixture was immediately filtered off with suction in a vacuum of 25 to 35 mbar through a membrane filter made of cellulose nitrate (ME 25, 0.45 μm, 25 mm diameter, Schleicher & Schuell, Dassell, Federal Republic of Germany). The filter was subsequently washed with 5 ml of ice-cold stop solution.

In order to measure the absorption of the radioactively labeled taurocholate, the membrane filter was dissolved using 4 ml of the scintillator Quickszint 361 (Zinsser Analytik GmbH, Frankfurt, Federal Republic of Germany) and the radioactivity was measured by liquid scintillation counting in a TriCarb 2500 counter (Canberra Packard GmbH, Frankfurt, Federal Republic of Germany). The values measured were obtained as dpm (decompositions per minute) after calibration of the apparatus with the aid of standard samples and after correction for possible chemiluminescence.

The control values were in each case determined in NA-T-B and K-T-B. The difference between the absorption in NA-T-B and K-T-B gave the $Na^+$-dependent transport component. The $IC_{50} Na^+$ was designated as that concentration of inhibitor at which the $Na^+$-dependent transport component was inhibited by 50%, relative to the control; the same applies to the data for the $IC_{25}$ and $IC_{75}$ values. The results are collected in Table 60.

The following examples describe the invention, but without having a restrictive effect on it.

EXAMPLE 1

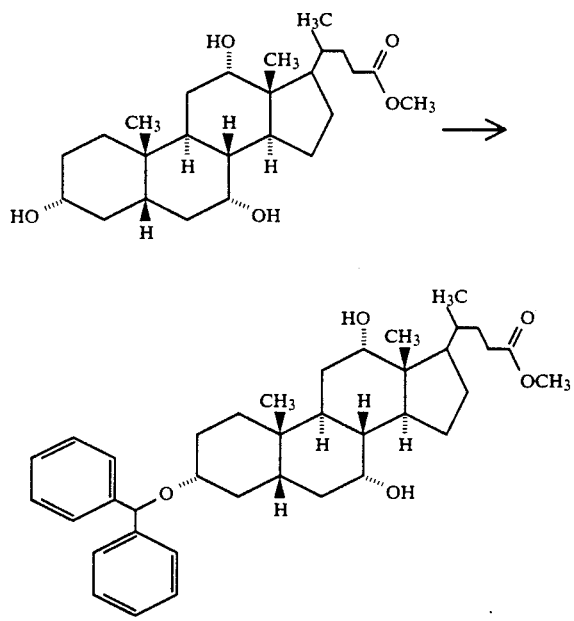

16.9 g (40 mmol) of methyl cholate were initially introduced into 120 ml of N-ethyldiisopropylamine, 11.9 g (48 mmol) of diphenylmethyl bromide were added and the mixture was stirred at 100° C. for 4 hours. For working-up, 250 g of ice/20 ml of sulfuric acid were added after cooling and the mixture was extracted with ethyl acetate (3×). The combined organic phases were dried with magnesium sulfate and evaporated. Chromatography on silica gel (n-heptane/ethyl acetate=3:1) gave 11.8 g (20 mmol, 50%) of "Example 1"

$C_{38}H_{52}O_5$ (588) MS (FAB, 3-NBA/LiCl : 595 ($M+Li^+$)

The examples of Tables 1-4 were obtained in analogy to Example 1.

TABLE 1

Structure: steroid with 3α-OR¹, 7α-OH, 12α-OH, methyl ester side chain

| Ex. | R¹ | MS (FAB, 3-NBA/LiCl or LiI) |
|---|---|---|
| 2 | benzyl (PhCH₂–) | $C_{32}H_{48}O_5$ (512); 519 (M + Li⁺) |
| 3 | trityl-methyl (Ph₃C–CH₂–) | $C_{44}H_{56}O_5$ (664); 671 (M + Li⁺) |
| 4 | 4-chlorobenzyl | $C_{32}H_{47}ClO_5$ (546); 553 (M + Li⁺) |
| 5 | 2,6-dimethylbenzyl | $C_{34}H_{52}O_5$ (540); 547 (M + Li⁺) |
| 6 | 2,4-dichlorobenzyl | $C_{32}H_{46}Cl_2O_5$ (580); 587 (M + Li⁺) |
| 7 | 4-methoxybenzyl | $C_{33}H_{50}O_6$ (542); 549 (M + Li⁺) |
| 8 | 3-pyridylmethyl | $C_{31}H_{47}NO_5$ (513); 520 (M + Li⁺) |
| 9 | 2-naphthylmethyl | $C_{36}H_{50}O_5$ (562); 569 (M + Li⁺) |

TABLE 2

Structure: steroid with 3α-OR¹, 7α-OH, methyl ester side chain

| Ex. | R¹ | MS (FAB, 3-NBA/LiCl or LiI) |
|---|---|---|
| 10 | benzyl | $C_{32}H_{48}O_4$ (496); 503 (M + Li⁺) |
| 11 | trityl-methyl | $C_{44}H_{56}O_4$ (648); 655 (M + Li⁺) |
| 12 | diphenylmethyl (CHPh₂) | $C_{38}H_{52}O_4$ (572); 579 (M + Li⁺) |
| 13 | 4-chlorobenzyl | $C_{32}H_{47}ClO_4$ (530); 537 (M + Li⁺) |
| 14 | 2,6-dimethylbenzyl | $C_{34}H_{52}O_4$ (524); 531 (M + Li⁺) |
| 15 | 2,4-dichlorobenzyl | $C_{32}H_{46}Cl_2O_4$ (564); 571 (M + Li⁺) |
| 16 | 4-methoxybenzyl | $C_{33}H_{50}O_5$ (526); 533 (M + Li⁺) |
| 17 | 3-pyridylmethyl | $C_{31}H_{47}NO_4$ (497); 504 (M + Li⁺) |
| 18 | 2-naphthylmethyl | $C_{36}H_{50}O_4$ (546); 553 (M + Li⁺) |

TABLE 3

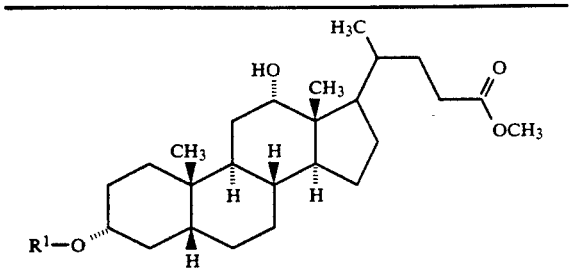

| Ex. | R¹ | MS (FAB,3-NBA/LiCl or LiI) |
|---|---|---|
| 19 | phenethyl | $C_{32}H_{48}O_4$(496); 503 (M + Li⁺) |
| 20 | 1,1-diphenyl-1-phenylethyl (cumyl-type, trityl-ethyl) | $C_{44}H_{56}O_4$(648); 655 (M + Li⁺) |
| 21 | 2,2-diphenylethyl | $C_{38}H_{52}O_4$(572); 579 (M + Li⁺) |
| 22 | 4-chlorophenethyl | $C_{32}H_{47}ClO_4$(530); 537 (M + Li⁺) |
| 23 | 2,6-dimethylphenethyl | $C_{34}H_{52}O_4$(524); 531 (M + Li⁺) |
| 24 | 2,4-dichlorophenethyl | $C_{32}H_{46}Cl_2O_4$(564); 571 (M + Li⁺) |
| 25 | 4-methoxyphenethyl | $C_{33}H_{50}O_5$(526); 533 (M + Li⁺) |
| 26 | 3-pyridylethyl | $C_{31}H_{47}NO_4$(497); 504 (M + Li⁺) |
| 27 | 2-naphthylethyl | $C_{36}H_{50}O_4$(546); 553 (M + Li⁺) |

TABLE 4

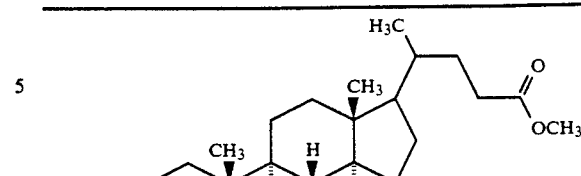

| Ex. | R¹ | MS (FAB,3-NBA/LiCl or LiI) |
|---|---|---|
| 28 | phenethyl | $C_{32}H_{48}O_3$(480); 487 (M + Li⁺) |
| 29 | 2,2-diphenylethyl | $C_{38}H_{52}O_3$(556); 563 (M + Li⁺) |
| 30 | triphenylmethylethyl | $C_{44}H_{56}O_3$(632); 639 (M + Li⁺) |
| 31 | 4-chlorophenethyl | $C_{32}H_{47}ClO_3$(514); 521 (M + Li⁺) |
| 32 | 2,6-dimethylphenethyl | $C_{34}H_{52}O_3$(508); 515 (M + Li⁺) |
| 33 | 2,4-dichlorophenethyl | $C_{32}H_{46}Cl_2O_3$(548); 555 (M + Li⁺) |
| 34 | 4-methoxyphenethyl | $C_{33}H_{50}O_4$(510); 517 (M + Li⁺) |
| 35 | 3-pyridylethyl | $C_{31}H_{47}NO_3$(481); 488 (M + Li⁺) |
| 36 | 2-naphthylethyl | $C_{36}H_{50}O_3$(530); 537 (M + Li⁺) |

EXAMPLE 37

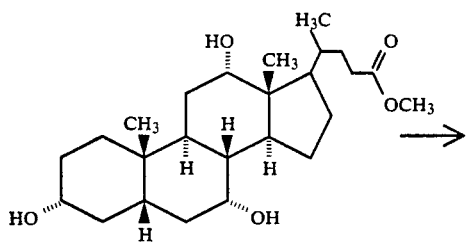

→

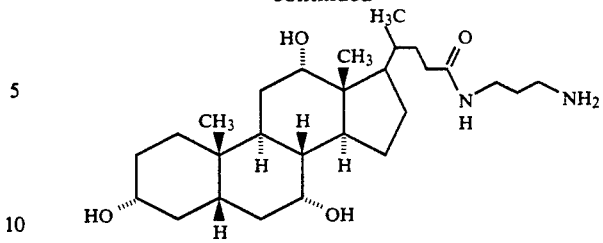

300 g (0.71 mol) of methyl cholate were stirred under reflux for 5 hours with 2.5 l of 1,3-diaminopropane.

For working-up, the mixture was evaporated, 2 l of icewater were added and the mixture was stirred intensively for 1 hour. The residue was filtered off with suction and dried in a vacuum drying oven at 75° C. for one day.

Yield: 306 g (0.65 mol, 92%)

$C_{27}H_{48}N_2O_4$ (464), MS (FAB, 3-NBA/LiCl) : 471 (M+Li$^+$)

The examples of Tables 5 to 8 were obtained in analogy to Example 37.

TABLE 5

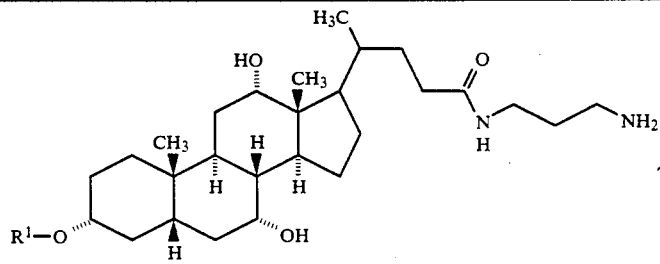

| Ex. | R$^1$ | MS (FAB,3-NBA/LiCl or LiI) |
|---|---|---|
| 38 | benzyl (PhCH$_2$CH$_2$–) | $C_{34}H_{54}N_2O_4$(554); 561 (M + Li$^+$) |
| 39 | diphenylmethyl (Ph$_2$CH–) | $C_{40}H_{58}N_2O_4$(630); 637 (M + Li$^+$) |
| 40 | triphenylmethyl (Ph$_3$C–) | $C_{46}H_{62}N_2O_4$(706); 713 (M + Li$^+$) |
| 41 | 4-chlorobenzyl | $C_{34}H_{53}ClN_2O_4$(588); 595 (M + Li$^+$) |
| 42 | 2,6-dimethylbenzyl | $C_{36}H_{58}N_2O_4$(582); 589 (M + Li$^+$) |

TABLE 5-continued
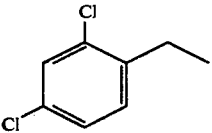
| Ex. | R¹ | MS (FAB,3-NBA/LiCl or LiI) |
|---|---|---|
| 43 | 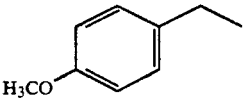 | $C_{32}H_{52}Cl_2N_2O_4(622); 629 \ (M + Li^+)$ |
| 44 | 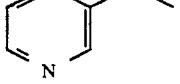 | $C_{32}H_{56}N_2O_4(584); 591 \ (M + Li^+)$ |
| 45 | 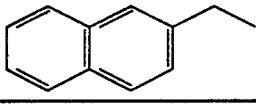 | $C_{33}H_{53}N_3O_4(555); 562 \ (M + Li^+)$ |
| 46 | 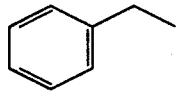 | $C_{38}H_{56}N_2O_4(604); 611 \ (M + Li^+)$ |
TABLE 6
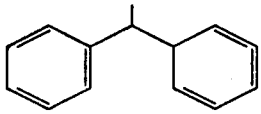
| Ex. | R¹ | MS (FAB,3-NBA/LiCl or LiI) |
|---|---|---|
| 47 | H | $C_{27}H_{48}N_2O_3(448); 455 \ (M+Li^+)$ |
| 48 |  | $C_{34}H_{54}N_2O_3(538); 545 \ (M+Li^+)$ |
| 49 |  | $C_{40}H_{58}N_2O_3(614); 621 \ (M+Li^+)$ |

TABLE 6-continued
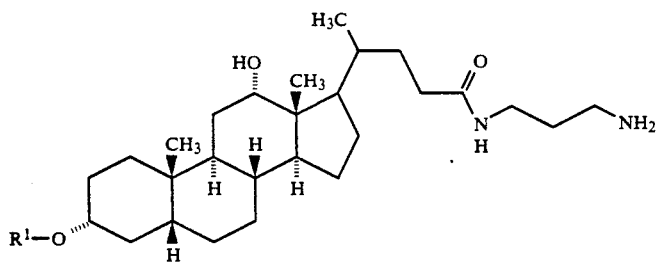
| Ex. | R¹ | MS (FAB,3-NBA/LiCl or LiI) |
|---|---|---|
| 50 | triphenylmethyl | $C_{46}H_{62}N_2O_3$(690); 697 (M+Li$^+$) |
| 51 | 4-chlorobenzyl | $C_{34}H_{53}ClN_2O_3$(572); 579 (M+Li$^+$) |
| 52 | 2,6-dimethylbenzyl | $C_{36}H_{58}N_2O_3$(566); 573 (M+Li$^+$) |
| 53 | 2,4-dichlorobenzyl | $C_{34}H_{52}Cl_2N_2O_3$(606); 613 (M+Li$^+$) |
| 54 | 4-methoxybenzyl | $C_{35}H_{56}N_2O_4$(568); 575 (M+Li$^+$) |
| 55 | 3-pyridylmethyl | $C_{33}H_{53}N_3O_3$(539); 546 (M+Li$^+$) |
| 56 | 2-naphthylmethyl | $C_{38}H_{56}N_2O_3$(588); 595 (M+Li$^+$) |

TABLE 7
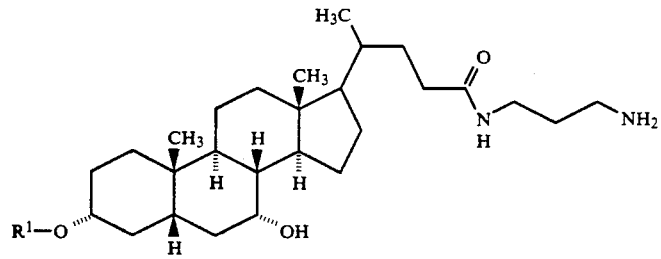
| Ex. | R¹ | MS (FAB,3-NBA/LiCl or LiI) |
|---|---|---|
| 57 | H | $C_{27}H_{48}N_2O_3$(448); 455 (M+Li⁺) |
| 58 | 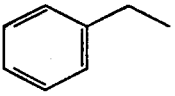 | $C_{34}H_{54}N_2O_3$(538); 545 (M+Li⁺) |
| 59 | 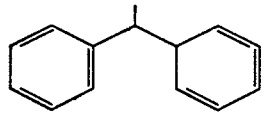 | $C_{40}H_{58}N_2O_3$(614); 621 (M+Li⁺) |
| 60 | 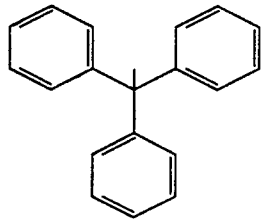 | $C_{46}H_{62}N_2O_3$(690); 697 (M+Li⁺) |
| 61 | 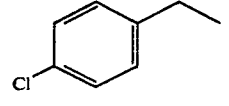 | $C_{34}H_{53}ClN_2O_3$(572); 579 (M+Li⁺) |
| 62 | 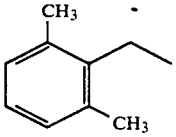 | $C_{36}H_{58}N_2O_3$(566); 573 (M+Li⁺) |
| 63 | 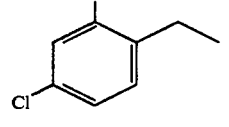 | $C_{34}H_{52}Cl_2N_2O_3$(606); 613 (M+Li⁺) |
| 64 | 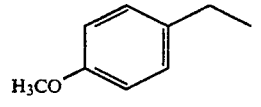 | $C_{35}H_{56}N_2O_4$(568); 575 (M+Li⁺) |
| 65 | 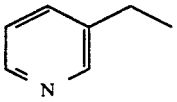 | $C_{33}H_{53}N_3O_3$(539); 546 (M+Li⁺) |
| 66 | 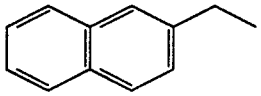 | $C_{38}H_{56}N_2O_3$(588); 595 (M+Li⁺) |

TABLE 8
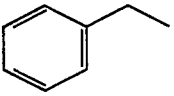
| Ex. | R¹ | MS (FAB,3-NBA/LiCl or LiI) |
|---|---|---|
| 67 | H | $C_{27}H_{48}N_2O_2(432)$; 439 (M+Li⁺) |
| 68 | 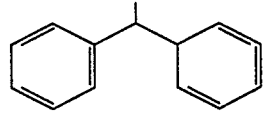 | $C_{34}H_{54}N_2O_2(522)$; 529 (M+Li⁺) |
| 69 | 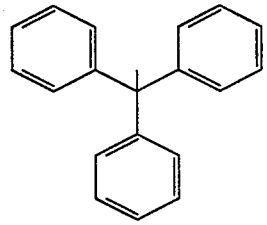 | $C_{40}H_{58}N_2O_2(598)$; 605 (M+Li⁺) |
| 70 | 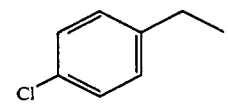 | $C_{46}H_{62}N_2O_2(674)$; 681 (M+Li⁺) |
| 71 | 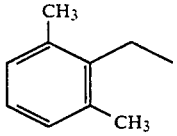 | $C_{34}H_{53}ClN_2O_2(556)$; 563 (M+Li⁺) |
| 72 | 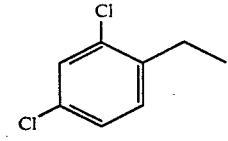 | $C_{36}H_{58}N_2O_2(550)$; 557 (M+Li⁺) |
| 73 | 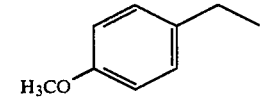 | $C_{34}H_{52}Cl_2N_2O_3(590)$; 597 (M+Li⁺) |
| 74 | 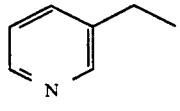 | $C_{35}H_{56}N_2O_3(552)$; 559 (M+Li⁺) |
| 75 | 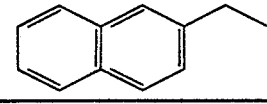 | $C_{33}H_{53}N_3O_2(523)$; 530 (M+Li⁺) |
| 76 |  | $C_{38}H_{56}N_2O_2(572)$; 579 (M+Li⁺) |

The examples of Tables 9 to 12 were obtained in analogy to the examples of Tables 5 to 8.

TABLE 9

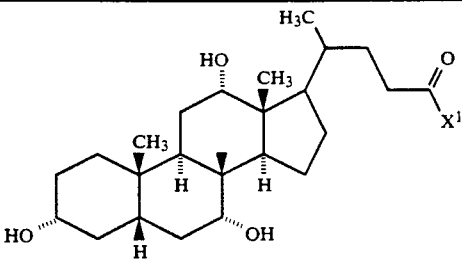

| Example | $X^1$ | MS(FAB,3-NBA/LiCl or LiI) |
|---|---|---|
| 37 | $NH(CH_2)_3NH_2$ | $C_{27}H_{48}N_2O_4(464)$; 471 $(M+Li^+)$ |
| 77 | $NH(CH_2)_4NH_2$ | $C_{28}H_{50}N_2O_4(478)$; 485 $(M+Li^+)$ |
| 78 | $NH(CH_2)_5NH_2$ | $C_{29}H_{52}N_2O_4(492)$; 499 $(M+Li^+)$ |
| 79 | $NH(CH_2)_6NH_2$ | $C_{30}H_{54}N_2O_4(506)$; 513 $(M+Li^+)$ |
| 80 | $NH(CH_2)_7NH_2$ | $C_{31}H_{56}N_2O_4(520)$; 527 $(M+Li^+)$ |
| 81 | $NH(CH_2)_8NH_2$ | $C_{32}H_{58}N_2O_4(534)$; 541 $(M+Li^+)$ |
| 82 | $NH(CH_2)_9NH_2$ | $C_{33}H_{60}N_2O_4(548)$; 555 $(M+Li^+)$ |
| 83 | $NH(CH_2)_{10}NH_2$ | $C_{34}H_{62}N_2O_4(562)$; 569 $(M+Li^+)$ |
| 84 | $NH(CH_2)_{11}NH_2$ | $C_{35}H_{64}N_2O_4(576)$; 583 $(M+Li^+)$ |
| 85 | $NH(CH_2)_{12}NH_2$ | $C_{36}H_{66}N_2O_4(590)$; 597 $(M+Li^+)$ |
| 86 | $NH(CH_2)_2O(CH_2)_2O(CH_2)_2NH_2$ | $C_{30}H_{54}N_2O_6(538)$; 545 $(M+Li^+)$ |
| 87 | $NH(C_6H_4)CH_2(C_6H_4)NH_2$ | $C_{37}H_{52}N_2O_4(588)$; 595 $(M+Li^+)$ |
| 88 | $NH(C_6H_4)O(C_6H_4)NH_2$ | $C_{36}H_{50}N_2O_5(590)$; 597 $(M+Li^+)$ |

TABLE 10

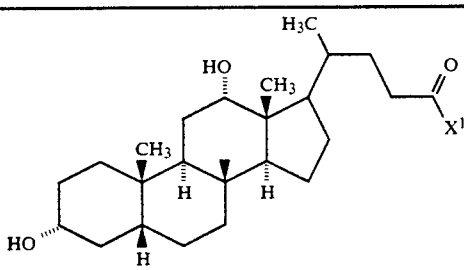

| Example | $X^1$ | MS(FAB,3-NBA/LiCl or LiI) |
|---|---|---|
| 89 | $NH(CH_2)_3NH_2$ | $C_{27}H_{48}N_2O_4(448)$; 4551 $(M+Li^+)$ |
| 90 | $NH(CH_2)_4NH_2$ | $C_{28}H_{50}N_2O_3(462)$; 469 $(M+Li^+)$ |
| 91 | $NH(CH_2)_5NH_2$ | $C_{29}H_{52}N_2O_3(476)$; 483 $(M+Li^+)$ |
| 92 | $NH(CH_2)_6NH_2$ | $C_{30}H_{54}N_2O_3(490)$; 497 $(M+Li^+)$ |
| 93 | $NH(CH_2)_7NH_2$ | $C_{31}H_{56}N_2O_3(504)$; 511 $(M+Li^+)$ |
| 94 | $NH(CH_2)_8NH_2$ | $C_{32}H_{58}N_2O_3(518)$; 525 $(M+Li^+)$ |
| 95 | $NH(CH_2)_9NH_2$ | $C_{33}H_{60}N_2O_3(532)$; 539 $(M+Li^+)$ |
| 96 | $NH(CH_2)_{10}NH_2$ | $C_{34}H_{62}N_2O_3(546)$; 553 $(M+Li^+)$ |
| 97 | $NH(CH_2)_{11}NH_2$ | $C_{35}H_{64}N_2O_3(560)$; 567 $(M+Li^+)$ |

TABLE 10-continued

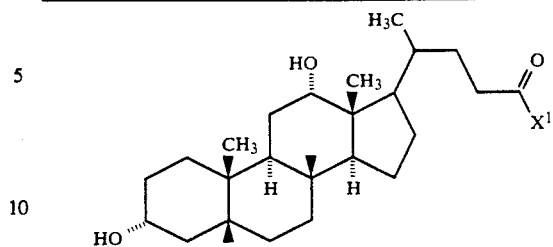

| Example | $X^1$ | MS(FAB,3-NBA/LiCl or LiI) |
|---|---|---|
| 98 | $NH(CH_2)_{12}NH_2$ | $C_{36}H_{66}N_2O_3(574)$; 581 $(M+Li^+)$ |
| 99 | $NH(CH_2)_2O(CH_2)_2O(CH_2)_2NH_2$ | $C_{30}H_{54}N_2O_5(522)$; 529 $(M+Li^+)$ |
| 100 | $NH(C_6H_4)CH_2(C_6H_4)NH_2$ | $C_{37}H_{52}N_2O_3(572)$; 579 $(M+Li^+)$ |
| 101 | $NH(C_6H_4)O(C_6H_4)NH_2$ | $C_{36}H_{50}N_2O_4(574)$; 581 $(M+Li^+)$ |

TABLE 11

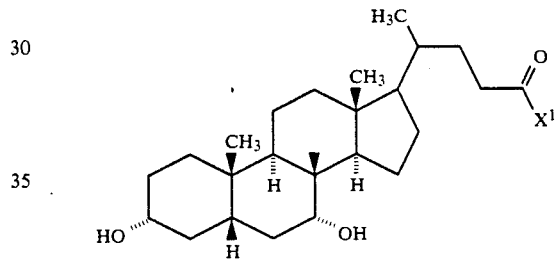

| Example | $X^1$ | MS(FAB,3-NBA/LiCl or LiI) |
|---|---|---|
| 102 | $NH(CH_2)_3NH_2$ | $C_{27}H_{48}N_2O_3(448)$; 455 $(M+Li^+)$ |
| 103 | $NH(CH_2)_4NH_2$ | $C_{28}H_{50}N_2O_3(462)$; 469 $(M+Li^+)$ |
| 104 | $NH(CH_2)_5NH_2$ | $C_{29}H_{52}N_2O_3(476)$; 483 $(M+Li^+)$ |
| 105 | $NH(CH_2)_6NH_2$ | $C_{30}H_{54}N_2O_3(490)$; 497 $(M+Li^+)$ |
| 106 | $NH(CH_2)_7NH_2$ | $C_{31}H_{56}N_2O_3(504)$; 511 $(M+Li^+)$ |
| 107 | $NH(CH_2)_8NH_2$ | $C_{32}H_{58}N_2O_3(518)$; 525 $(M+Li^+)$ |
| 108 | $NH(CH_2)_9NH_2$ | $C_{33}H_{60}N_2O_3(532)$; 539 $(M+Li^+)$ |
| 109 | $NH(CH_2)_{10}NH_2$ | $C_{34}H_{62}N_2O_3(546)$; 553 $(M+Li^+)$ |
| 110 | $NH(CH_2)_{11}NH_2$ | $C_{35}H_{64}N_2O_3(560)$; 567 $(M+Li^+)$ |
| 111 | $NH(CH_2)_{12}NH_2$ | $C_{36}H_{66}N_2O_3(574)$; 581 $(M+Li^+)$ |
| 112 | $NH(CH_2)_2O(CH_2)_2O(CH_2)_2NH_2$ | $C_{30}H_{54}N_2O_5(522)$; 529 $(M+Li^+)$ |
| 113 | $NH(C_6H_4)CH_2(C_6H_4)NH_2$ | $C_{37}H_{52}N_2O_3(572)$; 579 $(M+Li^+)$ |
| 114 | $NH(C_6H_4)O(C_6H_4)NH_2$ | $C_{36}H_{50}N_2O_4(574)$; 581 $(M+Li^+)$ |

TABLE 12

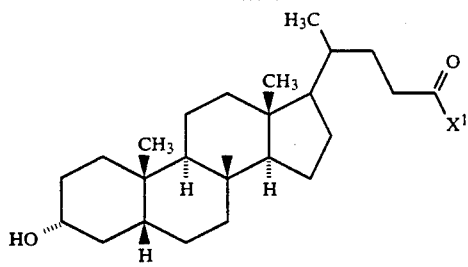

| Example | $X^1$ | MS(FAB,3-NBA/LiCl or LiI) |
|---|---|---|
| 115 | $NH(CH_2)_3NH_2$ | $C_{27}H_{48}N_2O_2$(432); 439 (M+Li$^+$) |
| 116 | $NH(CH_2)_4NH_2$ | $C_{28}H_{50}N_2O_2$(446); 453 (M+Li$^+$) |
| 117 | $NH(CH_2)_5NH_2$ | $C_{29}H_{52}N_2O_2$(460); 467 (M+Li$^+$) |
| 118 | $NH(CH_2)_6NH_2$ | $C_{30}H_{54}N_2O_2$(474); 481 (M+Li$^+$) |
| 119 | $NH(CH_2)_7NH_2$ | $C_{31}H_{56}N_2O_2$(488); 495 (M+Li$^+$) |
| 120 | $NH(CH_2)_8NH_2$ | $C_{32}H_{58}N_2O_2$(502); 509 (M+Li$^+$) |
| 121 | $NH(CH_2)_9NH_2$ | $C_{33}H_{60}N_2O_2$(516); 523 (M+Li$^+$) |
| 122 | $NH(CH_2)_{10}NH_2$ | $C_{34}H_{62}N_2O_2$(530); 537 (M+Li$^+$) |
| 123 | $NH(CH_2)_{11}NH_2$ | $C_{35}H_{64}N_2O_2$(544); 551 (M+Li$^+$) |
| 124 | $NH(CH_2)_{12}NH_2$ | $C_{36}H_{66}N_2O_2$(558); 565 (M+Li$^+$) |
| 125 | $NH(CH_2)_2O(CH_2)_2O(CH_2)_2NH_2$ | $C_{30}H_{54}N_2O_2$(506); 513 (M+Li$^+$) |
| 126 | $NH(C_6H_4)CH_2(C_6H_4)NH_2$ | $C_{37}H_{52}N_2O_2$(556); 563 (M+Li$^+$) |
| 127 | $NH(C_6H_4)O(C_6H_4)NH_2$ | $C_{36}H_{50}N_2O_3$(558); 565 (M+Li$^+$) |

EXAMPLE 128

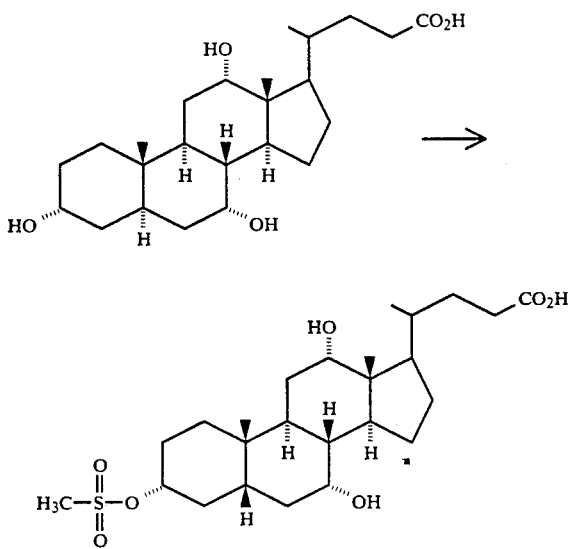

23.1 ml (0.294 mol) of methanesulfonyl chloride were added dropwise at 0° C. to 100 g (0.245 mol) of cholic acid in 500 ml of pyridine. The mixture was stirred at 0° C. for 30 min and at room temperature for 2 h. The mixture was poured into 3000 ml of water/400 ml of conc. $H_2SO_4$ and extracted with ethyl acetate (3×). The combined organic phases were dried with $MgSO_4$ and evaporated. Chromatography on silica gel (ethyl acetate/cyclohexane/HOAc =5:5:1) gave "Example 128" quantitatively. Further purification was not necessary for preparative purposes.

EXAMPLE 129

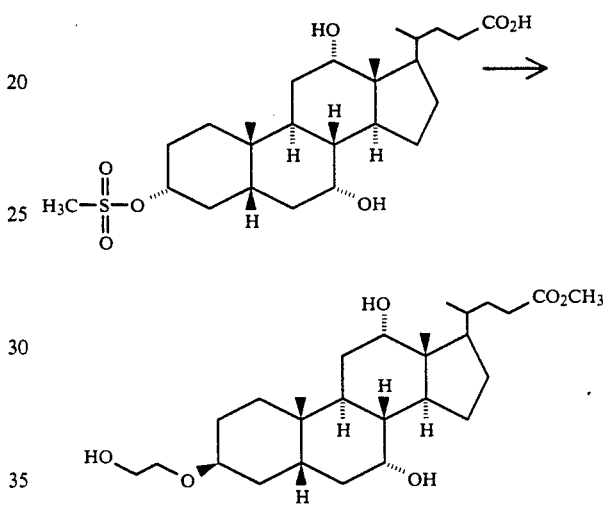

a) 119 g (0.245 mol) of "Example 128, " were heated to 100° C. for 2 h in 500 ml of ethylene glycol/100 ml of pyridine. The mixture was poured into 1500 ml of water/100 ml of conc. $H_2SO_4$ and extracted with ethyl acetate (3×). The combined organic phases were dried ($MgSO_4$) and evaporated.

b) For esterification, the residue was dissolved in 1100 ml of methanolic HCl (prepared by dropwise addition of 100 ml of acetyl chloride to 1000 ml of methanol) and stirred at room temperature overnight. The solution was poured into 2000 ml of water and extracted with ether (3×). The combined organic phases were washed with saturated aqueous $NaHCO_3$ solution and dried ($MgSO_4$). Evaporation of the solvent and flash chromatography on silica gel (ethyl acetate then ethyl acetate/MeOH=10:1) gave 37.1 g (0.08 mol, 33%) of "Example 129".

$C_{27}H_{46}O_6$ (466) MS (FAB, 3-NBA/LiI) : 473 (M+Li$^+$)

The product contains up to 10% of the 3a-isomer, which can optionally be removed by appropriate derivatization.

The compounds of Table 13 were prepared analogously to Example 129. (The β-isomers were predominantly obtained in addition to smaller proportions of the α-isomers).

TABLE 13

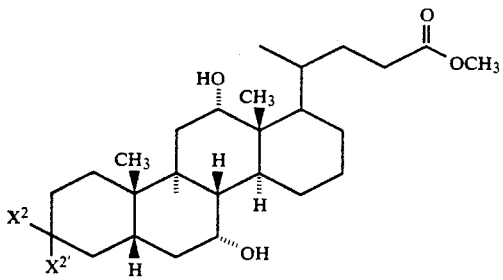

| Example | β-$X^2$ | α-$X^{2'}$ | MS (FAB, 3-NBA/LiJ or LiI) |
|---|---|---|---|
| 130 | HO—(CH$_2$)$_3$—O— | H | $C_{28}H_{48}O_6$ (480); 487 (M + Li$^+$) |
| 131 | HO—(CH$_2$)$_4$—O— | H | $C_{29}H_{50}O_6$ (494); 501 (M + Li$^+$) |
| 132 | HO—(CH$_2$)$_5$—O— | H | $C_{30}H_{52}O_6$ (508); 515 (M + Li$^+$) |
| 133 | HO—(CH$_2$)$_6$—O— | H | $C_{31}H_{54}O_6$ (522); 529 (M + Li$^+$) |
| 134 | HO—(CH$_2$)$_{10}$—O— | H | $C_{35}H_{62}O_6$ (578); 585 (M + Li$^+$) |
|  |  |  | 601 (M + Na$^+$) |
| 135 | HO—(CH$_2$)$_2$—O—(CH$_2$)$_2$—O— | H | $C_{29}H_{50}O_7$ (510); 517 (M + Li$^+$) |
| 136 | H$_3$C—CH—CH$_2$—O—<br>    OH | H | $C_{28}H_{48}O_6$ (480); 487 (M + Li$^+$) |

EXAMPLE 137

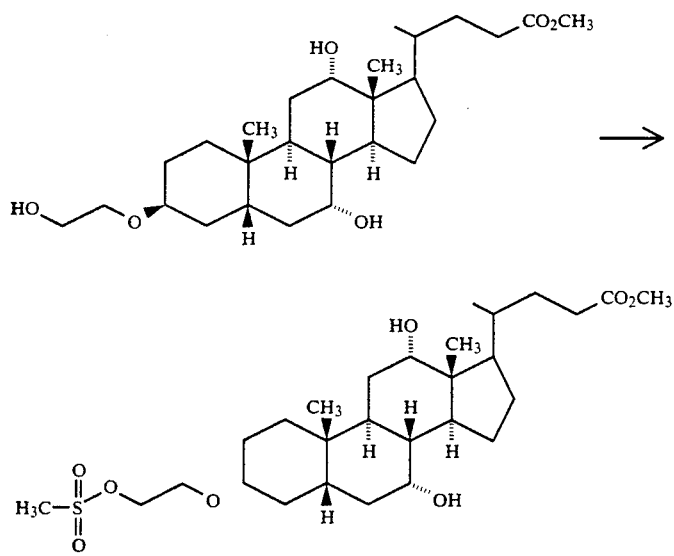

6.6 ml (0.084 mol) of methanesulfonyl chloride were added dropwise at 0° C. to 37.1 g (0.08 mol) of "Example 129," in 150 ml of pyridine. The mixture was stirred at 0° C. for 15 min and at room temperature for 1 h. The reaction mixture was poured into 500 ml of water and extracted with ethyl acetate (3 ×). Drying of the combined organic phases (MgSO$_4$), removal of the solvent and chromatography on silica gel (ethyl acetate/cyclohexane = 3:1) gave 37.7 g (0.07 mol, 87%) of mesylate "Example 137".

$C_{28}H_{48}O_8S$ (544), MS (FAB, 3-NBA/LiI) 551 (M+Li$^+$).

EXAMPLE 138

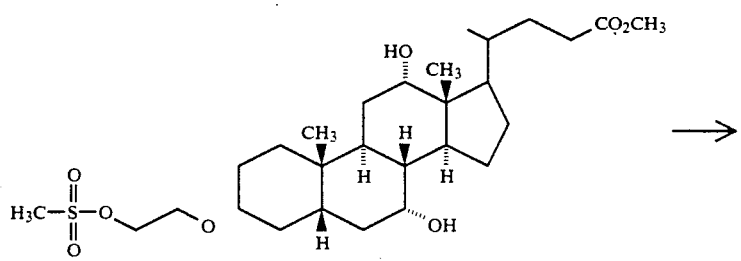

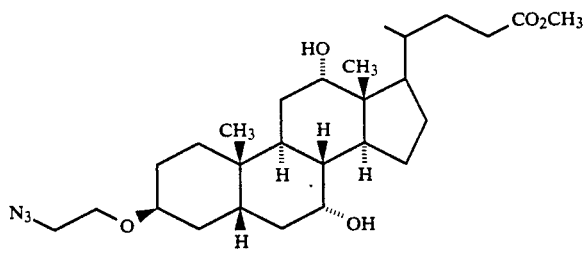

37.7 g (0.07 mol) of mesylate "Example 137" were stirred at 70° C. for 2 h with 4.95 g (0.076 mol) of sodium azide in 150 ml of dry DMF. The reaction mixture was poured into water and extracted with ethyl acetate (3 ×). The combined organic phases were dried (MgSO4) and evaporated. The residue was taken up with toluene and the toluene was removed again in a rotary evaporator (2 ×). Yield 34.5 g of "Example 138" (quantitative). The azide was reacted directly to the next step without further purification.

EXAMPLE 139

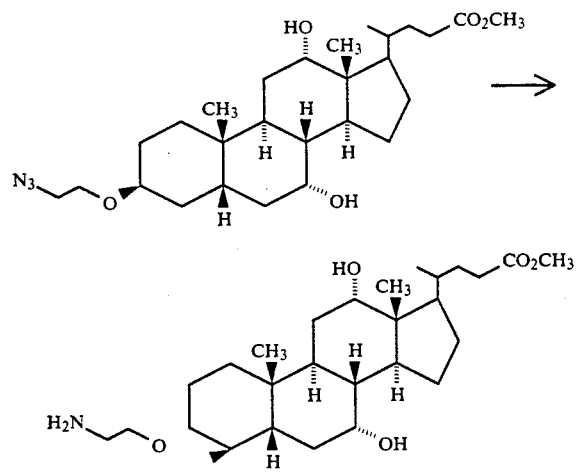

31.1 g (0.063 mol) of "Example 138", were hydrogenated at room temperature and normal pressure with 20 g of Pd/C (10%) in 500 ml of ethyl acetate. The catalyst was filtered off and the filtrate was evaporated. Chromatography on silica gel (ethyl acetate/methanol/-NEt3=5: 1: 1) gave 21.0 g (0.045 mol, 71%) of amine "Example 139". $C_{27}H_{47}NO_5$ (465), MS (FAB, 3-NBA/-LiI): 472 (M+Li+).

The compounds of Table 14 were prepared analogously to Examples 137–139.

TABLE 14

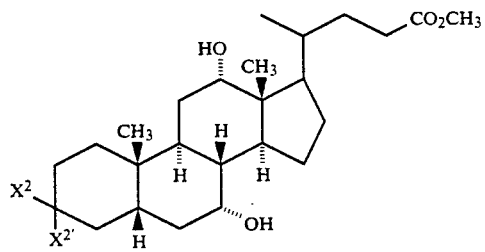

| Example | β-$X^2$ | α-$X^{2'}$ | MS (FAB, 3-NBA/LiI) |
|---|---|---|---|
| 140 | $H_2N-(CH_2)_3-O-$ | H | $C_{28}H_{49}NO_5$ (479); 486 (M + Li+) |
| 141 | $H_2N-(CH_2)_4-O-$ | H | $C_{29}H_{51}NO_5$ (493); 500 (M + Li+) |
| 142 | $H_2N-(CH_2)_5-O-$ | H | $C_{30}H_{53}NO_5$ (507); 514 (M + Li+) |
| 143 | $H_2N-(CH_2)_6-O-$ | H | $C_{31}H_{55}NO_5$ (521); 528 (M + Li+) |
| 144 | $H_2N-(CH_2)_{10}-O-$ | H | $C_{35}H_{63}NO_5$ (577); 584 (M + Li+) |
| 145 | $H_2N-(CH_2)_2-O-(CH_2)_2-O-$ | H | $C_{29}H_{51}NO_6$ (509); 516 (M + Li+) |
| 146 | $H_3C-CH_2-CH_2-O-$<br>$NH_2$ | H | $C_{28}H_{49}NO_5$ (479); 486 (M + Li+) |

In analogy to cholic acid, other bile acids were reacted correspondingly to Examples 128–146 and compounds corresponding to Tables 15–17 were obtained.

a) Starting from deoxycholic acid:

TABLE 15

| Ex. | β-$X^2$ | α-$X^{2'}$ | MS (FAB, 3-NBA/LiI) |
|---|---|---|---|
| 147 | $HO-(CH_2)_2-O-$ | H | $C_{27}H_{46}O_5$ (450); 457 (M + Li+) |
| 148 | $HO-(CH_2)_3-O-$ | H | $C_{28}H_{48}O_5$ (464); 471 (M + Li+) |
| 149 | $HO-(CH_2)_5-O-$ | H | $C_{30}H_{52}O_5$ (492); 499 (M + Li+) |
| 150 | $HO-(CH_2)_{10}-O-$ | H | $C_{35}H_{62}O_5$ (562); 569 (M + Li+) |
| 151 | $H_2N-(CH_2)_2-O-$ | H | $C_{27}H_{47}NO_4$ (449); 456 (M + Li+) |
| 152 | $H_2N-(CH_2)_5-O-$ | H | $C_{30}H_{53}NO_4$ (491); 498 (M + Li+) | b) Starting from chenodeoxycholic acid

TABLE 16

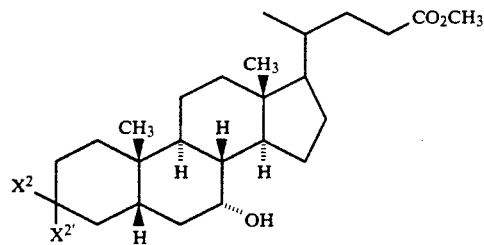

| Ex. | β-$X^2$ | α-$X^{2'}$ | MS (FAB, 3-NBA/LiI) |
|---|---|---|---|
| 153 | HO—(CH$_2$)$_2$—O— | H | C$_{27}$H$_{46}$O$_5$ (450); 457 (M + Li$^+$) |
| 154 | HO—(CH$_2$)$_3$—O— | H | C$_{28}$H$_{48}$O$_5$ (464); 471 (M + Li$^+$) |
| 155 | HO—(CH$_2$)$_5$—O— | H | C$_{30}$H$_{52}$O$_5$ (492); 499 (M + Li$^+$) |
| 156 | HO—(CH$_2$)$_{10}$—O— | H | C$_{35}$H$_{62}$O$_5$ (562); 569 (M + Li$^+$) |
| 157 | H$_2$N—(CH$_2$)$_2$—O— | H | C$_{27}$H$_{47}$NO$_4$ (449); 456 (M + Li$^+$) |
| 158 | H$_2$N—(CH$_2$)$_5$—O— | H | C$_{30}$H$_{53}$NO$_4$ (491); 498 (M + Li$^+$) | c) Starting from lithocholic acid

TABLE 17

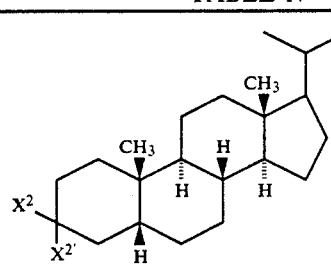

| Ex. | β-$X^2$ | α-$X^{2'}$ | MA (FAB, 3-NBA/LiI) |
|---|---|---|---|
| 159 | HO—(CH$_2$)$_2$—O— | H | C$_{27}$H$_{46}$O$_4$ (434); 441 (M + Li$^+$) |
| 160 | HO—(CH$_2$)$_3$—O— | H | C$_{28}$H$_{48}$O$_4$ (448); 455 (M + Li$^+$) |
| 161 | HO—(CH$_2$)$_5$—O— | H | C$_{30}$H$_{52}$O$_4$ (476); 482 (M + Li$^+$) |
| 162 | HO—(CH$_2$)$_{10}$—O— | H | C$_{35}$H$_{62}$O$_4$ (546); |

TABLE 17-continued

| Ex. | β-$X^2$ | α-$X^{2'}$ | MA (FAB, 3-NBA/LiI) |
|---|---|---|---|
|  |  |  | 653 (M + Li$^+$) |
| 163 | H$_2$N—(CH$_2$)$_2$—O— | H | C$_{27}$H$_{47}$NO$_3$ (433); 440 (M + Li$^+$) |
| 164 | H$_2$N—(CH$_2$)$_5$—O— | H | C$_{30}$H$_{53}$NO$_3$ (475); 482 (M + Li$^+$) |

EXAMPLE 165

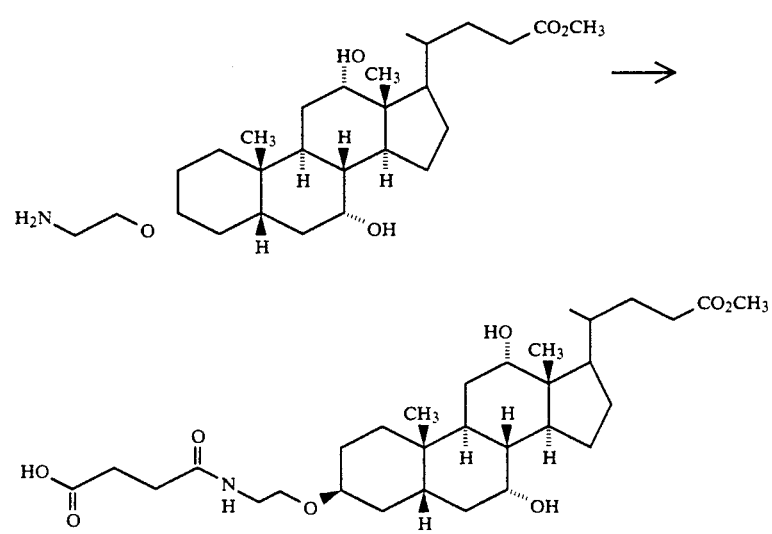

EXAMPLE 124 (X:q=2 and n=2)

2.0 g (4.3 mmol) of "Example 139" were stirred at room temperature for 30 min with 430 mg (4.3 mmol) of succinic anhydride in 25 ml of THP/5 ml of triethylamine. The reaction mixture was poured into 2N HCl and extracted with ethyl acetate (3 ×). Drying of the combined organic phases (MgSO$_4$) and removal of the solvent gave 2.4 g (4.2 mmol, 98%) of "Example 165"

C$_{31}$H$_{51}$NO$_8$ (565) : MS (FAB, 3-NBA/LiI): 578 (M+2Li$^+$-H)

The compound in which q=0, 1, 3 and 5 and n=3 to 18 SiH in the radical X was also prepared.

EXAMPLE 166

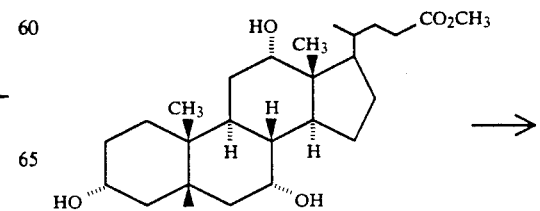

-continued

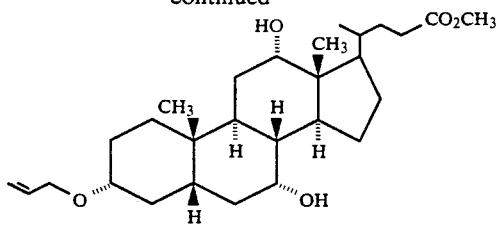

42.2 g (0.1 mol) of methyl cholate, 300 ml (1.8 mol) of N-ethyldiisopropylamine and 10 ml (0. 12 mol) of allyl bromide were heated under reflux for 8 h. A further 5 ml of allyl bromide were in each case added after each hour of reaction time (TLC checking, cyclohexane/ethyl acetate =1:1) . The reaction mixture was poured into 400 ml of conc. $H_2SO_4$/2000 ml of water and extracted with ethyl acetate (3 ×). The combined organic phases were washed once each with 1N HCl, water and saturated $NaHCO_3$ solution. Drying ($MgSO_4$) and removal of the solvent, and chromatography of the residue on silica gel (n-heptane/ethyl acetate=4:1→3:1→2:1) gave 21.91 g (0.047 mol, 47%) of "Example 166".

$C_{28}H_{46}O_5$ (462), MS (FAB, 3-NBA-LiCl): 469 (M+Li$^+$)

EXAMPLE 167

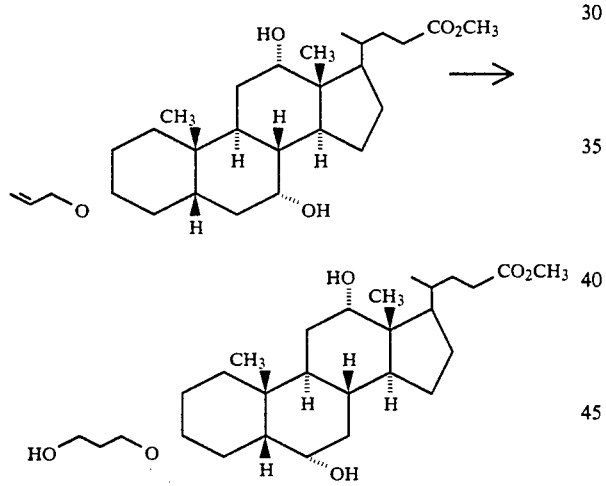

(1) Preparation of thexylborane: 85 ml of 1 molar 2,3-dimethylbutene solution (THP) were added dropwise at 0° C. to 85 ml of 1 molar $BH_3$.THF solution (THF) under an argon atmosphere. The mixture was stirred at 0° C.

(2) Hydroboration: 8.6 g (18.59 mmol) of olefin Example 166 in 25 ml of THF were added dropwise at 0° C. to the solution prepared according to (1). After 3 h at 0° C., the mixture was allowed to come to room temperature (TLC checking). After 16 h at room temperature, freshly prepared thexylborane solution (THF) was added dropwise. The mixture was again stirred at room temperature. After starting material was no longer detectable, the reaction mixture was cautiously transferred to aqueous sodium hydroxide solution under an argon atmosphere with intensive stirring (1 equivalent of NaOH per equivalent of borane). 30 percent hydrogen peroxide solution was then added dropwise with ice-cooling. (2 equivalents per equivalent of borane). After 20 min at 0° C., the mixture was warmed to 50° C. for 30 min. Saturated sodium chloride solution was added for better phase separation. The aqueous phase was extracted with ethyl acetate (2 ×) and the combined organic phases were washed with saturated sodium bisulfite solution (2 ×) and then with a sodium chloride solution (1 ×). Drying with $MgSO_4$, removal of the solvent and chromatography on silica gel (ethyl acetate→ethyl acetate/MeOH=20:1) gave 5.0 g (10.4 mmol, 56%) of "Example 167"

Rf (ethyl acetate): 0.18

$C_{28}H_{48}O_6$ (480) ;(FAB, 3-NBA/LiCl): 487 (M+Li$^+$)

In addition 1.0 g of the secondary alcohol was obtained.

Rf (ethyl acetate): 0.27

EXAMPLE 168

"Example 168" was obtained from Example 167 in analogy to Examples 137-146.

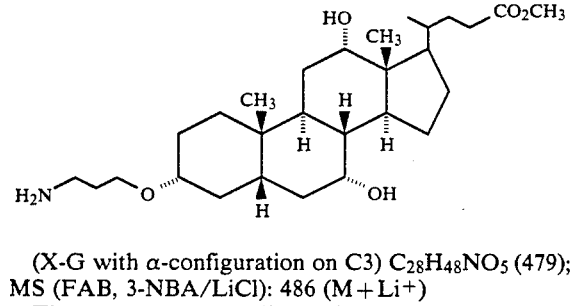

(X-G with α-configuration on C3) $C_{28}H_{48}NO_5$ (479); MS (FAB, 3-NBA/LiCl): 486 (M+Li$^+$)

The compound according to Example 168 was then converted into its dicarboxylic acid monoamide according to Example 165.

Final compound

EXAMPLE 69

Step a)

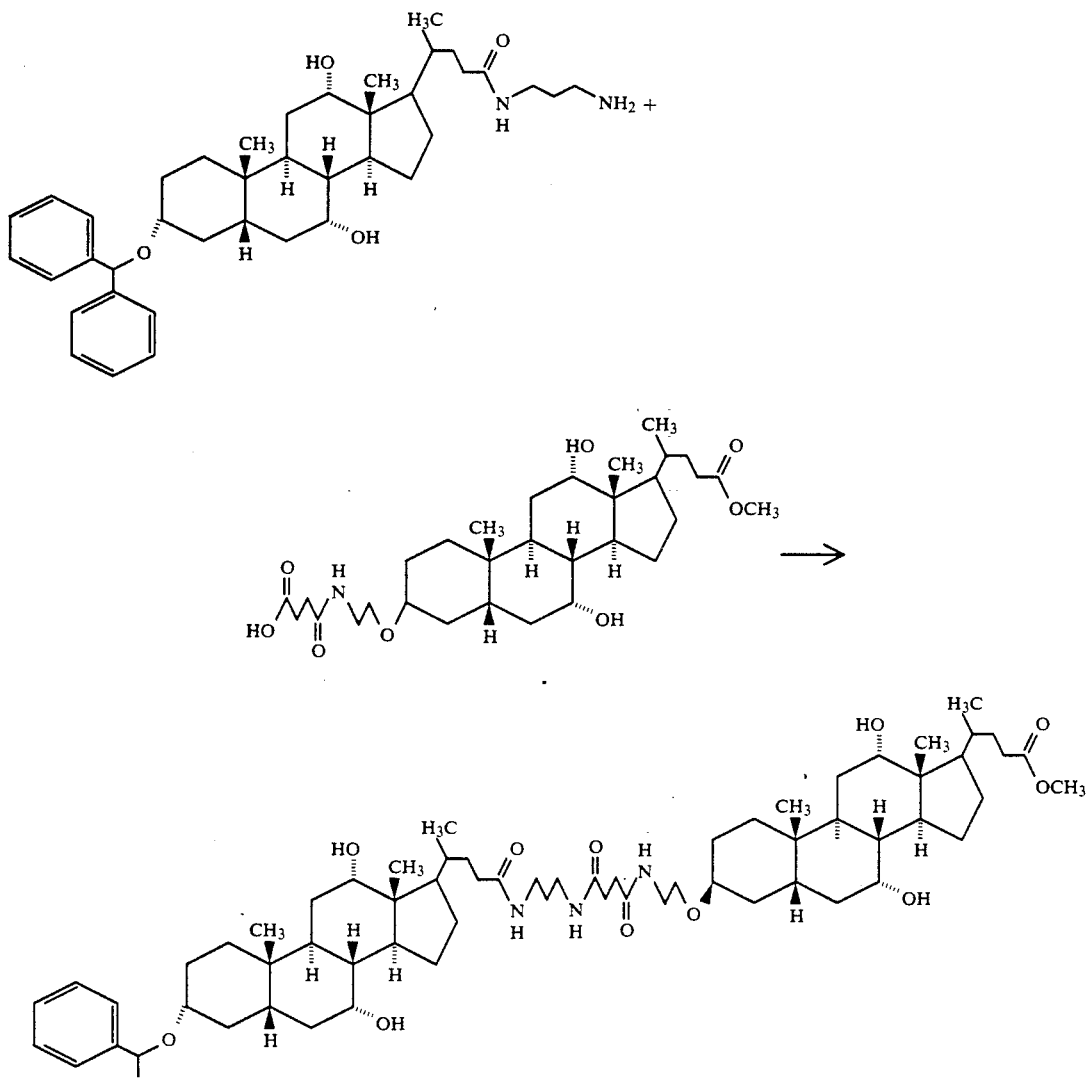

565 mg (1 mmol) of "Example 165", dissolved in 20 ml of tetrahydrofuran and 5 ml of triethylamine, were initially introduced and 96 μl (1 mmol) of ethyl chloroformate was injected at 0° C. The mixture was stirred at 0° C. for 15 minutes, then 630 mg (1 mmol) of "Example 39" were added as a solid. The mixture was stirred at room temperature for 5 h.

The reaction solution was vigorously swirled with 10 ml of 1 molar hydrochloric acid for 10 minutes, then extracted with ethyl acetate (3 ×). The combined organic phases were washed with saturated aqueous NaHCO₃ solution and dried (MgSO₄).

Evaporation of the solvent and flash chromatography on silica gel (ethyl acetate/ethanol=3:1) gave 765 mg (0.65 mmol, 65%) of "Example 169".

$C_7H_{107}N_3O_{11}$ (1177), MS (FAB, 3-NBA-LiCl) 1184 (M+Li⁺)

EXAMPLE 170

Step b) Alkaline hydrolysis

-continued

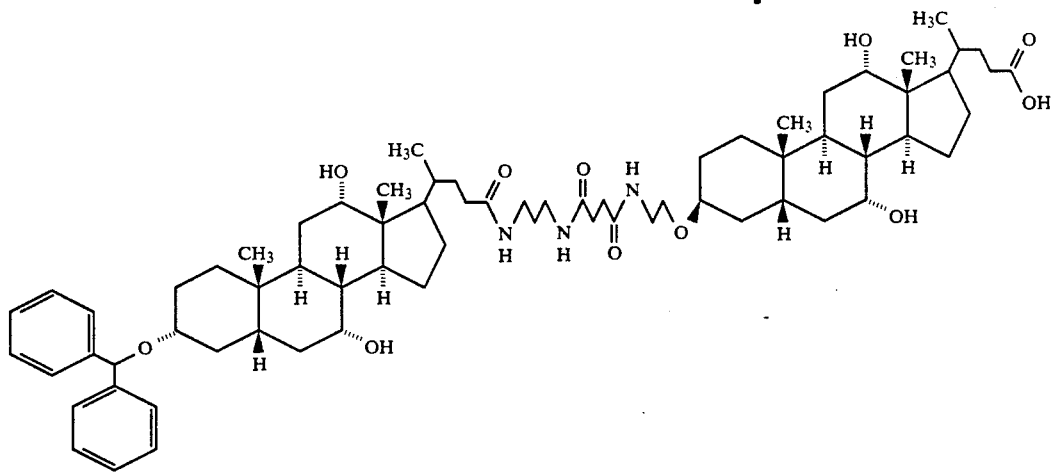

707 mg (0.6 mmol) of "Example 169" were stirred at room temperature for 1.5 h with 10 ml of ethanol and 5 ml of 1 molar sodium hydroxide solution, then intensively swirled for 10 minutes with 10 g of sodium dihydrogen phosphate and extracted (3 ×) with ethyl acetate/ethanol =3:1. The combined organic phases were dried (MgSO$_4$). Evaporation of the solvent, trituration with n-heptane and filtration with suction gave 665 mg (0.57 mmol, 95%) of "Example 170"

$C_{70}H_{105}N_3O_{11}$ (1163), MS (FAB, 3-NBA/LiCl) : 1170 (m+Li$^+$)

The compounds of Table 18 were obtained in analogy to Examples 169 and 170.

TABLE 18

| Ex. | R$^1$ | MS (FAB, 3-NBA/LiCl or LiI) |
|---|---|---|
| 171 | H | $C_{57}H_{95}N_3O_{11}$ (997); 1004 (M + Li$^+$) |
| 172 | (phenethyl) | $C_{64}H_{101}N_3O_{11}$ (1097); 1094 (M + Li$^+$) |
| 173 | (trityl) | $C_{76}H_{109}N_3O_{11}$ (1239); 1246 (M + Li$^+$) |
| 174 | (4-chlorophenethyl) | $C_{64}H_{100}ClN_3O_{11}$ (1121); 1128 (M + Li$^+$) |

TABLE 18-continued
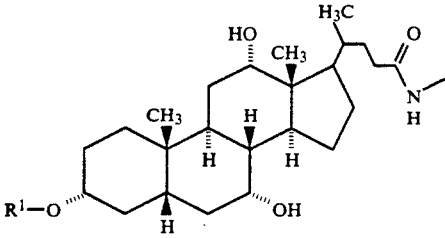
| Ex. | R¹ | MS (FAB, 3-NBA/LiCl or LiI) |
|---|---|---|
| 175 | 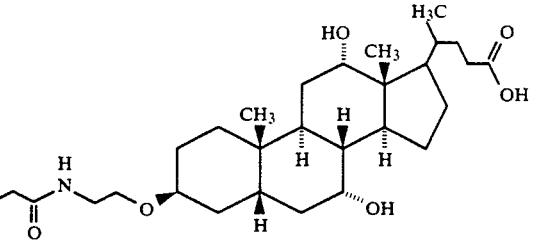 | $C_{66}H_{105}N_3O_{11}$ (1115); 1122 (M + Li⁺) |
| 176 | 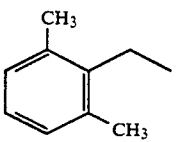 | $C_{65}H_{103}N_3O_{12}$ (1117); 1124 (M + Li⁺) |
| 177 | 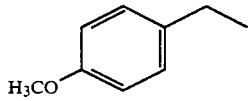 | $C_{64}H_{99}Cl_2N_3O_{11}$ (1155); 1162 (M + Li⁺) |
| 178 | 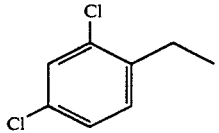 | $C_{63}H_{100}N_4O_{11}$ (1088); 1095 (M + Li⁺) |
| 179 | 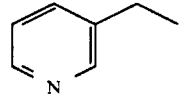 | $C_{68}H_{103}N_3O_{11}$ (1137); 1144 (M + Li⁺) |
The compounds of Table 19 were obtained in analogy to Examples 169 and 170, starting from Example 151.
TABLE 19
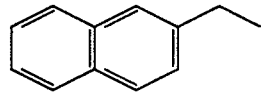
| Ex. | R¹ | MS (FAB, 3-NBA/LiCl or LiI) |
|---|---|---|
| 180 | H | $C_{57}H_{95}N_3O_{10}$ (981); 988 (M + Li⁺) |

TABLE 19-continued

| Ex. | R¹ | MS (FAB, 3-NBA/LiCl or LiI) |
|---|---|---|
| 181 | phenylethyl | $C_{64}H_{101}N_3O_{10}$ (1071); 1078 (M + Li⁺) |
| 182 | triphenylmethyl | $C_{76}H_{109}N_3O_{10}$ (1223); 1230 (M + Li⁺) |
| 183 | 4-chlorophenylethyl | $C_{64}H_{100}ClN_3O_{10}$ (1105); 1112 (M + Li⁺) |
| 184 | 2,6-dimethylphenylethyl | $C_{66}H_{105}N_3O_{10}$ (1099); 1106 (M + Li⁺) |
| 185 | 4-methoxyphenylethyl | $C_{65}H_{103}N_3O_{11}$ (1101); 1108 (M + Li⁺) |
| 186 | 2,4-dichlorophenylethyl | $C_{64}H_{99}Cl_2N_3O_{10}$ (1139); 1146 (M + Li⁺) |
| 187 | 3-pyridylethyl | $C_{63}H_{100}N_4O_{10}$ (1072); 1079 (M + Li⁺) |
| 188 | 2-naphthylethyl | $C_{68}H_{103}N_3O_{10}$ (1121); 1128 (M + Li⁺) |

TABLE 19-continued

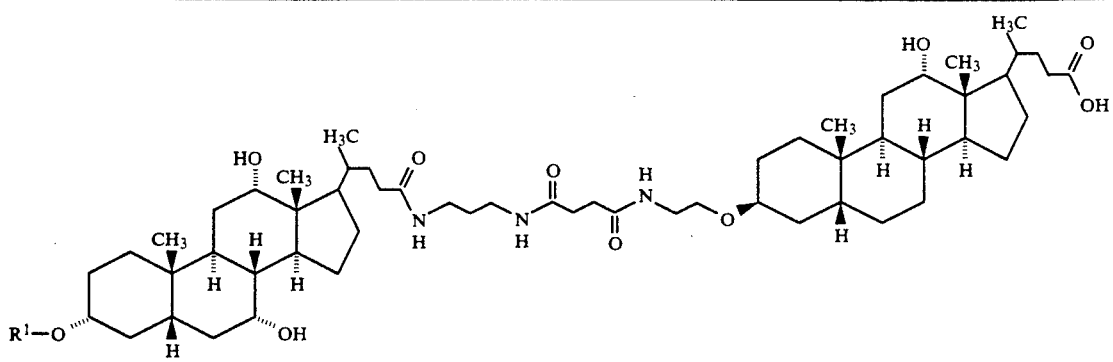

| Ex. | R$^1$ | MS (FAB, 3-NBA/LiCl or LiI) |
|---|---|---|
| 189 | (diphenylmethyl group) | C$_{70}$H$_{105}$N$_3$O$_{10}$ (1147); 1154 (M + Li$^+$) |

The compounds of Table 20 were obtained in analogy to Examples 169 and 170, starting from Example 116.

TABLE 20

| Ex. | R$^1$ | MS (FAB, 3-NBA/LiCl or LiI) |
|---|---|---|
| 190 | H | C$_{57}$H$_{95}$N$_3$O$_{10}$ (981); 988 (M + Li$^+$) |
| 191 | (phenylethyl group) | C$_{64}$H$_{101}$N$_3$O$_{10}$ (1071); 1078 (M + Li$^+$) |
| 192 | (triphenylmethyl group) | C$_{76}$H$_{109}$N$_3$O$_{10}$ (1223); 1230 (M + Li$^+$) |
| 193 | (4-chlorophenylethyl group) | C$_{64}$H$_{100}$ClN$_3$O$_{10}$ (1105); 1112 (M + Li$^+$) |

TABLE 20-continued
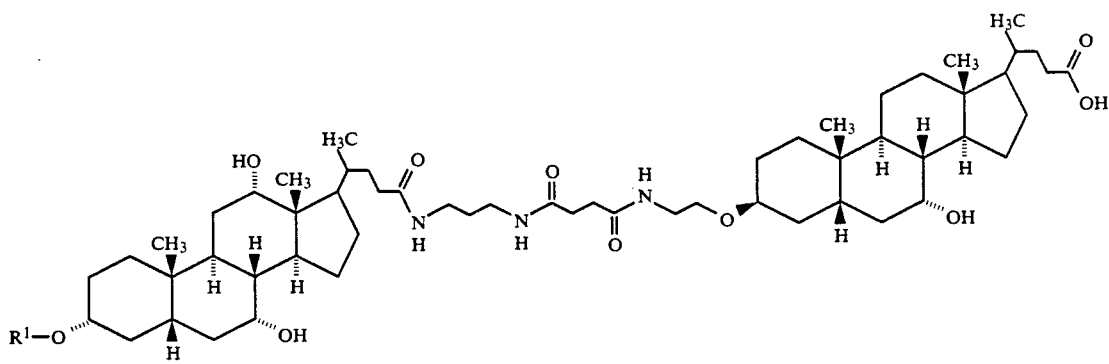
| Ex. | R¹ | MS (FAB, 3-NBA/LiCl or LiI) |
|---|---|---|
| 194 | 2,6-dimethyl-ethylphenyl | $C_{66}H_{105}N_3O_{10}$ (1099); 1106 (M + Li⁺) |
| 195 | 4-methoxy-ethylphenyl | $C_{65}H_{103}N_3O_{11}$ (1101); 1108 (M + Li⁺) |
| 196 | 2,4-dichloro-ethylphenyl | $C_{64}H_{99}Cl_2N_3O_{10}$ (1139); 1146 (M + Li⁺) |
| 197 | 3-ethylpyridyl | $C_{63}H_{100}N_4O_{10}$ (1072); 1079 (M + Li⁺) |
| 198 | 2-ethylnaphthyl | $C_{68}H_{103}N_3O_{10}$ (1121); 1128 (M + Li⁺) |
| 199 | diphenylmethyl | $C_{70}H_{105}N_3O_{10}$ (1147); 1154 (M + Li⁺) |
The compounds of Table 21 were obtained in analogy to Examples 169 and 170, starting from Example 163.

TABLE 21
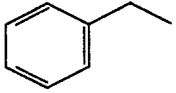
| Ex. | R[1] | MS (FAB,3-NBA/LiCl or LiI) |
|---|---|---|
| 200 | H | $C_{57}H_{95}N_3O_9(965)$; 972 (M+Li$^+$) |
| 201 | 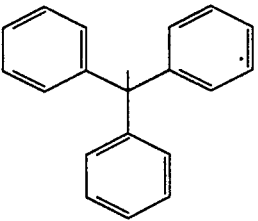 | $C_{64}H_{101}N_3O_9(1055)$; 1062 (M+Li$^+$) |
| 202 | 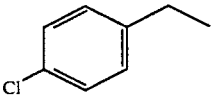 | $C_{76}H_{109}N_3O_9(1207)$; 1214 (M+Li$^+$) |
| 203 | 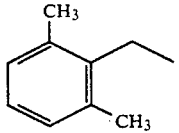 | $C_{64}H_{100}ClN_3O_{10}(1089)$; 1096 (M+Li$^+$) |
| 204 | 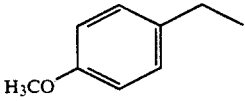 | $C_{66}H_{105}N_3O_9(1083)$; 1090 (M+Li$^+$) |
| 205 | 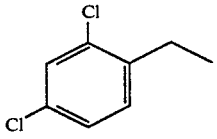 | $C_{65}H_{103}N_3O_{10}(1085)$; 1092 (M+Li$^+$) |
| 206 | 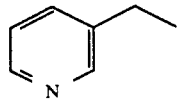 | $C_{64}H_{99}Cl_2N_3O_9(1123)$; 1130 (M+Li$^+$) |
| 207 | 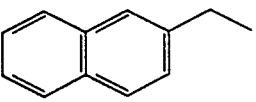 | $C_{63}H_{100}N_4O_9(1056)$; 1063 (M+Li$^+$) |
| 208 |  | $C_{68}H_{103}N_3O_9(1105)$; 1112 (M+Li$^+$) |

TABLE 21-continued
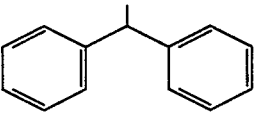
| Ex. | R¹ | MS (FAB,3-NBA/LiCl or LiI) |
|---|---|---|
| 209 | (diphenylmethyl) | $C_{70}H_{105}N_3O_9(1131)$; 1138 (M+Li⁺) |
The compounds of Table 22 were obtained in analogy to Examples 169 and 170.
TABLE 22
| Ex. | R¹ | MS (FAB,3-NBA/LiCl or LiI) |
|---|---|---|
| 210 | H | $C_{57}H_{95}N_3O_{10}(981)$; 988 (M+Li⁺) |
| 211 | (benzyl-CH₂) | $C_{64}H_{101}N_3O_{10}(1071)$; 1078 (M+Li⁺) |
| 212 | (triphenylmethyl) | $C_{76}H_{109}N_3O_{10}(1223)$; 1230 (M+Li⁺) |
| 213 | (4-chlorobenzyl-CH₂) | $C_{64}H_{100}ClN_3O_{10}(1105)$; 1112 (M+Li⁺) |

TABLE 22-continued
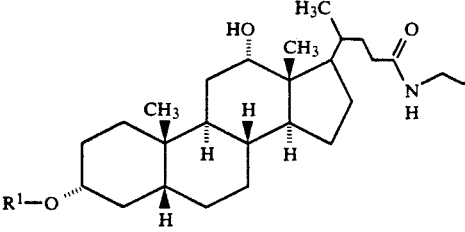
| Ex. | R¹ | MS (FAB,3-NBA/LiCl or LiI) |
|---|---|---|
| 214 | 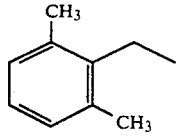 | $C_{66}H_{105}N_3O_{10}$(1099); 1106 (M+Li⁺) |
| 215 | 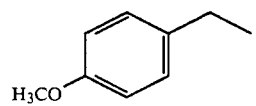 | $C_{65}H_{103}N_3O_{10}$(1101); 1108 (M+Li⁺) |
| 216 | 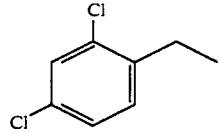 | $C_{64}H_{99}Cl_2N_3O_{10}$(1139); 1146 (M+Li⁺) |
| 217 | 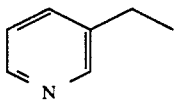 | $C_{63}H_{100}N_4O_{10}$(1072); 1079 (M+Li⁺) |
| 218 | 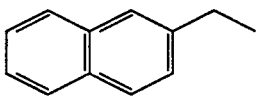 | $C_{68}H_{103}N_3O_{10}$(1121); 1128 (M+Li⁺) |
| 219 | 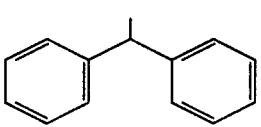 | $C_{70}H_{105}N_3O_{10}$(1147); 1154 (M+Li⁺) |
The compounds of Table 23 were obtained in analogy to Examples 169 and 170.

TABLE 23
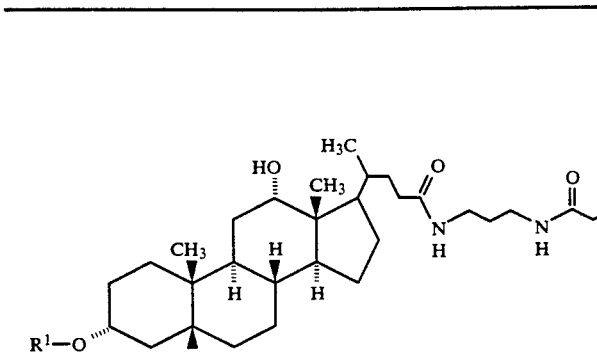
| Ex. | R¹ | MS (FAB,3-NBA/LiCl or LiI) |
|---|---|---|
| 220 | H | $C_{57}H_{95}N_3O_9$(965); 972 (M+Li⁺) |
| 221 | 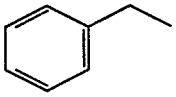 | $C_{64}H_{101}N_3O_9$(1055); 1062 (M+Li⁺) |
| 222 | 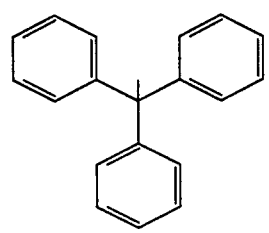 | $C_{76}H_{109}N_3O_9$(1207); 1214 (M+Li⁺) |
| 223 | 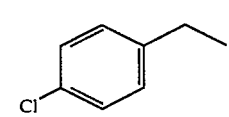 | $C_{64}H_{100}ClN_3O_{10}$(1089); 1096 (M+Li⁺) |
| 224 | 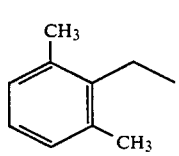 | $C_{66}H_{105}N_3O_9$(1083); 1090 (M+Li⁺) |
| 225 | 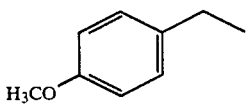 | $C_{65}H_{103}N_3O_{10}$(1085); 1092 (M+Li⁺) |
| 226 | 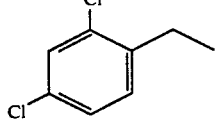 | $C_{64}H_{99}Cl_2N_3O_9$(1123); 1130 (M+Li⁺) |
| 227 | 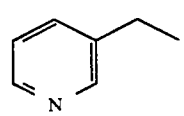 | $C_{63}H_{100}N_4O_9$(1056); 1063 (M+Li⁺) |
| 228 | 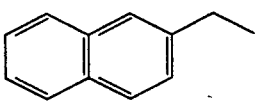 | $C_{68}H_{103}N_3O_9$(1105); 1112 (M+Li⁺) |

TABLE 23-continued
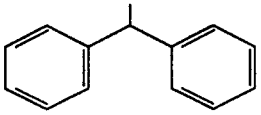
| Ex. | R¹ | MS (FAB,3-NBA/LiCl or LiI) |
|---|---|---|
| 229 | (diphenylmethyl) | $C_{70}H_{105}N_3O_9(1131)$; 1138 (M+Li$^+$) |
The compounds of Table 24 were obtained in analogy to Examples 169 and 170.
TABLE 24
| Ex. | R¹ | MS (FAB,3-NBA/LiCl or LiI) |
|---|---|---|
| 230 | H | $C_{57}H_{95}N_3O_9(965)$; 972 (M+Li$^+$) |
| 231 | (benzyl/phenethyl) | $C_{64}H_{101}N_3O_9(1055)$; 1062 (M+Li$^+$) |
| 232 | (trityl) | $C_{76}H_{109}N_3O_9(1207)$; 1214 (M+Li$^+$) |
| 233 | (4-chlorobenzyl/phenethyl) | $C_{64}H_{100}ClN_3O_9(1089)$; 1096 (M+Li$^+$) |

TABLE 24-continued
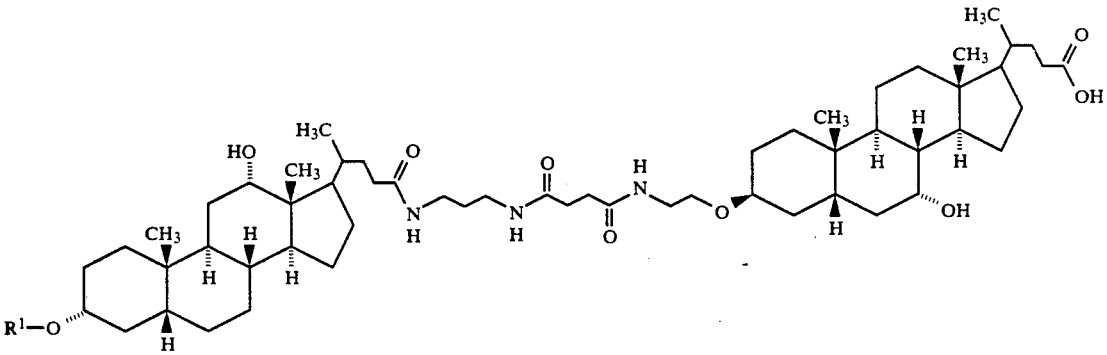
| Ex. | R¹ | MS (FAB,3-NBA/LiCl or LiI) |
|---|---|---|
| 234 | 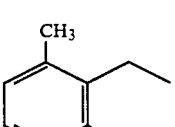 | $C_{66}H_{105}N_3O_9(1083)$; 1090 (M+Li⁺) |
| 235 | 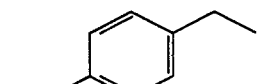 | $C_{65}H_{105}N_3O_{10}(1085)$; 1092 (M+Li⁺) |
| 236 | 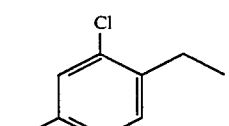 | $C_{64}H_{99}Cl_2N_3O_9(1123)$; 1130 (M+Li⁺) |
| 237 | 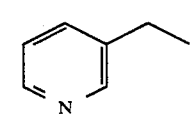 | $C_{63}H_{100}N_4O_9(1056)$; 1063 (M+Li⁺) |
| 238 | 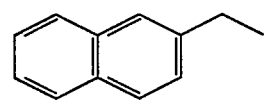 | $C_{68}H_{103}N_3O_9(1105)$; 1112 (M+Li⁺) |
| 239 | 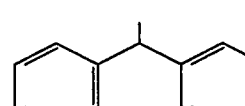 | $C_{70}H_{105}N_3O_9(1131)$; 1138 (M+Li⁺) |
The compounds of Table 25 were obtained in analogy to Examples 169 and 170.

TABLE 25
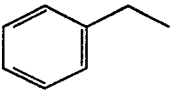
| Ex. | R¹ | MS (FAB,3-NBA/LiCl or LiI) |
|---|---|---|
| 240 | H | $C_{57}H_{95}N_3O_8$(949); 956 (M+Li⁺) |
| 241 | 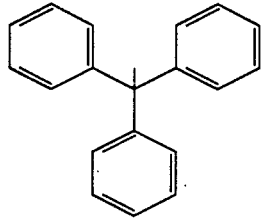 | $C_{64}H_{101}N_3O_8$(1039); 1046 (M+Li⁺) |
| 242 | 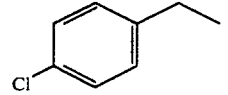 | $C_{76}H_{109}N_3O_8$(1191); 1198 (M+Li⁺) |
| 243 | 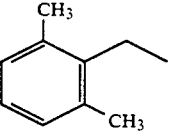 | $C_{64}H_{100}ClN_3O_8$(1073); 1080 (M+Li⁺) |
| 244 | 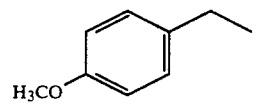 | $C_{66}H_{105}N_3O_8$(1067); 1074 (M+Li⁺) |
| 245 | 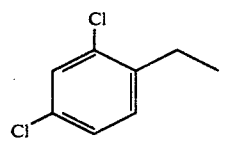 | $C_{65}H_{103}N_3O_9$(1069); 1076 (M+Li⁺) |
| 246 | 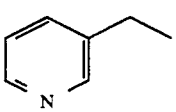 | $C_{64}H_{99}Cl_2N_3O_8$(1107); 1114 (M+Li⁺) |
| 247 | 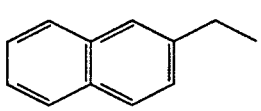 | $C_{63}H_{100}N_4O_8$(1040); 1047 (M+Li⁺) |
| 248 |  | $C_{68}H_{103}N_3O_8$(1089); 1096 (M+Li⁺) |

TABLE 25-continued
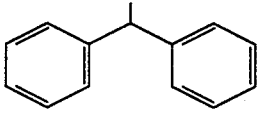
| Ex. | R[1] | MS (FAB,3-NBA/LiCl or LiI) |
|---|---|---|
| 249 | ![diphenylethyl] | $C_{70}H_{105}N_3O_8$(1115); 1122 (M+Li$^+$) |
The compounds of Table 26 were obtained in analogy to Examples 169 and 170.
TABLE 26
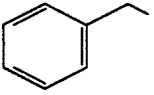
| Ex. | R[1] | MS (FAB, 3-NBA/LiCl or LiI) |
|---|---|---|
| 250 | H | $C_{57}H_{95}N_3O_{10}$(981); 988 (M + Li$^+$) |
| 251 | ![benzyl] | $C_{64}H_{101}N_3O_{10}$(1071); 1078 (M + Li$^+$) |
| 252 | ![trityl] | $C_{76}H_{109}N_3O_{10}$(1223); 1230 (M + Li$^+$) |
| 253 | ![4-chlorobenzyl] | $C_{64}H_{100}ClN_3O_{10}$(1105); 1112 (M + Li$^+$) |

TABLE 26-continued

[Structure: bis-steroid compound with R¹—O— on left steroid and carboxylic acid on right steroid, linked via —NH—C(O)—CH₂CH₂—C(O)—NH—CH₂CH₂—NH—C(O)— type bridge]

| Ex. | R¹ | MS (FAB, 3-NBA/LiCl or LiI) |
|---|---|---|
| 254 | 2,6-dimethylphenyl-CH₂— (with CH₃, CH₃ on ring) | $C_{66}H_{105}N_3O_{10}$(1099); 1106 (M + Li⁺) |
| 255 | 4-methoxyphenyl-CH₂— (H₃CO—) | $C_{65}H_{103}N_3O_{11}$(1101); 1108 (M + Li⁺) |
| 256 | 2,4-dichlorophenyl-CH₂— | $C_{64}H_{99}Cl_2N_3O_{10}$(1139); 1146 (M + Li⁺) |
| 257 | (4-methylpyridin-3-yl)-CH₂— | $C_{63}H_{100}N_4O_{10}$(1072); 1079 (M + Li⁺) |
| 258 | 2-naphthyl-CH₂— | $C_{68}H_{103}N_3O_{10}$(1121); 1128 (M + Li⁺) |
| 259 | diphenylmethyl— | $C_{70}H_{105}N_3O_{10}$(1147); 1154 (M + Li⁺) |

The compounds of Table 27 were obtained in analogy to Examples 169 and 170.

TABLE 27
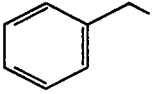
| Ex. | R¹ | MS (FAB, 3-NBA/LiCl or LiI) |
|---|---|---|
| 260 | H | $C_{57}H_{95}N_3O_9(965)$; 972 (M + Li⁺) |
| 261 | 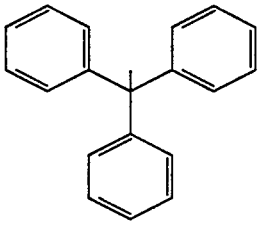 | $C_{64}H_{101}N_3O_9(1055)$; 1062 (M + Li⁺) |
| 262 | 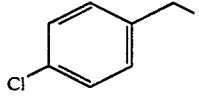 | $C_{76}H_{109}N_3O_9(1207)$; 1214 (M + Li⁺) |
| 263 | 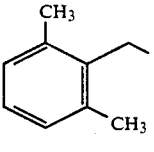 | $C_{64}H_{100}ClN_3O_9(1089)$; 1096 (M + Li⁺) |
| 264 | 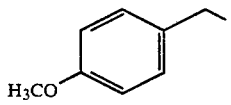 | $C_{66}H_{105}N_3O_9(1083)$; 1090 (M + Li⁺) |
| 265 | 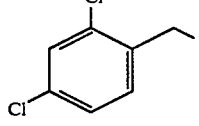 | $C_{65}H_{103}N_3O_{10}(1085)$; 1092 (M + Li⁺) |
| 266 | 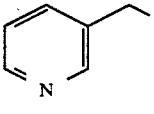 | $C_{64}H_{99}Cl_2N_3O_9(1123)$; 1130 (M + Li⁺) |
| 267 | 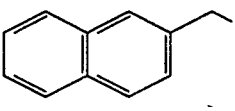 | $C_{63}H_{100}N_4O_9(1056)$; 1063 (M + Li⁺) |
| 268 |  | $C_{68}H_{103}N_3O_9(1105)$; 1112 (M + Li⁺) |

TABLE 27-continued
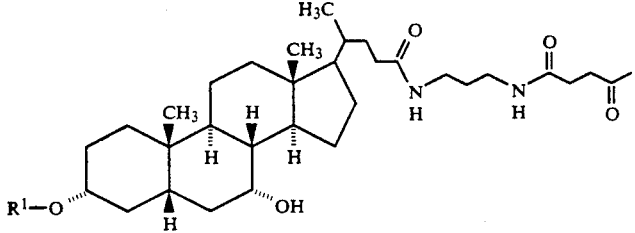
| Ex. | R¹ | MS (FAB, 3-NBA/LiCl or LiI) |
|---|---|---|
| 269 | 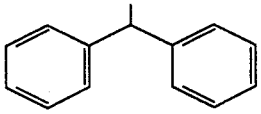 | $C_{70}H_{105}N_3O_9(1105)$; 1112 (M + Li⁺) |
The compounds of Table 28 were obtained in analogy to Examples 169 and 170.
TABLE 28
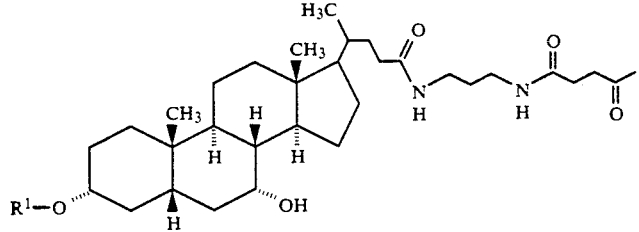
| Ex. | R¹ | MS (FAB, 3-NBA/LiCl or LiI) |
|---|---|---|
| 270 | H | $C_{57}H_{95}N_3O_9(965)$; 972 (M + Li⁺) |
| 271 | 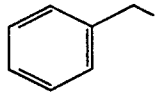 | $C_{64}H_{101}N_3O_9(1055)$; 1062 (M + Li⁺) |
| 272 | 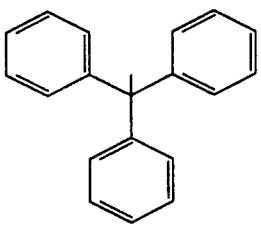 | $C_{76}H_{109}N_3O_9(1207)$; 1214 (M + Li⁺) |
| 273 | 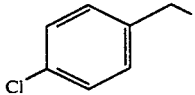 | $C_{64}H_{100}ClN_3O_9(1089)$; 1096 (M + Li⁺) |

TABLE 28-continued
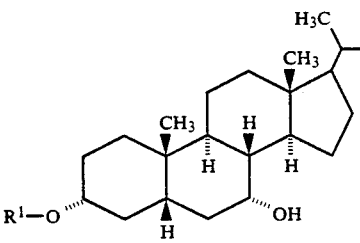
| Ex. | R¹ | MS (FAB, 3-NBA/LiCl or LiI) |
|---|---|---|
| 274 | 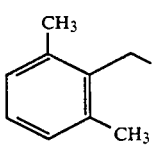 | $C_{66}H_{105}N_3O_9(1083)$; 1090 (M + Li$^+$) |
| 275 | 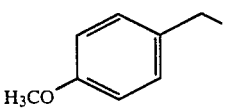 | $C_{65}H_{103}N_3O_{10}(1085)$; 1092 (M + Li$^+$) |
| 276 | 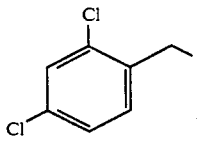 | $C_{64}H_{99}Cl_2N_3O_9(1123)$; 1130 (M + Li$^+$) |
| 277 | 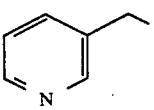 | $C_{63}H_{100}N_4O_9(1056)$; 1063 (M + Li$^+$) |
| 278 | 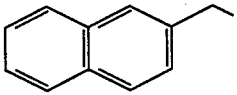 | $C_{68}H_{103}N_3O_9(1105)$; 1112 (M + Li$^+$) |
| 279 | 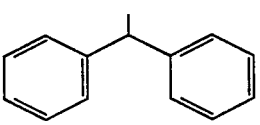 | $C_{70}H_{105}N_3O_9(1131)$; 1138 (M + Li$^+$) |
The compounds of Table 29 were obtained in analogy to Examples 169 and 170.

TABLE 29
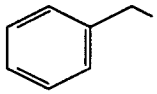
| Ex. | R[1] | MS (FAB, 3-NBA/LiCl OR LiI) |
|---|---|---|
| 280 | H | $C_{57}H_{95}N_3O_8(949)$; 956 (M + Li$^+$) |
| 281 | 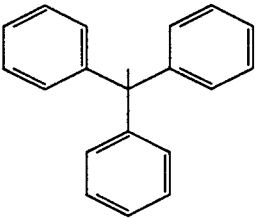 | $C_{64}H_{101}N_3O_8(1039)$; 1046 (M + Li$^+$) |
| 282 | 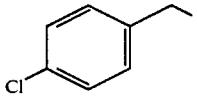 | $C_{76}H_{109}N_3O_8(1191)$; 1198 (M + Li$^+$) |
| 283 | 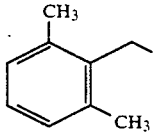 | $C_{64}H_{100}ClN_3O_8(1073)$; 1080 (M + Li$^+$) |
| 284 | 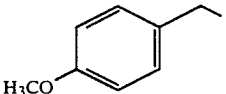 | $C_{66}H_{105}N_3O_8(1067)$; 1074 (M + Li$^+$) |
| 285 | 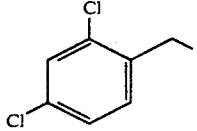 | $C_{65}H_{103}N_3O_9(1069)$; 1076 (M + Li$^+$) |
| 286 | 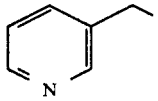 | $C_{64}H_{99}Cl_2N_3O_8(1107)$; 1114 (M + Li$^+$) |
| 287 | 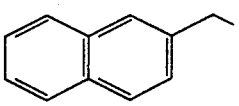 | $C_{63}H_{100}N_4O_8(1040)$; 1047 (M + Li$^+$) |
| 288 |  | $C_{68}H_{103}N_3O_8(1089)$; 1096 (M + Li$^+$) |

TABLE 29-continued
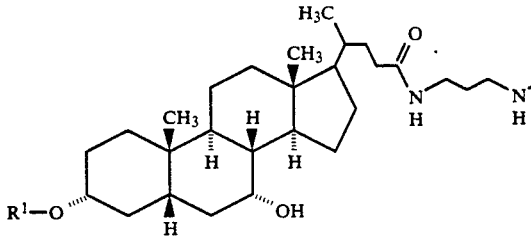
| Ex. | R¹ | MS (FAB, 3-NBA/LiCl OR LiI) |
|---|---|---|
| 289 | 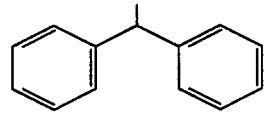 | $C_{70}H_{105}N_3O_8(1115)$; 1122 (M + Li⁺) |
The compounds of Table 30 were obtained in analogy to Examples 169 and 170.
TABLE 30
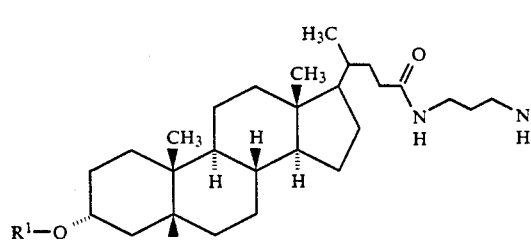
| Ex. | R¹ | MS (FAB, 3-NBA/LiCl or LiI) |
|---|---|---|
| 290 | H | $C_{57}H_{95}N_3O_9(965)$; 972 (M + Li⁺) |
| 291 | 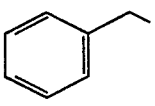 | $C_{64}H_{101}N_3O_9(1055)$; 1062 (M + Li⁺) |
| 292 | 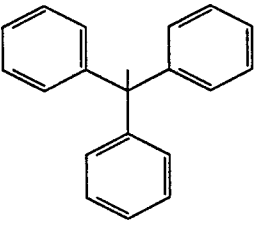 | $C_{76}H_{109}N_3O_9(1207)$; 1214 (M + Li⁺) |
| 293 | 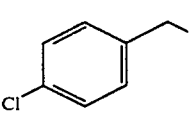 | $C_{64}H_{100}ClN_3O_9(1089)$; 1096 (M + Li⁺) |

TABLE 30-continued

[Chemical structure of steroid-linker-steroid compound with R¹—O substituent]

| Ex. | R¹ | MS (FAB, 3-NBA/LiCl or LiI) |
|---|---|---|
| 294 | 2,6-dimethylphenyl (CH₃, CH₃) | $C_{66}H_{105}N_3O_9$(1083); 1090 (M + Li$^+$) |
| 295 | 4-methoxyphenyl (H₃CO-) | $C_{65}H_{103}N_3O_{10}$(1085); 1092 (M + Li$^+$) |
| 296 | 2,4-dichlorophenyl | $C_{64}H_{99}Cl_2N_3O_9$(1123); 1130 (M + Li$^+$) |
| 297 | 3-pyridyl | $C_{63}H_{100}N_4O_9$(1056); 1063 (M + Li$^+$) |
| 298 | 2-naphthyl | $C_{68}H_{103}N_3O_9$(1105); 1112 (M + Li$^+$) |
| 299 | diphenylmethyl | $C_{68}H_{105}N_3O_9$(1131); 1138 (M + Li$^+$) |

The compounds of Table 31 were obtained in analogy to Examples 169 and 170.

TABLE 31
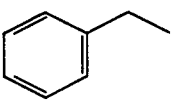
| Ex. | R¹ | MS (FAB,3-NAB/LiCl or LiI) |
|---|---|---|
| 300 | H | $C_{57}H_{95}N_3O_8$(949); 956 (M + Li$^+$) |
| 301 | 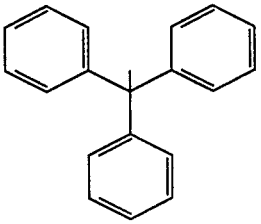 | $C_{64}H_{101}N_3O_8$(1039); 1046 (M + Li$^+$) |
| 302 | 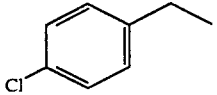 | $C_{76}H_{109}N_3O_8$(1191); 1198 (M + Li$^+$) |
| 303 | 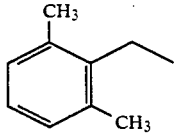 | $C_{64}H_{100}ClN_3O_8$(1073); 1080 (M + Li$^+$) |
| 304 | 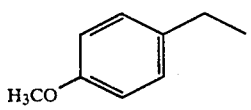 | $C_{66}H_{105}N_3O_8$(1067); 1074 (M + Li$^+$) |
| 305 | 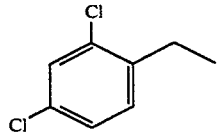 | $C_{65}H_{103}N_3O_9$(1069); 1076 (M + Li$^+$) |
| 306 | 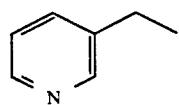 | $C_{64}H_{99}Cl_2N_3O_8$(1107); 1114 (M + Li$^+$) |
| 307 | 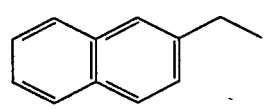 | $C_{63}H_{100}N_4O_8$(1040); 1047 (M + Li$^+$) |
| 308 |  | $C_{68}H_{103}N_3O_8$(1089); 1096 (M + Li$^+$) |

TABLE 31-continued

| Ex. | R¹ | MS (FAB,3-NAB/LiCl or LiI) |
|---|---|---|
| 309 | (diphenylmethyl group) | $C_{70}H_{105}N_3O_8$(1115); 1022 (M + Li$^+$) |

The compounds of Table 32 were obtained in analogy to Examples 169 and 170.

TABLE 32

| Ex. | R¹ | MS (FAB,3-NBA/LiCl or Li) |
|---|---|---|
| 310 | H | $C_{57}H_{95}N_3O_8$(949); 956 (M + Li$^+$) |
| 311 | (benzyl/phenethyl group) | $C_{64}H_{101}N_3O_8$(1039); 1046 (M + Li$^+$) |
| 312 | (triphenylmethyl group) | $C_{76}H_{109}N_3O_8$(1191); 1198 (M + Li$^+$) |
| 313 | (4-chlorobenzyl group) | $C_{64}H_{100}ClN_3O_8$(1073); 1080 (M + Li$^+$) |
| 314 | (2,6-dimethylbenzyl group) | $C_{66}H_{105}N_3O_8$(1067); 1074 (M + Li$^+$) |

TABLE 32-continued

[Structure diagram of bile acid dimer with R¹O- group on left steroid and aldehyde terminus on right steroid, connected via amide-propylene-amide-succinyl-amide-ethyleneoxy linker; right steroid has 7α-OH]

| Ex. | R¹ | MS (FAB,3-NBA/LiCl or Li) |
|---|---|---|
| 315 | 4-ethyl-phenyl-OCH₃ (H₃CO-C₆H₄-CH₂CH₂-) | $C_{65}H_{103}N_3O_9(1069)$; 1076 (M + Li⁺) |
| 316 | 2,4-dichloro-phenyl-ethyl | $C_{64}H_{99}Cl_2N_3O_8(1107)$; 1114 (M + Li⁺) |
| 317 | 3-pyridyl-ethyl | $C_{63}H_{100}N_4O_8(1040)$; 1047 (M + Li⁺) |
| 318 | 2-naphthyl-ethyl | $C_{68}H_{103}N_3O_8(1089)$; 1096 (M + Li⁺) |
| 319 | diphenylmethyl | $C_{70}H_{105}N_3O_8(1115)$; 1122 (M + Li⁺) |

The compounds of Table 33 were obtained in analogy to Examples 169 and 170.

TABLE 33

[Structure diagram similar to Table 32 but right steroid lacks the 7α-OH group]

| Ex. | R¹ | MS (FAB,3-NBA/LiCl or LiI) |
|---|---|---|
| 320 | H | $C_{57}H_{95}N_3O_7(933)$; 940 (M + Li⁺) |

TABLE 33-continued
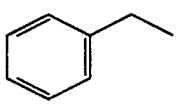
| Ex. | R[1] | MS (FAB,3-NBA/LiCl or LiI) |
|---|---|---|
| 322 | 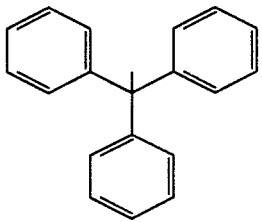 | $C_{64}H_{101}N_3O_7(1023)$; 1030 (M + Li$^+$) |
| 323 | 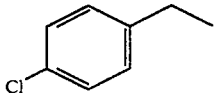 | $C_{76}H_{109}N_3O_7(1171)$; 1082 (M + Li$^+$) |
| 324 | 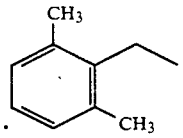 | $C_{64}H_{100}ClN_3O_7(1057)$; 1064 (M + Li$^+$) |
| 325 | 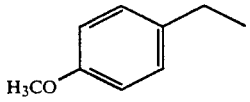 | $C_{66}H_{105}N_3O_7(1051)$; 1058 (M + Li$^+$) |
| 325 | 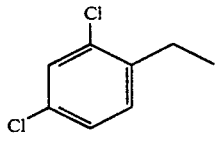 | $C_{65}H_{103}N_3O_8(1053)$; 1060 (M + Li$^+$) |
| 326 | 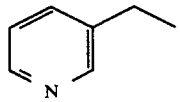 | $C_{64}H_{99}Cl_2N_3O_7(1091)$; 1098 (M + Li$^+$) |
| 327 | 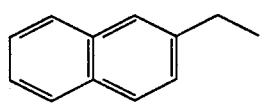 | $C_{63}H_{100}N_4O_7(1024)$; 1031 (M + Li$^+$) |
| 328 |  | $C_{68}H_{103}N_3O_7(1073)$; 1080 (M + Li$^+$) |

TABLE 33-continued

| Ex. | R¹ | MS (FAB,3-NBA/LiCl or LiI) |
|---|---|---|
| 329 | (diphenylmethyl group) | $C_{70}H_{105}N_3O_7(1099)$; 1106 (M + Li$^+$) |

EXAMPLE 330

10 g (17 mmol) of "Example 1" were dissolved in 10 ml of ethanol, 50 ml of 1 molar sodium hydroxide solution were added and the mixture was stirred at room temperature for 2 h, then intensively stirred for 15 minutes with 100 g of sodium dihydrogen phosphate and extracted (3 ×) with ethyl acetate/ethanol=5:1. The combined organic phases were dried (MgSO$_4$).

Evaporation of the solvent, trituration with diisopropyl ether and filtration with suction gave 9.08 g (15.8 mmol, 93%) of "Example 330" $C_{37}H_{50}O_5$ (574), MS (FAB, 2NBA/LiCl): 581 (M+Li$^+$)

The examples of Tables 34-37 were obtained in analogy to Example 330.

TABLE 34

| Example | R¹ | MS (FAB,3-NBA/LiCl or LiI) |
|---|---|---|
| 331 | (benzyl) | $C_{31}H_{46}O_5(498)$; 505 (M + Li$^+$) |
| 332 | (triphenylmethyl) | $C_{43}H_{54}O_5(650)$; 657 (M + Li$^+$) |
| 333 | (4-chlorobenzyl) | $C_{31}H_{45}ClO_5(532)$; 539 (M + Li$^+$) |
| 334 | (2,6-dimethylbenzyl) | $C_{33}H_{50}O_5(526)$; 533 (M + Li$^+$) |
| 335 | (2,4-dichlorobenzyl) | $C_{31}H_{44}Cl_2O_5(566)$; 573 (M + Li$^+$) |

TABLE 34-continued
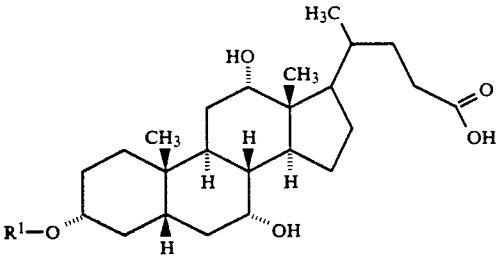
| Example | R¹ | MS (FAB,3-NBA/ LiCl or LiI) |
|---|---|---|
| 336 | 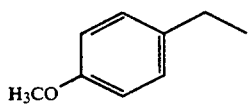 | $C_{32}H_{48}O_6(528)$; 535 (M + Li⁺) |
| 337 | 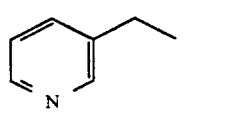 | $C_{30}H_{45}NO_5(499)$; 506 (M + Li⁺) |
| 338 | 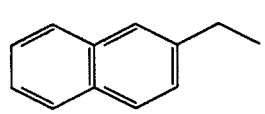 | $C_{35}H_{48}O_5(538)$; 545 (M + Li⁺) |
TABLE 35
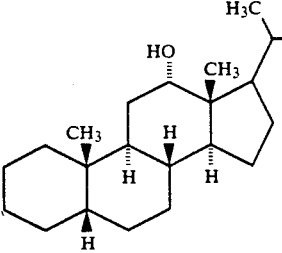
| Example | R¹ | MS (FAB,3-NBA/ LiCl or LiI) |
|---|---|---|
| 339 | 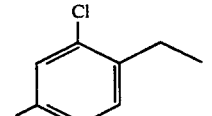 | $C_{31}H_{46}O_4(482)$; 489 (M + Li⁺) |
| 340 | 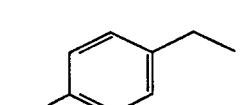 | $C_{43}H_{54}O_4(634)$; 641 (M + Li⁺) |
| 341 | 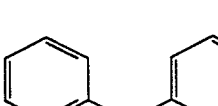 | $C_{31}H_{45}ClO_4(516)$; 523 (M + Li⁺) |
| 342 | 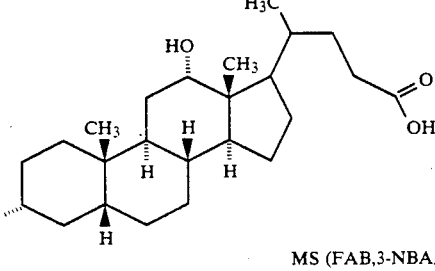 | $C_{33}H_{50}O_4(510)$; 517 (M + Li⁺) |
TABLE 35-continued
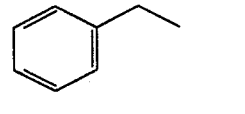
| Example | R¹ | MS (FAB,3-NBA/ LiCl or LiI) |
|---|---|---|
| 343 | 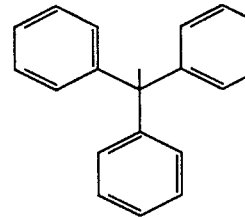 | $C_{31}H_{44}Cl_2O_4(550)$; 557 (M + Li⁺) |
| 344 | 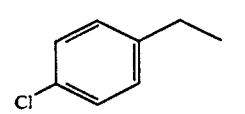 | $C_{32}H_{48}O_5(512)$; 519 (M + Li⁺) |
| 345 | 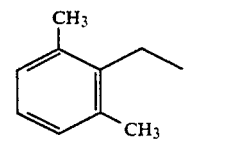 | $C_{30}H_{45}NO_4(483)$; 490 (M + Li⁺) |
| 346 | 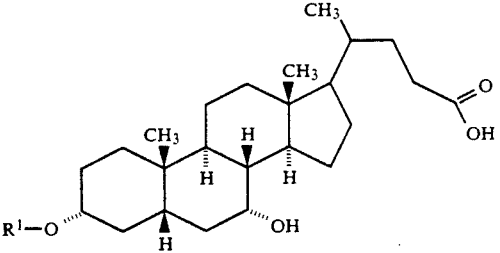 | $C_{35}H_{48}O_4(522)$; 529 (M + Li⁺) |
| 347 | 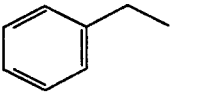 | $C_{37}H_{50}O_4(558)$; 565 (M + Li⁺) |
TABLE 36
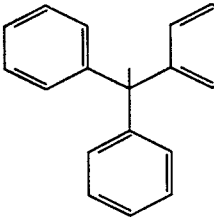
| Example | R¹ | MS (FAB,3-NBA/ LiCl or LiI) |
|---|---|---|
| 348 | 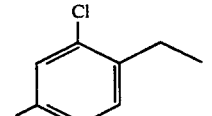 | $C_{31}H_{46}O_4(482)$; 489 (M + Li⁺) |
| 349 | 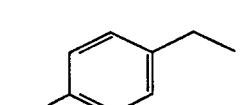 | $C_{43}H_{54}O_4(634)$; 641 (M + Li⁺) |

TABLE 36-continued

[Structure: steroid with R¹—O— at 3α position, 7α-OH, and carboxylic acid side chain]

| Example | R¹ | MS (FAB,3-NBA/LiCl or LiI) |
|---|---|---|
| 350 | 4-chlorophenethyl | C₃₁H₄₅ClO₄(516); 523 (M + Li⁺) |
| 351 | 2,6-dimethylphenethyl | C₃₃H₅₀O₄(510); 517 (M + Li⁺) |
| 352 | 2,4-dichlorophenethyl | C₃₁H₄₄Cl₂O₄(550); 557 (M + Li⁺) |
| 353 | 4-methoxyphenethyl | C₃₂H₄₈O₅(512); 519 (M + Li⁺) |
| 354 | 2,2-diphenylethyl (1,1-diphenylethyl) | C₃₀H₄₅NO₄(483); 490 (M + Li⁺) |
| 355 | 2-(naphth-2-yl)ethyl | C₃₅H₄₈O₄(522); 529 (M + Li⁺) |
| 356 | 2-(pyridin-3-yl)ethyl | C₃₇H₅₀O₄(558); 565 (M + Li⁺) |

TABLE 37

[Structure: steroid with R¹—O— at 3α position and carboxylic acid side chain]

| Example | R¹ | MS (FAB,3-NBA/LiCl or LiI) |
|---|---|---|
| 357 | phenethyl | C₃₁H₄₆O₃(466); 473(M + Li⁺) |
| 358 | 2,2,2-triphenylethyl | C₄₃H₅₄O₃(618); 625(M + Li⁺) |
| 359 | 4-chlorophenethyl | C₃₁H₄₅ClO₃(500); 507(M + Li⁺) |
| 360 | 2,6-dimethylphenethyl | C₃₃H₅₀O₃(494); 501(M + Li⁺) |
| 361 | 2,4-dichlorophenethyl | C₃₁H₄₄Cl₂O₃(534); 541(M + Li⁺) |
| 362 | 4-methoxyphenethyl | C₃₂H₄₈O₄(496); 503(M + Li⁺) |
| 363 | 2-(pyridin-3-yl)ethyl | C₃₀H₄₅NO₃(467); 474(M + Li⁺) |
| 364 | 2-(naphth-2-yl)ethyl | C₃₅H₄₈O₃(506); 513(M + Li⁺) |
| 365 | 2,2-diphenylethyl | C₃₇H₅₀O₃(542); 549(M + Li⁺) |

EXAMPLE 366

Step a

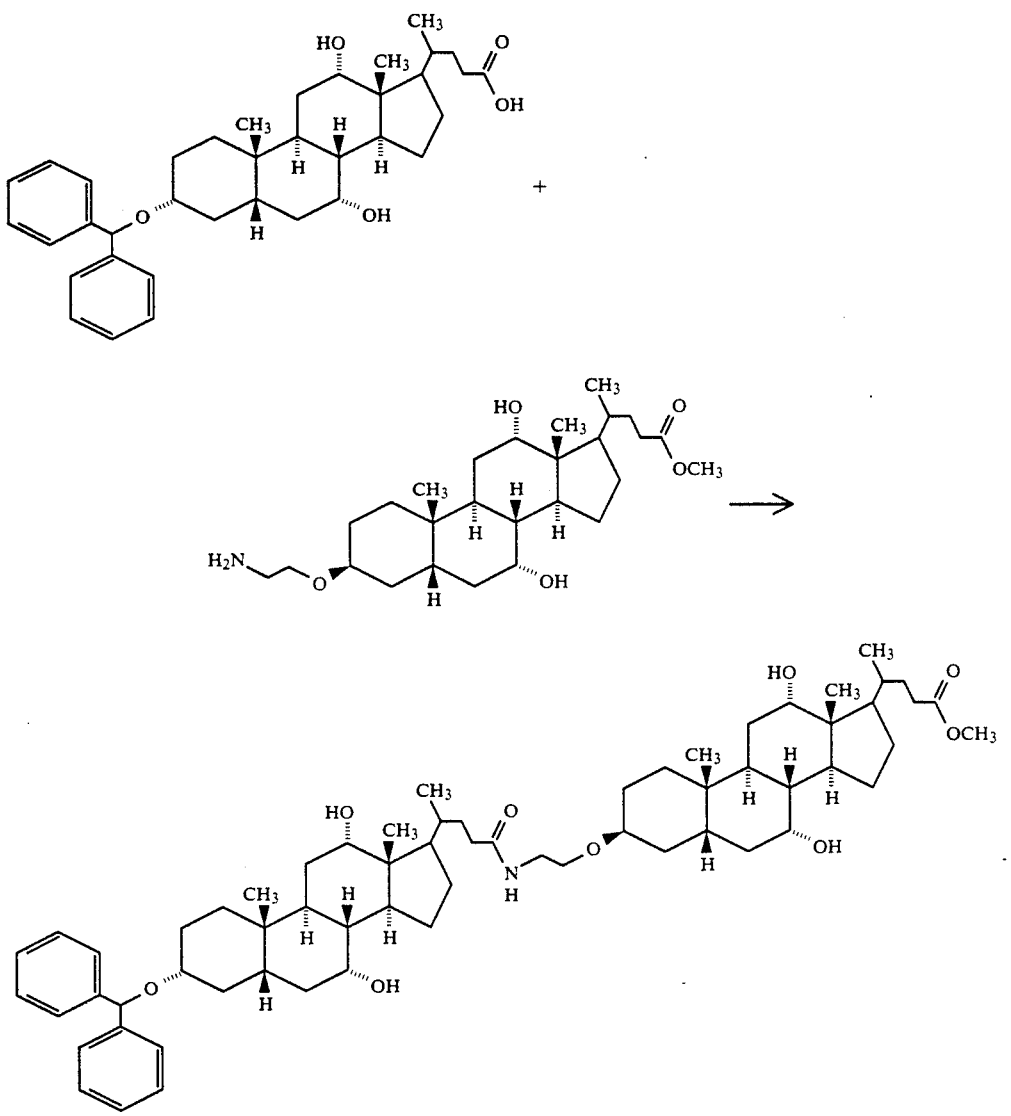

574 mg (1 mmol) of "Example 330", dissolved in 20 ml of tetrahydrofuran and 5 ml of triethylamine, were initially introduced and 108 μl (1.1 nmol) of ethyl chloroformate were injected at 0° C. The mixture was stirred at 0° C. for 15 minutes, then 465 mg (1 mmol) of "Example 139" were added as a solid.

The mixture was stirred at room temperature for 4 h. The reaction solution was swirled vigorously with 10 ml of 1 molar hydrochloric acid for 10 minutes, then extracted with ethyl acetate (3 ×). The combined organic phases were washed with saturated aqueous $NaHCO_3$ solution and dried ($MgSO_4$).

Evaporation of the solvent and flash chromatography on silica gel (ethyl acetate/ethanol=9:1) gave 755 mg (0.74 mmol, 74%) of "Example 366". $C_{84}H_{95}NO_9$ (1021), MS (FAB, 3-NBA/LiCl): 1028 ($M+Li^+$)

Step b) Alkaline hydrolysis

EXAMPLE 367

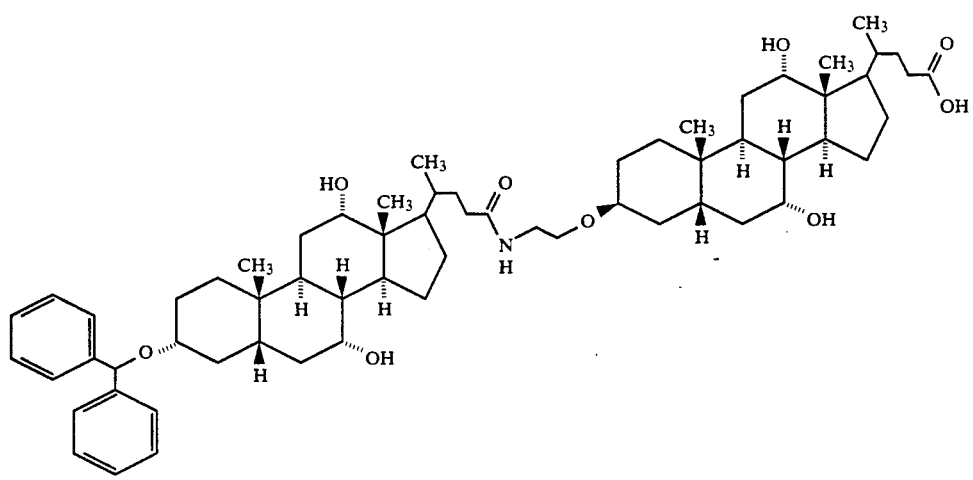

715 mg (0.7 mmol) of "Example 366," were stirred at room temperature for 1.5 h with 10 ml of ethanol and 5 ml of 1 molar sodium hydroxide solution, then intensively swirled for 10 minutes with 10 g of sodium dihydrogen phosphate and extracted (3 ×) with ethyl acetate/ethanol =3:1. The combined organic phases were dried (MgSO$_4$).

Evaporation of the solvent, trituration with diisopropyl ether and filtration with suction gave 670 mg (0.67 mmol, 95%) of "Example 367".

$C_{63}H_{93}NO_9$ (1007), MS (FAB, 3-NBA/LiCl): 1014 (M+Li$^+$)

The compounds of Table 35 were obtained in analogy to is Examples 325 and 326.

EXAMPLE 368

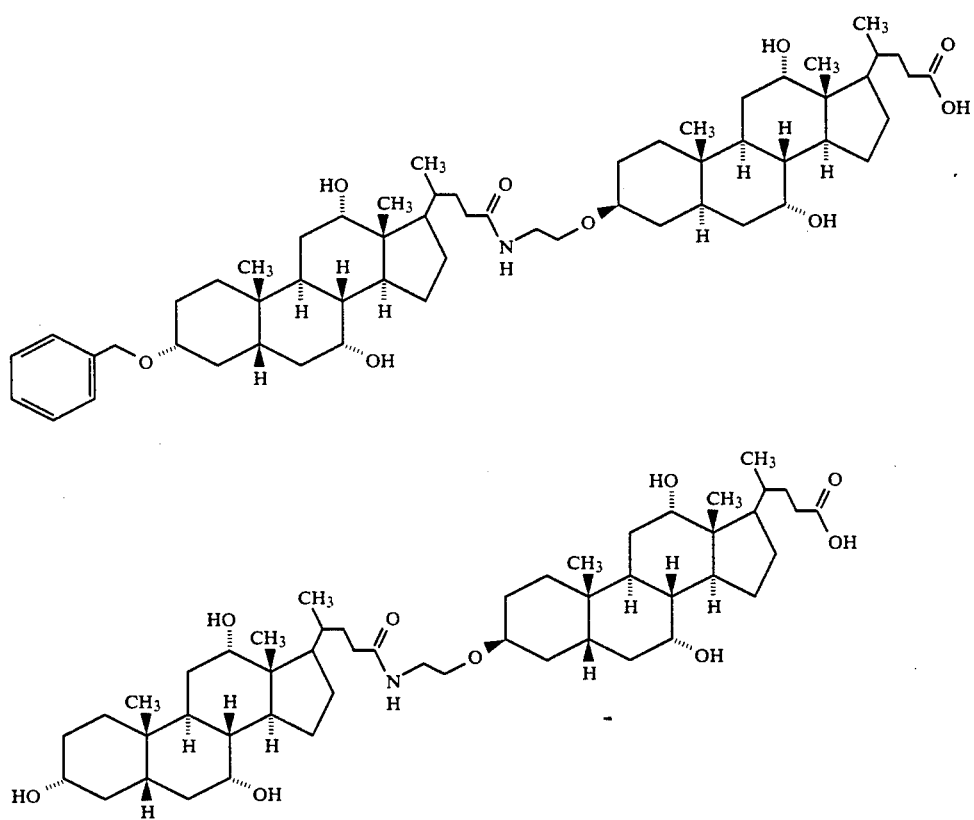

1024 mg (1.1 mmol) of "Example 369" were dissolved in 5 ml of ethanol, 200 mg of palladium on carbon (10%) were added and the mixture was shaken at room temperature under a hydrogen atmosphere for 1 h.

For working-up, the catalyst was filtered off and the filtrate was evaporated. Chromatography on silica gel (ethyl acetate/ethanol=1:1) gave 780 mg (0.92 mmol, 84%) of "Example 368"

$C_{50}H_{83}NO_9$ (841), MS (FAB, 3-NM/LiCl); 848 (M+Li$^+$)

The compounds of Table 38 were obtained in analogy to Examples 366 and 367.

The compounds of Table 39 were obtained in analogy to Examples 366, 367 and 368.

TABLE 38

| Example | R$^1$ | MS (FAB,3-NBA/LiCl or LiI) |
|---|---|---|
| 369 | benzyl (–CH$_2$–C$_6$H$_5$) | C$_{57}$H$_{89}$NO$_9$(931); 938(M + Li$^+$) |
| 370 | trityl (–C(C$_6$H$_5$)$_3$) | C$_{69}$H$_{97}$NO$_9$(1083); 1090(M + Li$^+$) |
| 371 | 4-chlorobenzyl | C$_{57}$H$_{88}$ClNO$_9$(965); 972(M + Li$^+$) |
| 372 | 2,6-dimethylbenzyl | C$_{59}$H$_{93}$NO$_9$(959); 966(M + Li$^+$) |
| 373 | 4-methoxybenzyl | C$_{58}$H$_{91}$NO$_{10}$(961); 968(M + Li$^+$) |
| 374 | 2,4-dichlorobenzyl | C$_{57}$H$_{87}$Cl$_2$NO$_9$(999); 1006(M + Li$^+$) |
| 375 | 3-pyridylmethyl | C$_{56}$H$_{88}$N$_2$O$_9$(932); 939(M + Li$^+$) |
| 376 | 2-naphthylmethyl | C$_{61}$H$_{91}$NO$_9$(981); 988(M + Li$^+$) |

TABLE 39
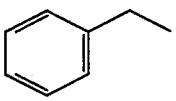
| Example | R[1] | MS (FAB,3-NBA/LiCl or LiI) |
|---|---|---|
| 377 | H | $C_{50}H_{83}NO_8(825)$; 832(M + Li$^+$) |
| 378 | 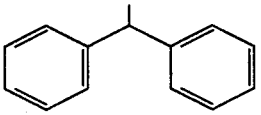 | $C_{57}H_{89}NO_8(915)$; 922(M + Li$^+$) |
| 379 | 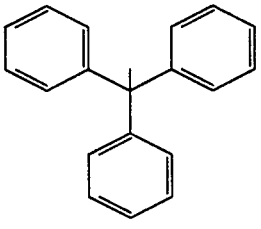 | $C_{63}H_{93}NO_8(991)$; 998(M + Li$^+$) |
| 380 | 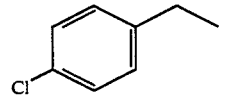 | $C_{69}H_{97}NO_8(1067)$; 1074(M + Li$^+$) |
| 381 | 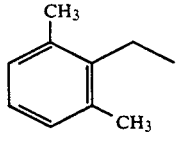 | $C_{57}H_{88}ClNO_8(949)$; 956(M + Li$^+$) |
| 382 | 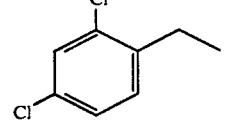 | $C_{58}H_{94}NO_8(943)$; 950(M + Li$^+$) |
| 383 | 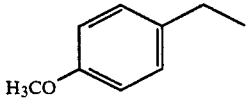 | $C_{57}H_{87}Cl_2NO_8(983)$; 990(M + Li$^+$) |
| 384 | 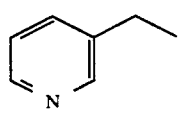 | $C_{58}H_{91}NO_9(945)$; 952(M + Li$^+$) |
| 385 |  | $C_{56}H_{88}N_2O_8(916)$; 923(M + Li$^+$) |

TABLE 39-continued
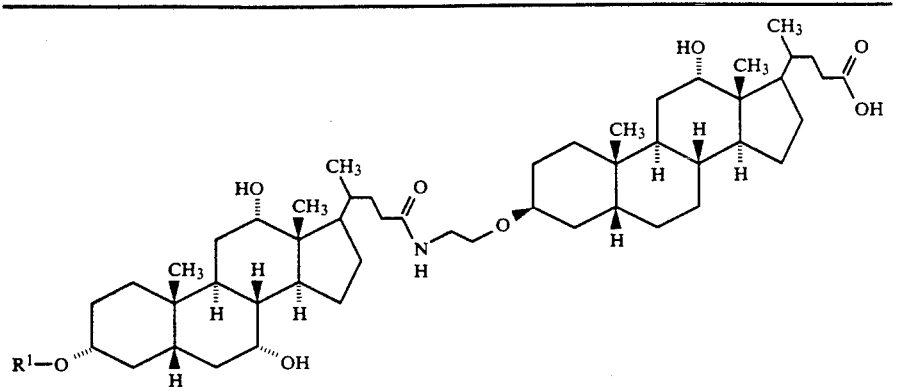
| Example | R¹ | MS (FAB,3-NBA/LiCl or LiI) |
|---|---|---|
| 386 | 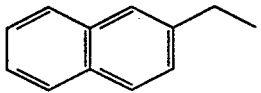 | $C_{61}H_{91}NO_8(965)$; 972(M + Li⁺) |
The compounds of Table 40 were obtained in analogy to Examples 366, 367 and 368.
TABLE 40
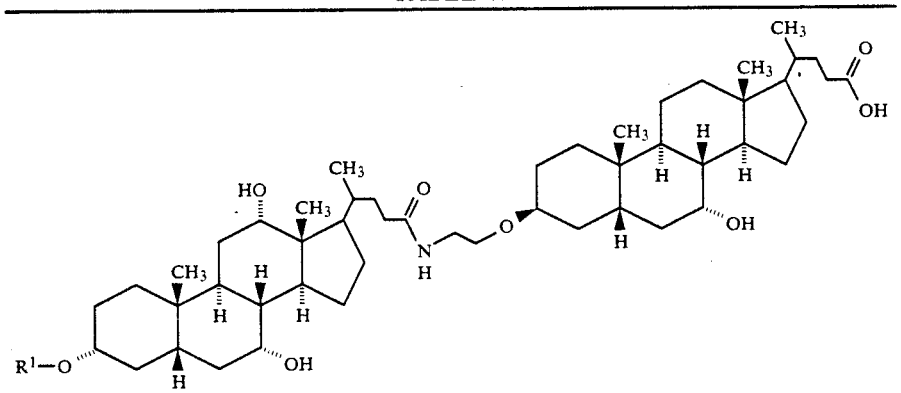
| Example | R¹ | MS (FAB,3-NBA/LiCl or LiI) |
|---|---|---|
| 387 | H | $C_{50}H_{83}NO_8(825)$; 832(M + Li⁺) |
| 388 | 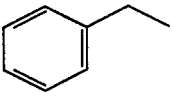 | $C_{57}H_{89}NO_8(915)$; 922(M + Li⁺) |
| 389 | 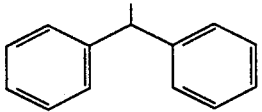 | $C_{63}H_{93}NO_8(991)$; 998(M + Li⁺) |
| 390 | 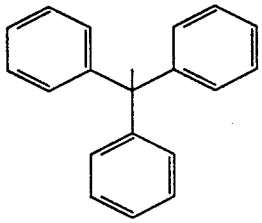 | $C_{69}H_{97}NO_8(1067)$; 1074(M + Li⁺) |

TABLE 40-continued
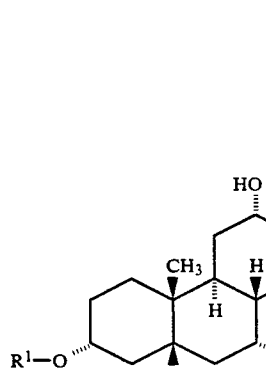
| Example | R[1] | MS (FAB,3-NBA/LiCl or LiI) |
|---|---|---|
| 391 | 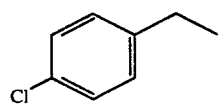 | $C_{57}H_{88}ClNO_8$(949); 956(M + Li$^+$) |
| 392 | 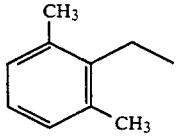 | $C_{59}H_{94}NO_8$(943); 950(M + Li$^+$) |
| 393 | 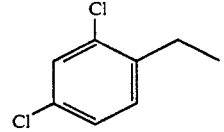 | $C_{57}H_{87}Cl_2NO_8$(983); 990(M + Li$^+$) |
| 394 | 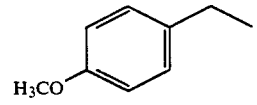 | $C_{58}H_{91}NO_9$(945); 952(M + Li$^+$) |
| 395 | 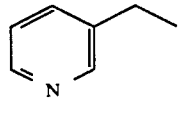 | $C_{56}H_{88}N_2O_8$(916); 923(M + Li$^+$) |
| 396 | 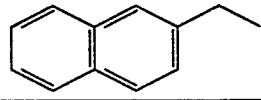 | $C_{61}H_{91}NO_9$(965); 972(M + Li$^+$) |
The compounds of Table 41 were obtained in analogy to Examples 366, 367 and 368.

TABLE 41
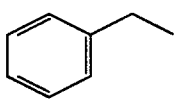
| Example | R¹ | MS (FAB,3-NBA/LiCl or LiI) |
|---------|----|-----|
| 397 | H | $C_{50}H_{83}NO_7(809)$; 816(M + Li⁺) |
| 398 | 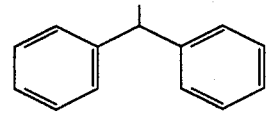 | $C_{57}H_{89}NO_7(899)$; 906(M + Li⁺) |
| 399 | 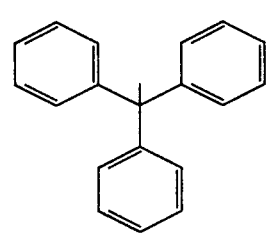 | $C_{63}H_{93}NO_7(975)$; 982(M + Li⁺) |
| 400 | 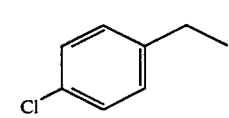 | $C_{69}H_{97}NO_7(1051)$; 1058(M + Li⁺) |
| 401 | 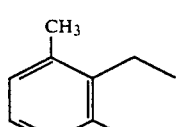 | $C_{57}H_{88}ClNO_7(933)$; 940(M + Li⁺) |
| 402 | 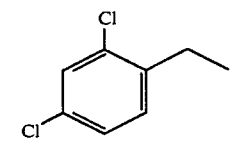 | $C_{59}H_{94}NO_7(927)$; 934(M + Li⁺) |
| 403 | 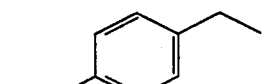 | $C_{57}H_{87}Cl_2NO_7(967)$; 974(M + Li⁺) |
| 404 | 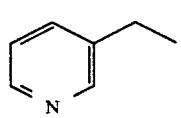 | $C_{58}H_{91}NO_8(929)$; 936(M + Li⁺) |
| 405 |  | $C_{56}H_{88}N_2O_7(900)$; 907(M + Li⁺) |

TABLE 41-continued
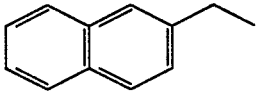
| Example | R[1] | MS (FAB,3-NBA/LiCl or LiI) |
|---|---|---|
| 406 | 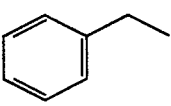 | $C_{61}H_{91}NO_7(949)$; 956(M + Li$^+$) |
The compounds of Table 42 were obtained in analogy to Examples 366, 367 and 368.
TABLE 42
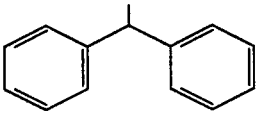
| Example | R[1] | MS (FAB,3-NBA/LiCl or LiI) |
|---|---|---|
| 407 | H | $C_{50}H_{83}NO_8(825)$; 832 (M + Li$^+$) |
| 408 | 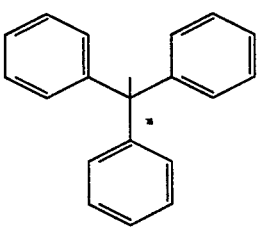 | $C_{57}H_{89}NO_8(915)$; 922 (M + Li$^+$) |
| 409 | 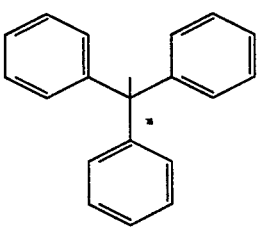 | $C_{63}H_{93}NO_8(991)$; 998 (M + Li$^+$) |
| 410 | 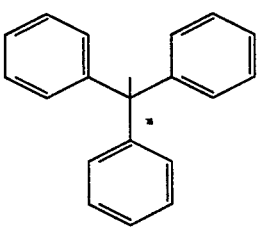 | $C_{69}H_{97}NO_8(1067)$; 1074 (M + Li$^+$) |

TABLE 42-continued
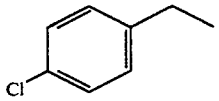
| Example | R¹ | MS (FAB,3-NBA/LiCl or LiI) |
|---|---|---|
| 411 | 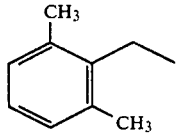 | $C_{57}H_{88}ClNO_8(949); 956 (M + Li^+)$ |
| 412 | 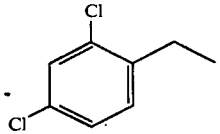 | $C_{59}H_{94}NO_8(943); 950 (M + Li^+)$ |
| 413 | 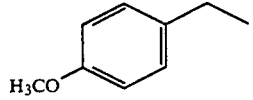 | $C_{57}H_{87}Cl_2NO_8(983); 990 (M + Li^+)$ |
| 414 | 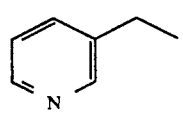 | $C_{58}H_{91}NO_9(945); 952 (M + Li^+)$ |
| 415 | 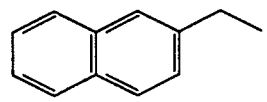 | $C_{56}H_{88}N_2O_8(916); 923 (M + Li^+)$ |
| 416 |  | $C_{61}H_{91}NO_8(965); 972 (M + Li^+)$ |
The compounds of Table 43 were obtained in analogy to Examples 366, 367 and 368.

TABLE 43
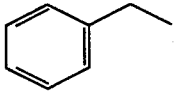
| Example | R¹ | MS (FAB,3-NBA/LiCl or LiI) |
|---------|----|-----------------------------|
| 417 | H | $C_{50}H_{83}NO_7$(809); 816 (M + Li$^+$) |
| 418 | 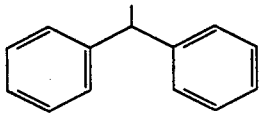 | $C_{57}H_{89}NO_7$(899); 906 (M + Li$^+$) |
| 419 | 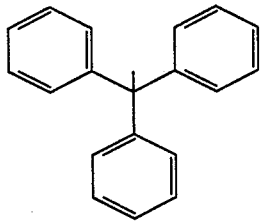 | $C_{63}H_{93}NO_7$(975); 982 (M + Li$^+$) |
| 420 | 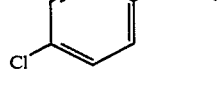 | $C_{69}H_{97}NO_7$(1051); 1058 (M + Li$^+$) |
| 421 | 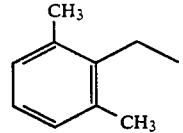 | $C_{57}H_{88}ClNO_7$(933); 940 (M + Li$^+$) |
| 422 | 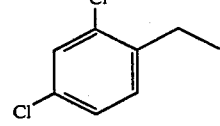 | $C_{59}H_{94}NO_7$(927); 934 (M + Li$^+$) |
| 423 | 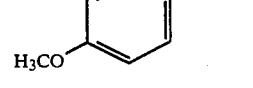 | $C_{57}H_{87}Cl_2NO_7$(967); 974 (M + Li$^+$) |
| 424 | 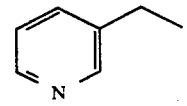 | $C_{58}H_{91}NO_8$(929); 936 (M + Li$^+$) |
| 425 |  | $C_{56}H_{88}N_2O_7$(900); 907 (M + Li$^+$) |

TABLE 43-continued
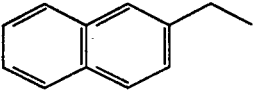
| Example | R¹ | MS (FAB,3-NBA/LiCl or LiI) |
|---|---|---|
| 426 | (2-ethylnaphthalene) | $C_{61}H_{91}NO_7(949)$; 956 (M + Li⁺) |
The compounds of Table 44 were obtained in analogy to Examples 366, 367 and 368.
TABLE 44
| Example | R¹ | MS (FAB,3-NBA/LiCl or LiI) |
|---|---|---|
| 427 | H | $C_{50}H_{83}NO_7(809)$; 816 (M + Li⁺) |
| 428 | (phenethyl) | $C_{57}H_{89}NO_7(899)$; 906 (M + Li⁺) |
| 429 | (diphenylmethyl) | $C_{63}H_{93}NO_7(975)$; 982 (M + Li⁺) |
| 430 | (triphenylmethyl) | $C_{69}H_{97}NO_7(1051)$; 1058 (M + Li⁺) |

TABLE 44-continued
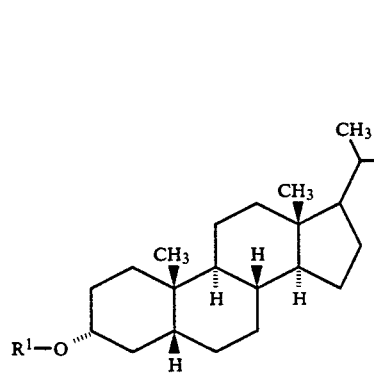
| Example | R¹ | MS (FAB,3-NBA/LiCl or LiI) |
|---|---|---|
| 431 | 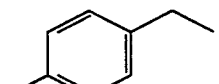 | $C_{57}H_{88}ClNO_7$(933); 940 (M + Li⁺) |
| 432 | 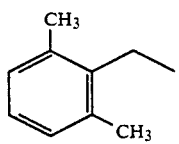 | $C_{59}H_{94}NO_7$(927); 934 (M + Li⁺) |
| 433 | 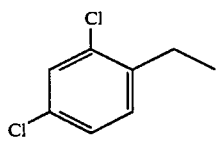 | $C_{57}H_{87}Cl_2NO_7$(967); 974 (M + Li⁺) |
| 434 | 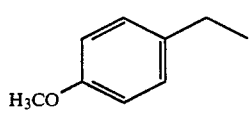 | $C_{58}H_{91}NO_8$(929); 936 (M + Li⁺) |
| 435 | 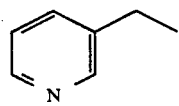 | $C_{56}H_{88}N_2O_7$(900); 907 (M + Li⁺) |
| 436 | 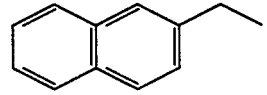 | $C_{61}H_{91}NO_7$(949); 956 (M + Li⁺) |
The compounds of Table 45 were obtained in analogy to Examples 366, 367 and 368.

TABLE 45
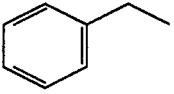
| Example | R¹ | MS (FAB,3-NBA/LiCl or LiI) |
|---|---|---|
| 437 | H | $C_{50}H_{83}NO_6$(793); 800 (M + Li⁺) |
| 438 | 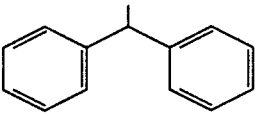 | $C_{57}H_{89}NO_6$(883); 890 (M + Li⁺) |
| 439 | 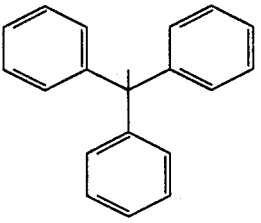 | $C_{63}H_{93}NO_6$(959); 966 (M + Li⁺) |
| 440 | 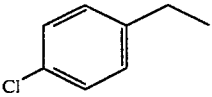 | $C_{69}H_{97}NO_6$(1035); 1042 (M + Li⁺) |
| 441 | 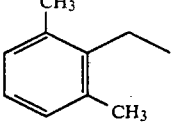 | $C_{57}H_{88}ClNO_6$(917); 924 (M + Li⁺) |
| 442 | 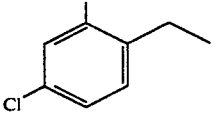 | $C_{59}H_{94}NO_6$(911); 918 (M + Li⁺) |
| 443 | 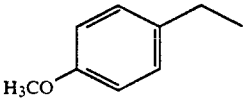 | $C_{57}H_{87}Cl_2NO_6$(951); 958 (M + Li⁺) |
| 444 | 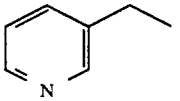 | $C_{58}H_{91}NO_7$(913); 920 (M + Li⁺) |
| 445 |  | $C_{56}H_{88}N_2O_6$(884); 891 (M + Li⁺) |

TABLE 45-continued
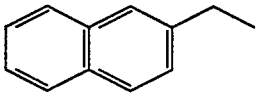
| Example | R¹ | MS (FAB,3-NBA/LiCl or LiI) |
|---|---|---|
| 446 | (2-naphthylethyl) | $C_{61}H_{91}NO_6$(933); 940 (M + Li$^+$) |
The compounds of Table 46 were obtained in analogy to Examples 366, 367 and 368.
TABLE 46
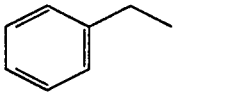
| Example | R¹ | MS (FAB,3-NBA/LiCl or LiI) |
|---|---|---|
| 447 | H | $C_{50}H_{83}NO_9$(825); 832 (M + Li$^+$) |
| 448 | (phenylethyl) | $C_{57}H_{89}NO_8$(915); 922 (M + Li$^+$) |
| 449 | (diphenylmethyl) | $C_{63}H_{93}NO_8$(991); 998 (M + Li$^+$) |
| 450 | (triphenylmethyl) | $C_{69}H_{97}NO_8$(1067); 1074 (M + Li$^+$) |

TABLE 46-continued

[Structure shown: bis-steroid compound with R¹—O— group, linked via amide to ethoxy-steroid bearing HO, OH groups and terminal carboxylic acid]

| Example | R¹ | MS (FAB,3-NBA/LiCl or LiI) |
|---|---|---|
| 451 | 4-chlorobenzyl (CH₂-C₆H₄-Cl) | C$_{57}$H$_{88}$ClNO$_8$(949); 956 (M + Li$^+$) |
| 452 | 2,6-dimethylbenzyl | C$_{59}$H$_{94}$NO$_8$(943); 950 (M + Li$^+$) |
| 453 | 2,4-dichlorobenzyl | C$_{57}$H$_{87}$Cl$_2$NO$_8$(983); 990 (M + Li$^+$) |
| 454 | 4-methoxybenzyl (H₃CO-C₆H₄-CH₂) | C$_{58}$H$_{91}$NO$_9$(945); 952 (M + Li$^+$) |
| 455 | 3-pyridylmethyl | C$_{56}$H$_{88}$N$_2$O$_8$(916); 923 (M + Li$^+$) |
| 456 | 2-naphthylmethyl | C$_{61}$H$_{91}$NO$_8$(965); 972 (M + Li$^+$) |

The compounds of Table 47 were obtained in analogy to Examples 366, 367 and 368.

TABLE 47
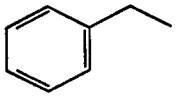
| Example | R¹ | MS (FAB,3-NBA/LiCl or LiI) |
|---|---|---|
| 457 | H | $C_{50}H_{83}NO_7$(809); 816 (M + Li⁺) |
| 458 | 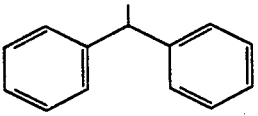 | $C_{57}H_{89}NO_7$(899); 906 (M + Li⁺) |
| 459 | 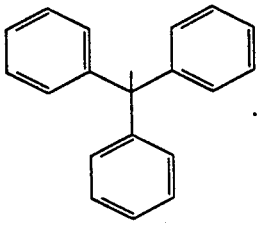 | $C_{63}H_{93}NO_7$(975); 982 (M + Li⁺) |
| 460 | 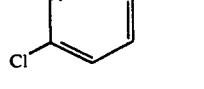 | $C_{69}H_{97}NO_7$(1051); 1058 (M + Li⁺) |
| 461 | 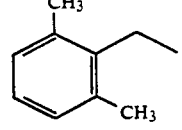 | $C_{57}H_{88}ClNO_7$(933); 940 (M + Li⁺) |
| 462 | 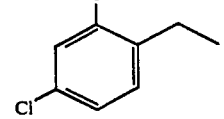 | $C_{59}H_{94}NO_7$(927); 934 (M + Li⁺) |
| 463 | 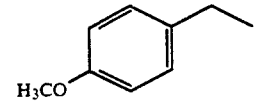 | $C_{57}H_{87}Cl_2NO_7$(967); 974 (M + Li⁺) |
| 464 | 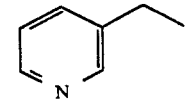 | $C_{58}H_{91}NO_8$(929); 936 (M + Li⁺) |
| 465 |  | $C_{56}H_{88}N_2O_7$(900); 907 (M + Li⁺) |

TABLE 47-continued
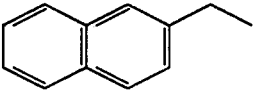
| Example | R¹ | MS (FAB,3-NBA/LiCl or LiI) |
|---|---|---|
| 466 | (2-ethylnaphthyl) | $C_{61}H_{91}NO_7(949); 956 (M + Li^+)$ |
The compounds of Table 48 were obtained in analogy to Examples 366, 367 and 368.
TABLE 48
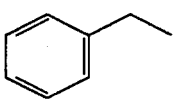
| Example | R¹ | MS (FAB,3-NBA/LiCl or LiI) |
|---|---|---|
| 467 | H | $C_{50}H_{83}NO_7(809); 816 (M + Li^+)$ |
| 468 | (phenethyl) | $C_{57}H_{89}NO_7(899); 906 (M + Li^+)$ |
| 469 | (diphenylmethyl) | $C_{63}H_{93}NO_7(975); 982 (M + Li^+)$ |
| 470 | (triphenylmethyl) | $C_{69}H_{97}NO_7(1051); 1058 (M + Li^+)$ |

TABLE 48-continued
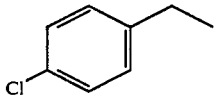
| Example | R[1] | MS (FAB,3-NBA/LiCl or LiI) |
|---|---|---|
| 471 | 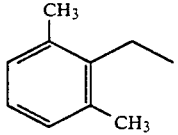 | C$_{57}$H$_{88}$ClNO$_7$(933); 940 (M + Li$^+$) |
| 472 | 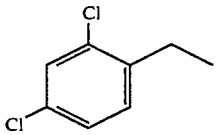 | C$_{59}$H$_{94}$NO$_7$(927); 934 (M + Li$^+$) |
| 473 | 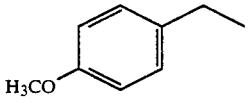 | C$_{57}$H$_{87}$Cl$_2$NO$_7$(967); 974 (M + Li$^+$) |
| 474 | 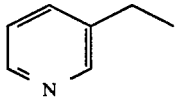 | C$_{58}$H$_{91}$NO$_8$(929); 936 (M + Li$^+$) |
| 475 | 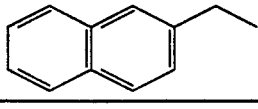 | C$_{56}$H$_{88}$N$_2$O$_7$(900); 907 (M + Li$^+$) |
| 476 | | C$_{61}$H$_{91}$NO$_7$(949); 956 (M + Li$^+$) |
The compounds of Table 49 were obtained in analogy to Examples 366, 367 and 368.

TABLE 49
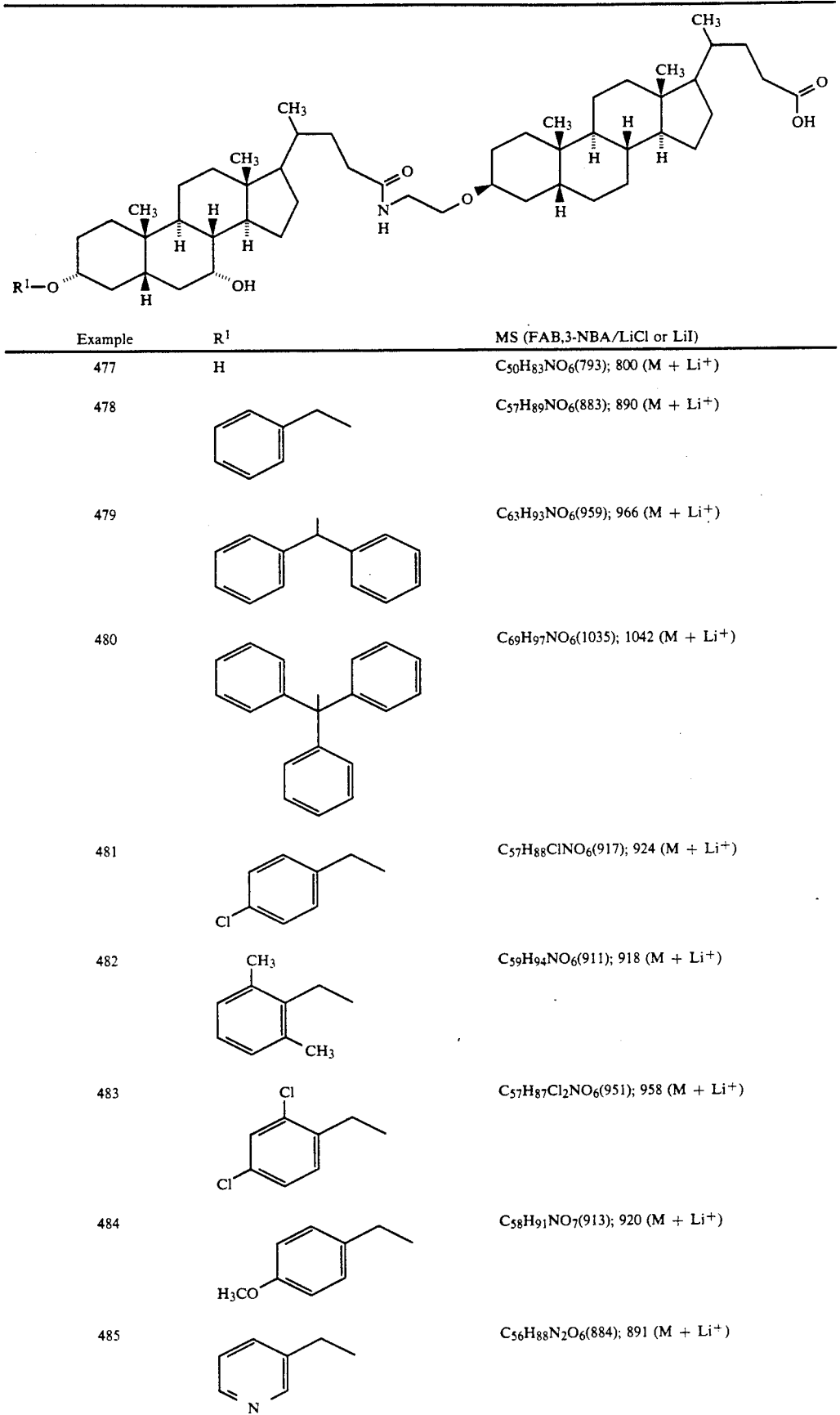
| Example | R[1] | MS (FAB,3-NBA/LiCl or LiI) |
|---|---|---|
| 477 | H | $C_{50}H_{83}NO_6(793)$; 800 (M + Li$^+$) |
| 478 | ![phenyl-ethyl] | $C_{57}H_{89}NO_6(883)$; 890 (M + Li$^+$) |
| 479 | ![diphenylmethyl] | $C_{63}H_{93}NO_6(959)$; 966 (M + Li$^+$) |
| 480 | ![triphenylmethyl] | $C_{69}H_{97}NO_6(1035)$; 1042 (M + Li$^+$) |
| 481 | ![4-chlorobenzyl-ethyl] | $C_{57}H_{88}ClNO_6(917)$; 924 (M + Li$^+$) |
| 482 | ![2,6-dimethylphenyl-ethyl] | $C_{59}H_{94}NO_6(911)$; 918 (M + Li$^+$) |
| 483 | ![2,4-dichlorophenyl-ethyl] | $C_{57}H_{87}Cl_2NO_6(951)$; 958 (M + Li$^+$) |
| 484 | ![4-methoxyphenyl-ethyl] | $C_{58}H_{91}NO_7(913)$; 920 (M + Li$^+$) |
| 485 | ![pyridyl-ethyl] | $C_{56}H_{88}N_2O_6(884)$; 891 (M + Li$^+$) |

TABLE 49-continued
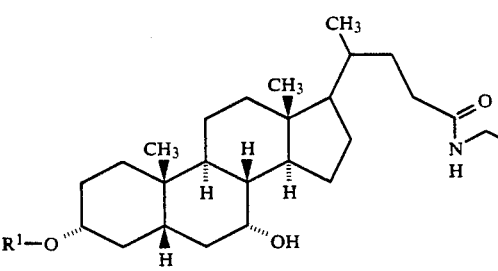
| Example | R¹ | MS (FAB,3-NBA/LiCl or LiI) |
|---|---|---|
| 486 | 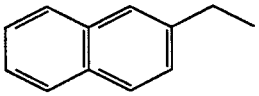 | $C_{61}H_{91}NO_6(933)$; 940 (M + Li$^+$) |
The compounds of Table 50 were obtained in analogy to Examples 366, 367 and 368.
TABLE 50
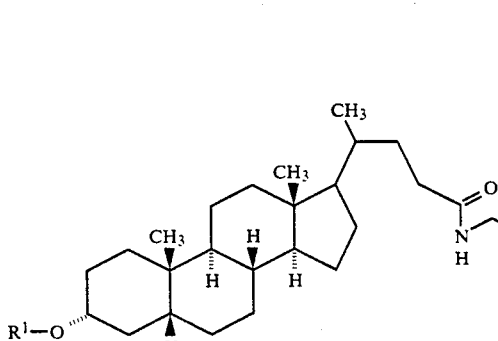
| Example | R¹ | MS (FAB,3-NBA/LiCl or LiI) |
|---|---|---|
| 487 | H | $C_{50}H_{83}NO_7(809)$; 816 (M + Li$^+$) |
| 488 | 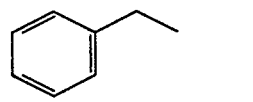 | $C_{57}H_{89}NO_7(899)$; 906 (M + Li$^+$) |
| 489 | 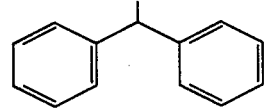 | $C_{63}H_{93}NO_7(975)$; 982 (M + Li$^+$) |
| 490 | 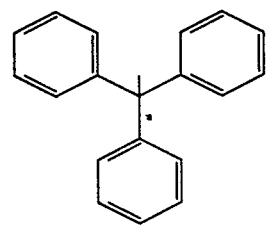 | $C_{69}H_{97}NO_7(1051)$; 1058 (M + Li$^+$) |

TABLE 50-continued
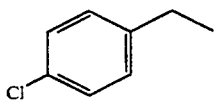
| Example | R[I] | MS (FAB,3-NBA/LiCl or LiI) |
|---|---|---|
| 491 | 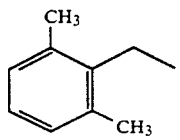 | $C_{57}H_{88}ClNO_7(933)$; 940 (M + Li$^+$) |
| 492 | 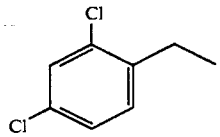 | $C_{59}H_{94}NO_7(927)$; 934 (M + Li$^+$) |
| 493 | 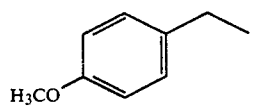 | $C_{57}H_{87}Cl_2NO_7(967)$; 974 (M + Li$^+$) |
| 494 | 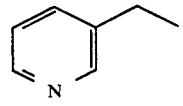 | $C_{58}H_{91}NO_8(929)$; 936 (M + Li$^+$) |
| 495 | 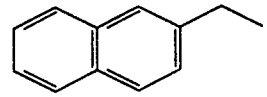 | $C_{56}H_{88}N_2O_7(900)$; 907 (M + Li$^+$) |
| 496 |  | $C_{61}H_{91}NO_7(949)$; 956 (M + Li$^+$) |
The compounds of Table 51 were obtained in analogy to Examples 366, 367 and 368.

TABLE 51

[Structure: bis-steroid compound with R¹—O— substituent, linked via amide-ethylene-ether to a second steroid bearing HO and COOH groups]

| Example | R¹ | MS (FAB,3-NBA/LiCl or LiI) |
|---|---|---|
| 497 | H | $C_{50}H_{83}NO_6(793)$; 800 (M + Li$^+$) |
| 498 | benzyl (–CH₂–C₆H₅) | $C_{57}H_{89}NO_6(883)$; 890 (M + Li$^+$) |
| 499 | diphenylmethyl (–CH(C₆H₅)₂) | $C_{63}H_{93}NO_6(959)$; 966 (M + Li$^+$) |
| 500 | triphenylmethyl (–C(C₆H₅)₃) | $C_{69}H_{97}NO_6(1035)$; 1042 (M + Li$^+$) |
| 501 | 4-chlorobenzyl | $C_{57}H_{88}ClNO_6(917)$; 924 (M + Li$^+$) |
| 502 | 2,6-dimethylbenzyl | $C_{59}H_{94}NO_6(911)$; 918 (M + Li$^+$) |
| 503 | 2,4-dichlorobenzyl | $C_{57}H_{87}Cl_2NO_6(951)$; 958 (M + Li$^+$) |
| 504 | 4-methoxybenzyl | $C_{58}H_{91}NO_7(913)$; 920 (M + Li$^+$) |
| 505 | (pyridin-3-yl)methyl | $C_{56}H_{88}N_2O_6(884)$; 891 (M + Li$^+$) |

TABLE 51-continued
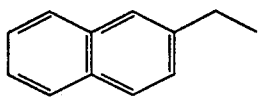
| Example | R[1] | MS (FAB,3-NBA/LiCl or LiI) |
|---|---|---|
| 506 | ![naphthylethyl] | $C_{61}H_{91}NO_6(933)$; 940 (M + Li$^+$) |
The compounds of Table 52 were obtained in analogy to Examples 366, 367 and 368.
TABLE 52
| Example | R[1] | MS (FAB, 3-NBA/LiCl or LiI) |
|---|---|---|
| 507 | H | $C_{50}H_{83}NO_6(793)$; 800(M + Li$^+$) |
| 508 | ![phenethyl] | $C_{57}H_{89}NO_6(883)$; 890(M + Li$^+$) |
| 509 | ![diphenylmethyl-CH] | $C_{63}H_{93}NO_6(959)$; 966(M + Li$^+$) |
| 510 | ![triphenylmethyl] | $C_{69}H_{97}NO_6(1035)$; 1042(M + Li$^+$) |

TABLE 52-continued
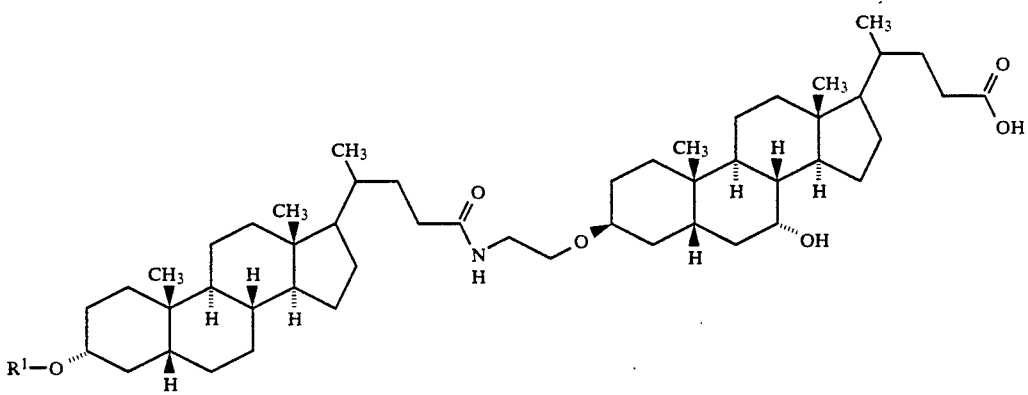
| Example | R[1] | MS (FAB, 3-NBA/LiCl or LiI) |
|---|---|---|
| 511 | 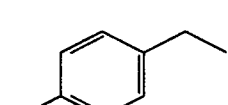 | $C_{57}H_{88}ClNO_6(917)$; 924(M + Li$^+$) |
| 512 | 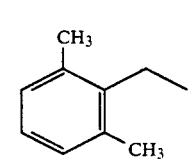 | $C_{59}H_{94}NO_6(911)$; 918(M + Li$^+$) |
| 513 | 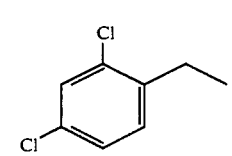 | $C_{57}H_{87}Cl_2NO_6(951)$; 958(M + Li$^+$) |
| 514 | 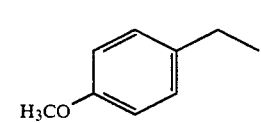 | $C_{58}H_{91}NO_7(913)$; 920(M + Li$^+$) |
| 515 | 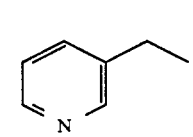 | $C_{56}H_{88}N_2O_6(884)$; 891(M + Li$^+$) |
| 516 | 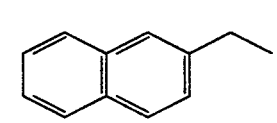 | $C_{61}H_{91}NO_6(933)$; 940(M + Li$^+$) |
The compounds of Table 53 were obtained in analogy to Examples 366, 367 and 368.

TABLE 53
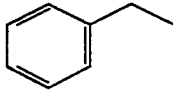
| Example | R[1] | MS (FAB, 3-NBA/LiCl or LiI) |
|---|---|---|
| 517 | H | $C_{50}H_{83}NO_5(777)$; 784(M + Li$^+$) |
| 518 | 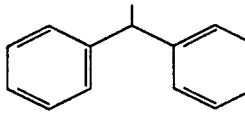 | $C_{57}H_{89}NO_5(867)$; 874(M + Li$^+$) |
| 519 | 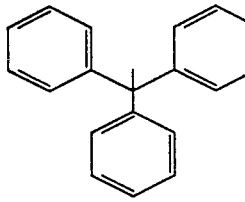 | $C_{63}H_{93}NO_5(943)$; 950(M + Li$^+$) |
| 520 | 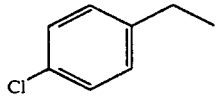 | $C_{69}H_{97}NO_5(1019)$; 1026(M + Li$^+$) |
| 521 | 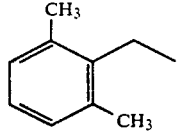 | $C_{57}H_{88}ClNO_5(901)$; 908(M + Li$^+$) |
| 522 | 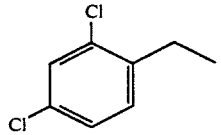 | $C_{59}H_{94}NO_5(895)$; 902(M + Li$^+$) |
| 523 | 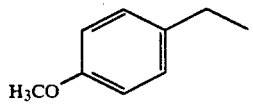 | $C_{57}H_{87}Cl_2NO_5(935)$; 942(M + Li$^+$) |
| 524 | 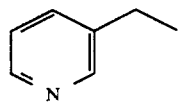 | $C_{58}H_{91}NO_6(897)$; 904(M + Li$^+$) |
| 525 |  | $C_{56}H_{88}N_2O_5(868)$; 875(M + Li$^+$) |

TABLE 53-continued

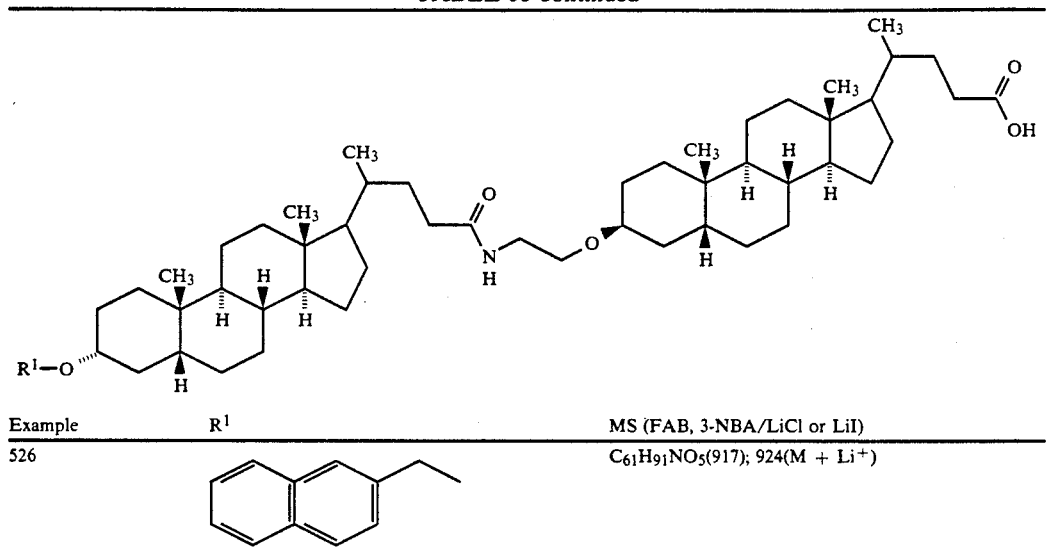

| Example | R[1] | MS (FAB, 3-NBA/LiCl or LiI) |
|---|---|---|
| 526 | (2-ethylnaphthalene) | $C_{61}H_{91}NO_5(917)$; 924(M + Li$^+$) |

EXAMPLE 527

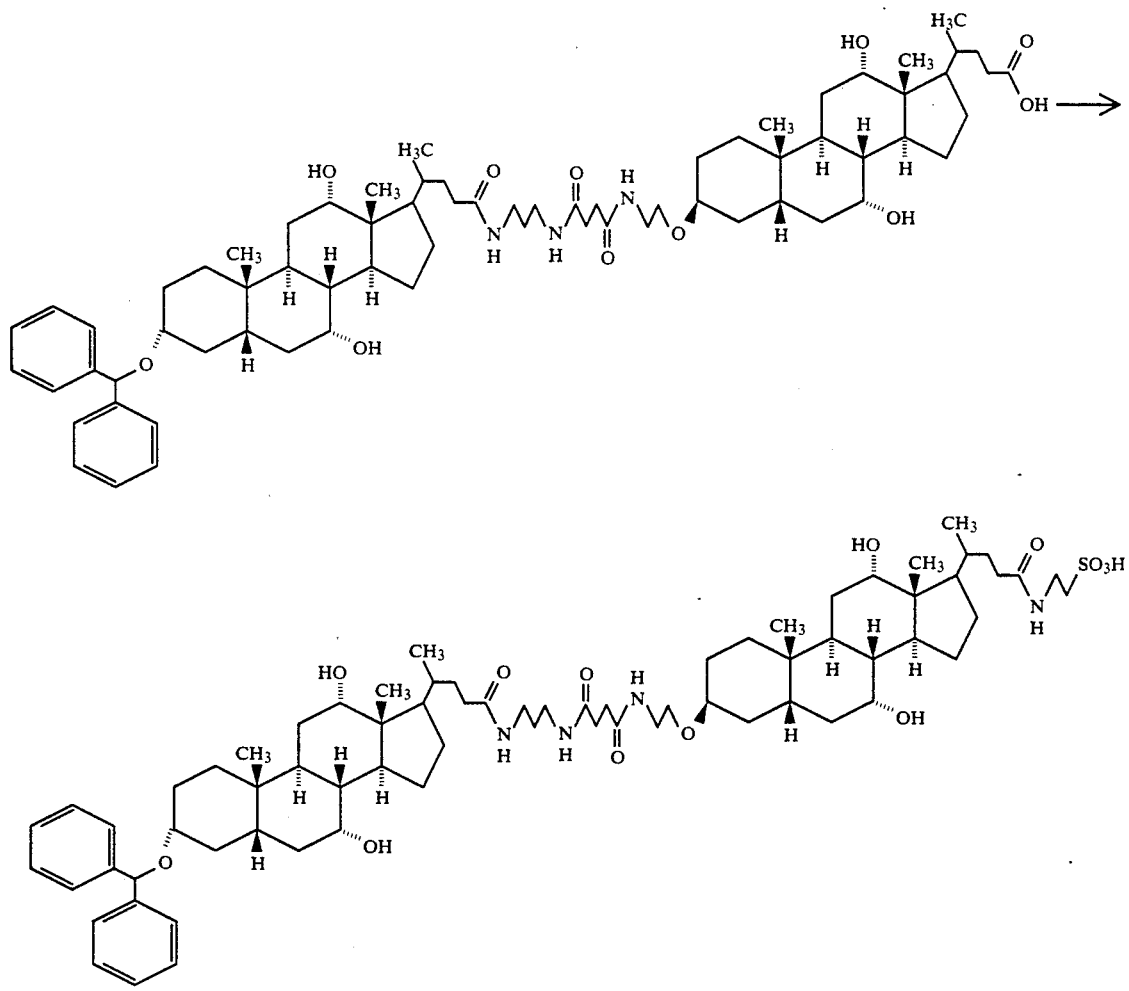

116 mg (0.1 mmol) of "Example 170" were initially introduced in 5 ml of tetrahydrofuran, 28.2 μl (0.2 mmol) of triethylamine were injected, the mixture was cooled to 0° C., 14.5 μl (0.15 mmol) of ethyl chloroformate were injected, the mixture was stirred at room temperature for 15 minutes, then 44 mg (0.35 mmol) of taurine, dissolved in 3 ml of 0.1 molar sodium hydroxide solution, were added dropwise, and the mixture was stirred at room temperature for 1 h, swirled for 10 minutes with 10 g of sodium dihydrogen phosphate and extracted with ethyl acetate/ethanol 4:1 (3 ×). The combined organic phases were dried (MgSO$_4$) and evaporated. Chromatography on silica gel (ethyl acetate/ethanol=3:2) gave 76 mg (0.06 mmol, 60%) of "Example 527"

C$_{72}$H$_{110}$N$_4$SO$_{13}$ (1270), MS (FAB, 3-NBA/LiCl); 1277 (M+Li$^+$)

The examples of Tables 18-33 were converted into taurine conjugates in analogy to Example 527.

EXAMPLE 528

116 mg (0.1 mmol) of "Example 170" were initially introduced in 5 ml of tetrahydrofuran, 28.2 µl (0.2 mmol) of triethylamine were injected, the mixture was cooled to 0° C., 14.5 µl (0.15 mmol) of ethyl chlorofor-
mate were injected, the mixture was stirred at room temperature for 15 minutes and then 26.5 mg (0.35 mmol) of glycine, dissolved in 3 ml of 0.1 molar sodium hydroxide solution, were added dropwise. The mixture was then stirred at room temperature for 1 h, swirled for 10 minutes with 10 g of sodium dihydrogen phosphate and extracted (3 ×) with ethyl acetate/ethanol 4:1. The combined organic phases were dried (MgSO$_4$) and evaporated. Chromatography on silica. gel (ethyl acetate/ethanol=3:2) gave 74 mg (0.0606 mmol, 60.6%) of "Example 528" C$_{72}$H$_{108}$N$_4$O$_{12}$ (1220), MS (FAB, 3-NBA/LiCl); 1227 (M+Li$^+$)

The examples of Tables 18-33 were converted into glycine conjugates in analogy to Example 528.

EXAMPLE 529

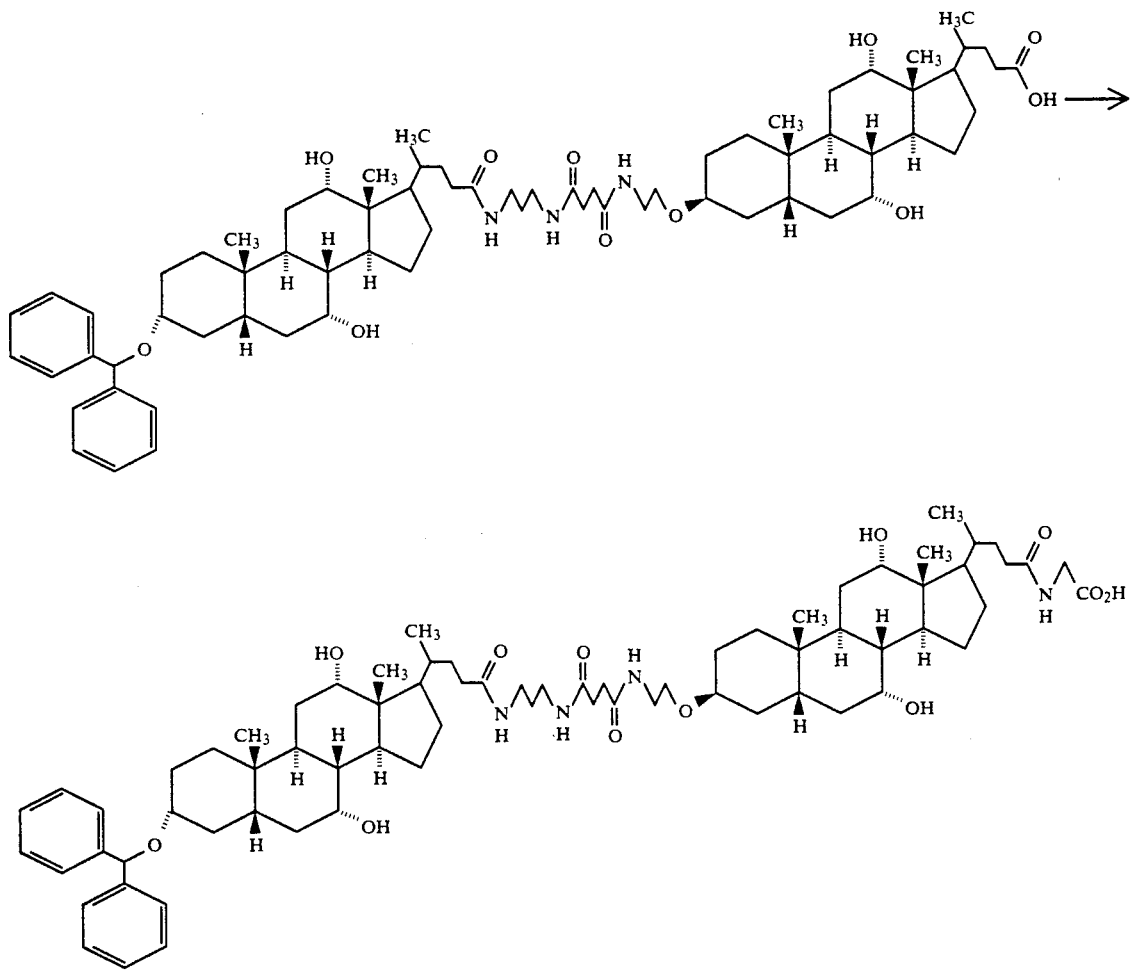

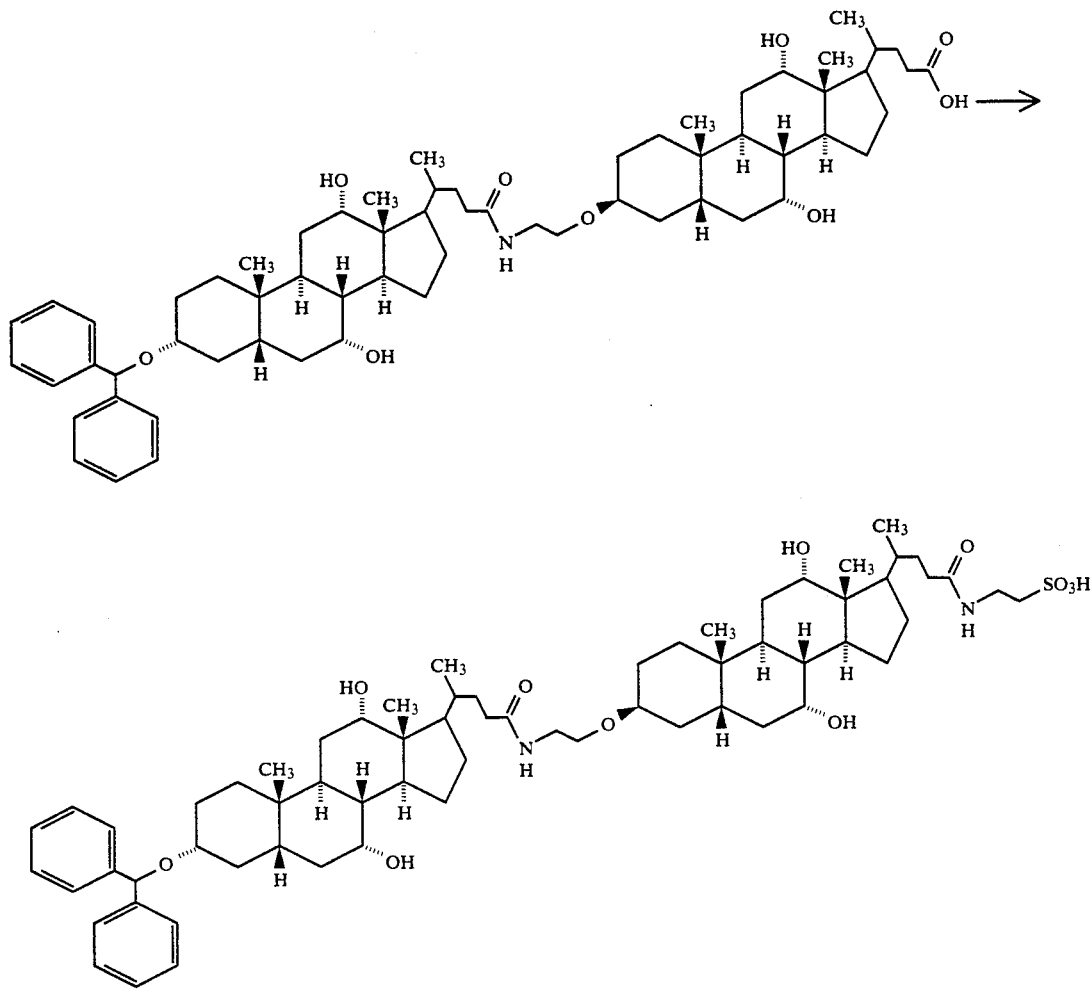

202 mg (0.2 mmol) of "Example 367" were initially introduced in 10 ml of tetrahydrofuran, 56.5 µl (0.4 mmol) of triethylamine were injected, the mixture was cooled to 0° C., 29 µl (0.3 mmol) of ethyl chlorofomate were injected, the mixture was stirred at room temperature for 15 minutes and then 88 mg (0.7 mmol) of taurine, dissolved in 6 ml of 0.1 molar sodium hydroxide solution, were added dropwise. The mixture was stirred at room temperature for 1 h, swirled for 10 minutes with 20 g of sodium dihydrogen phosphate and extracted (3 ×) with ethyl acetate/ethanol 4:1. The combined organic phases were dried ($MgSO_4$) and evaporated. Chromatography on silica gel (ethyl acetate/ethanol=3:2) gave 194 mg (0.17 mmol, 87%) of "Example 529,"

$C_{85}H_{98}N_2O_{11}S$ (1114), MS (FAB, 3-NBA/LiCl); 1121 ($M+Li^+$)

The examples of Tables 38-53 were converted into taurine conjugates in analogy to Example 529.

EXAMPLE 530

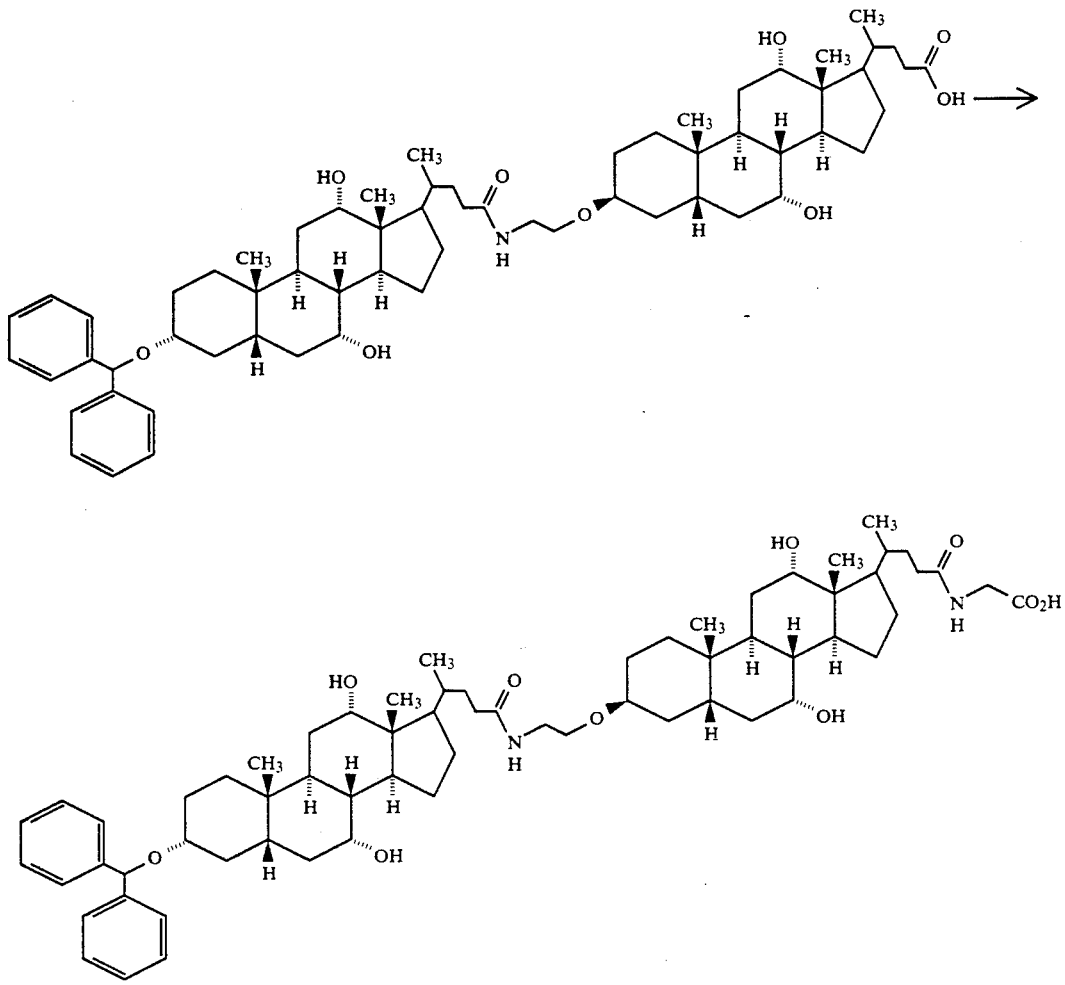

202 mg (0.2 mmol) of "Example 367" were initially introduced in 10 ml of tetrahydrofuran, 56.5 μl (0.4 mmol) of triethylamine were injected, the mixture was cooled to 0° C., 29 μl (0.3 mmol) of ethyl chloroformate were injected, the mixture was stirred at room temperature for 15 minutes and then 53 mg (0.7 mmol) of glycine, dissolved in 6 ml of 0.1 molar sodium hydroxide solution, were added dropwise. The mixture was stirred at room temperature for 1 h, swirled for 10 minutes with 20 g of sodium dihydrogen phosphate and extracted (3 ×) with ethyl acetate/ethanol 4:1. The combined organic phases were dried ($MgSO_4$) and evaporated. Chromatography on silica gel (ethyl acetate/ethanol = 3:2) gave 181 mg (0.17 mmol, 85%) of "Example 530"

$C_{65}H_{95}N_2O_{10}$ (1064), MS (FAB, 3-NBA/LiCl); 1071 ($M+Li^+$)

The examples of Tables 38–53 were converted into glycine conjugates in analogy to Example 530.

EXAMPLE 531

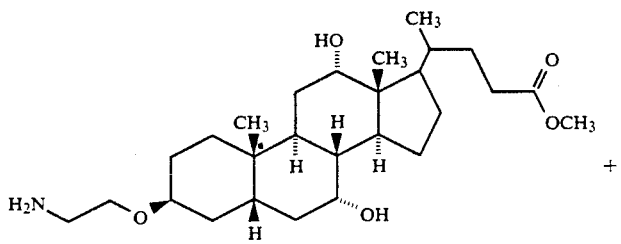

+

-continued

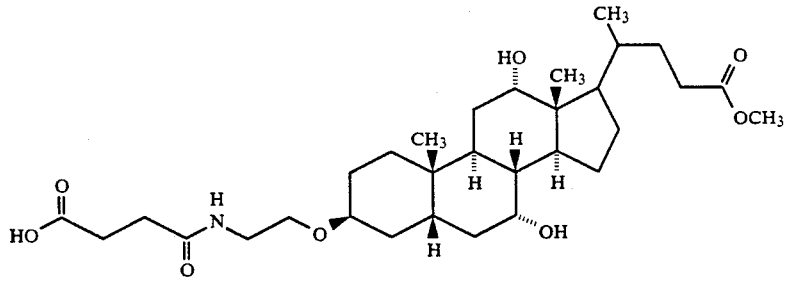

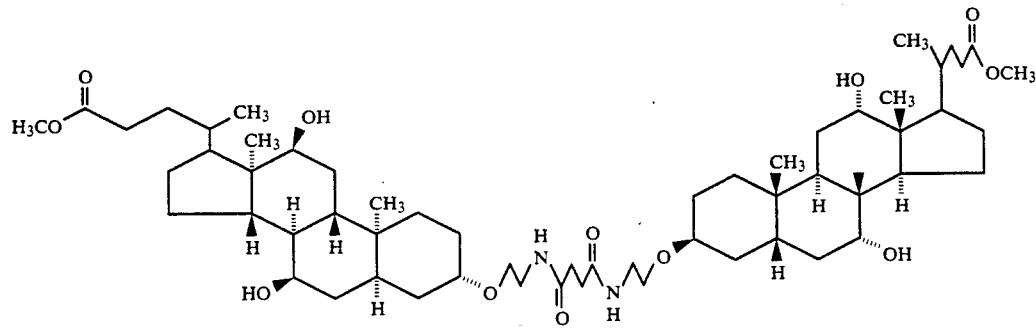

565 mg (1 mmol) of "Example 165", dissolved in 20 ml of tetrahydrofuran and 5 ml of triethylamine, were initially introduced and 96 μl (1 mmol) of ethyl chloroformate were injected at 0° C. The mixture was stirred at 0° C. for 15 minutes. 465 mg (1 mmol) of "Example 139" dissolved in 10 ml of tetrahydrofuran were then added dropwise. The mixture was stirred at room temperature for 1.5 h. The reaction solution was poured into 1 molar hydrochloric acid, then extracted (3 ×) with ethyl acetate. The combined organic phases were washed with saturated NaHCO$_3$ solution and dried (MgSO$_4$).

Evaporation of the solvent and flash chromatography on silica gel (ethyl acetate/methanol=5:1) gave 608 mg (0.601 mmol, 60.1%) of "Example 531"

$C_{58}H_{96}N_2O_{12}$ (1012), MS (FAB, 3-NBA/LiCl): 1019 (M+Li$^+$)

EXAMPLE 532

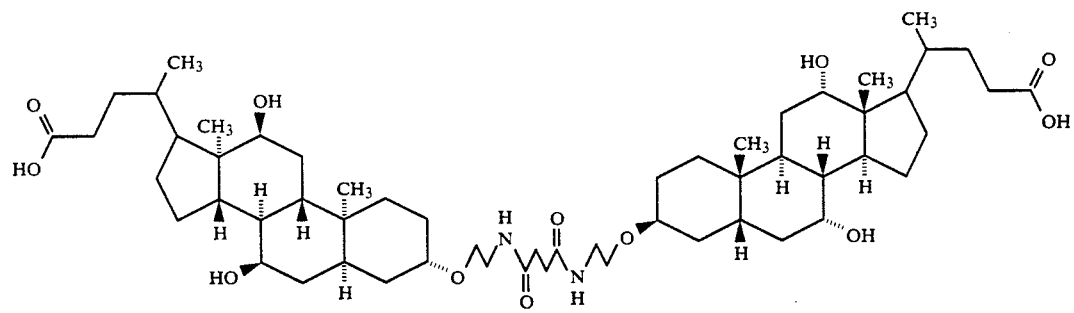

300 mg (0.296 mmol) of "Example 531" were dissolved in 10 ml of ethanol and 3 ml of 1 molar sodium hydroxide solution were added, and the mixture was stirred at room temperature for 24 h, then intensively swirled for 15 minutes with 6 g of sodium dihydrogen phosphate and extracted (3 ×) with ethyl acetate/ethanol×4:1. The combined organic phases were dried (MgSO$_4$).

Evaporation of the solvent trituration with diisopropyl ether and filtration with suction gave 268 mg (0.272 mmol, 92%) of "Example 532" $C_{56}H_{92}N_2O_{12}$ (984), MS (FAB, 3-NBA/LiCl); 991 (M+Li$^+$)

The examples of Table 54 were obtained in analogy to Examples 531 and 532.

TABLE 54
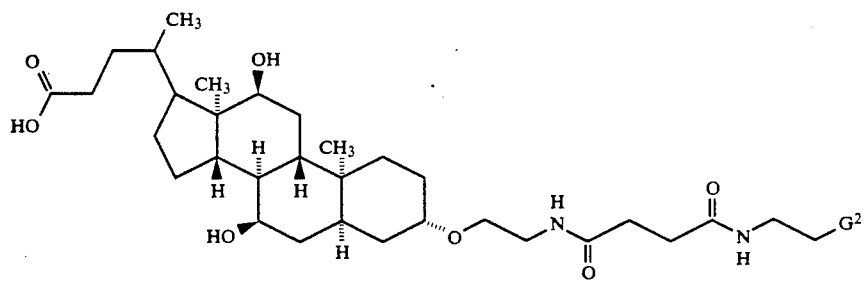
| Ex. | R¹ | MS (FAB, 3-NBA/LiCl or LiI) |
|---|---|---|
| 533 | 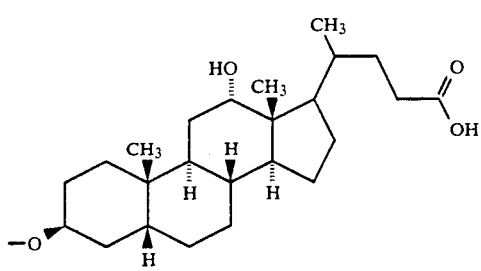 | $C_{56}H_{92}N_2O_{11}$(968); 975(M + Li$^+$) |
| 534 | 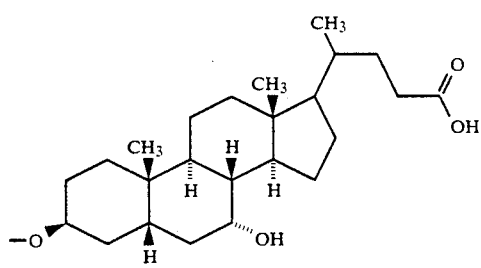 | $C_{56}H_{92}N_2O_{11}$(968); 975(M + Li$^+$) |
| 535 | 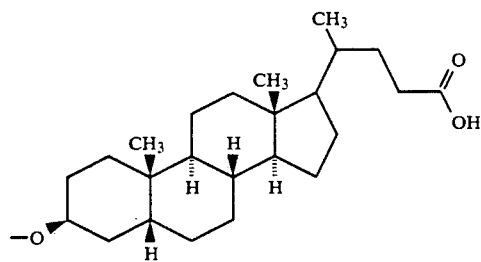 | $C_{56}H_{92}N_2O_{10}$(952); 959(M + Li$^+$) |
The examples of Table 55 were obtained in analogy to Examples 531 and 532.

TABLE 55
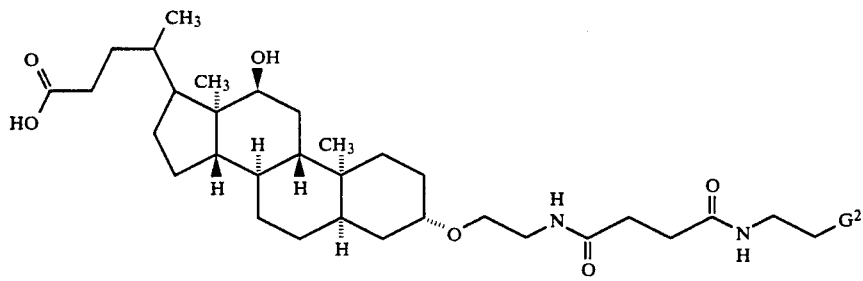
| Ex. | G² | MS (FAB, 3-NBA/LiCl or LiI) |
|---|---|---|
| 536 | 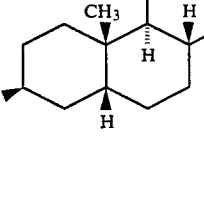 | C₅₆H₉₂N₂O₁₀(952); 959(M + Li⁺) |
| 537 | 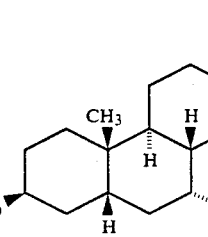 | C₅₆H₉₂N₂O₁₀(952); 959(M + Li⁺) |
| 538 | 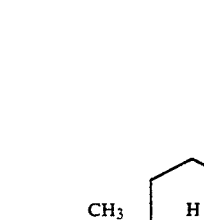 | C₅₆H₉₂N₂O₉(936); 943(M + Li⁺) |
The examples of Table 56 were obtained in analogy to Examples 531 and 532.

TABLE 56
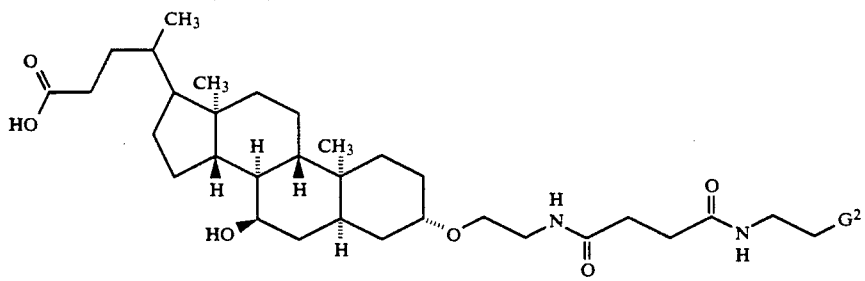
| Ex. | G² | MS (FAB, 3-NBA/LiCl or LiI) |
|---|---|---|
| 539 | ![structure] | C₅₆H₉₂N₂O₁₀(952); 959(M + Li⁺) |
| 540 | ![structure] | C₅₆H₉₂N₂O₉(936); 943(M + Li⁺) |
The examples of Table 57 were obtained in analogy to Examples 531 and 532.
TABLE 57
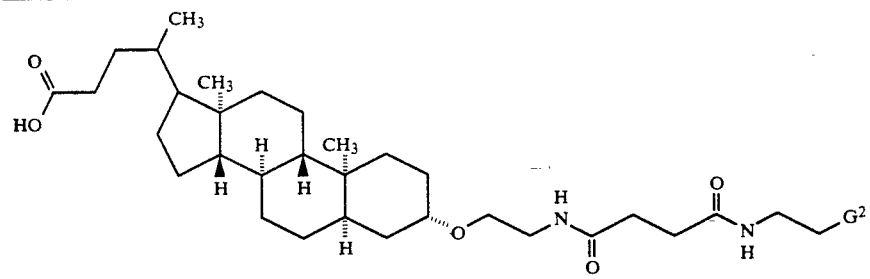
| Ex. | G² | MS (FAB, 3-NBA/LiCl or LiL) |
|---|---|---|
| 541 | ![structure] | C₅₆H₉₂N₂O₈(920); 927(M + Li⁺) |
For futher variation of the group X, the following compounds were prepared (L=H)

TABLE 58
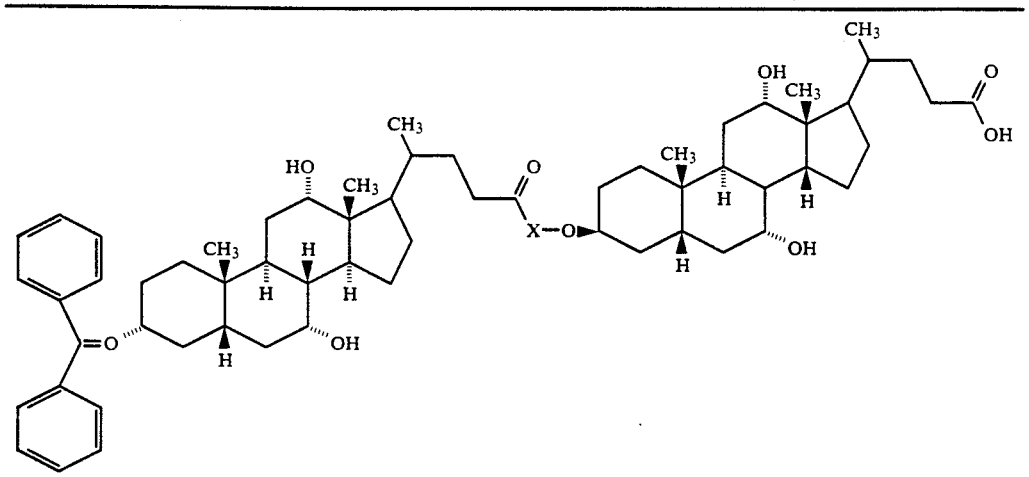
| Example | X |
|---|---|
| 542 | —NH—(CH₂)₃—NH—C(O)—CH₂CH₂—C(O)—NH—(CH₂)₄— |
| 543 | —NH—(CH₂)₅—NH—C(O)—CH₂CH₂—C(O)—NH—(CH₂)₆— |
| 544 | —NH—(CH₂)₆—NH—C(O)—CH₂CH₂—C(O)—NH—(CH₂)₅— |
| 545 | —NH—(CH₂)₈—NH—C(O)—CH₂CH₂—C(O)—NH—(CH₂)₃— |
| 546 | —NH—(CH₂)₁₀—NH—C(O)—CH₂CH₂—C(O)—NH—(CH₂)₄— |
| 547 | —NH—(CH₂)₁₂—NH—C(O)—CH₂CH₂—C(O)—NH—(CH₂)₇— |
| 548 | —NH—(CH₂)₁₀—NH—C(O)—CH₂CH₂—C(O)—NH—(CH₂)₁₀— |
| 549 | —NH—CH₂CH₂—O—CH₂CH₂—O—CH₂—NH—C(O)—CH₂CH₂—C(O)—NH—(CH₂)₅— |
| 550 | —NH—C₆H₄—CH₂—C₆H₄—NH—C(O)—CH₂CH₂—C(O)—NH—(CH₂)₃— |

TABLE 58-continued
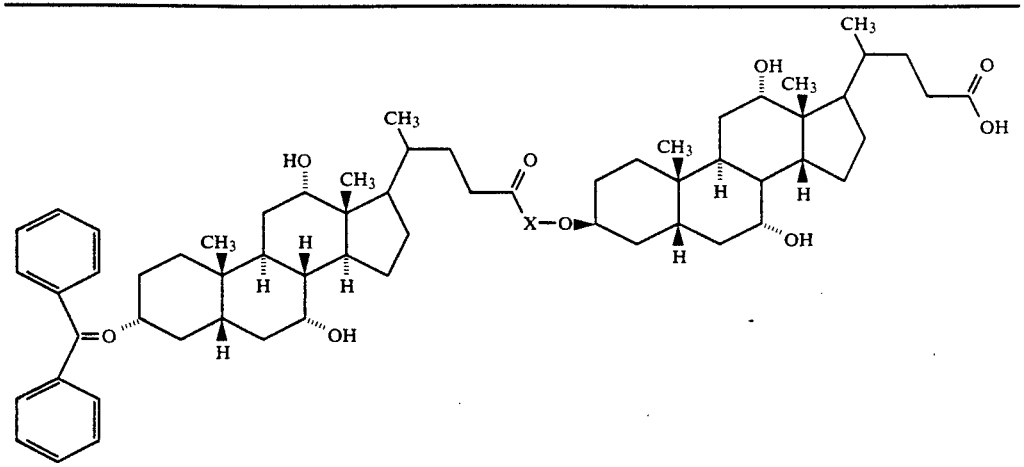
| Example | X |
|---------|---|
| 551 | 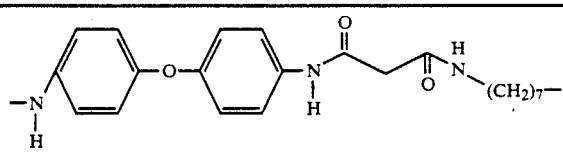 |
| 552 | 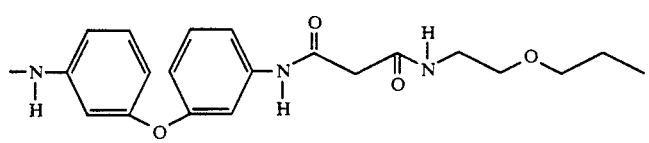 |
| 553 | 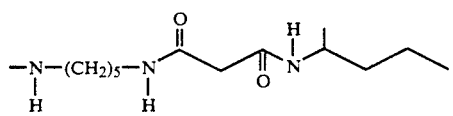 |
| 554 | direct bond |
| 555 | 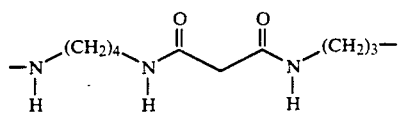 |
| 556 | 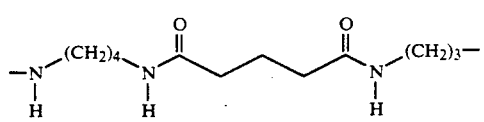 |
| 557 | 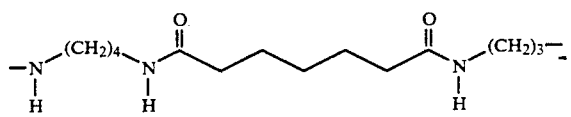 |
Table 59 shows compounds of Table 58 in which $L_1$, $L_2$ and $L_3$ have additionally been varied
| Ex. | X | $L_1$ | $L_2$ | $L_3$ |
|-----|---|-------|-------|-------|
| 558 | ![structure] | H— | $CH_3$— | $CH_3$— |
| 559 | " | $CH_3$— | H— | $C_3H_7$— |
| 560 | " | H— | H— | $C_5H_{11}$— |

-continued

| Ex. | X | L₁ | L₂ | L₃ |
|-----|---|-----|-----|-----|
| 561 | " | $C_3H_7-$ | H— | 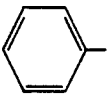 |
| 562 | " | H— | 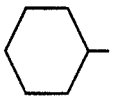 | 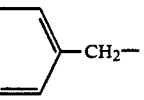 |
| 563 | " | $CH_3-$ | $C_2H_5-$ | $C_2H_5-$ |
| 564 | " | $C_2H_5-$ | 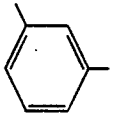 | $CH_3-$ |

Table 60 shows $IC_{50}$ and $IC_{50}$ Na values of some dimeric bile acids:

TABLE 60

| Compounds from example | $IC_{50}$ | $IC_{50}$ Na |
|---|---|---|
| 527 | 20 | 10 |
| 191 (taurine conj.) | 18 | 14 |
| 170 | 25 | 14 |
| 528 | 26 | 16 |
| 191 (glycine conj.) | 27 | 18 |
| 172 (taurine conj.) | 32 | 20 |
| 368 (glycine conj.) | 48 | 16 |
| 368 | 45 | 18 |
| 369 (taurine conj.) | 50 | 18 |
| 369 | 55 | 20 |
| 191 | 58 | 29 |
| 531 | >50 | 18 |
| 532 | 30 | 10 |

EXAMPLE 565

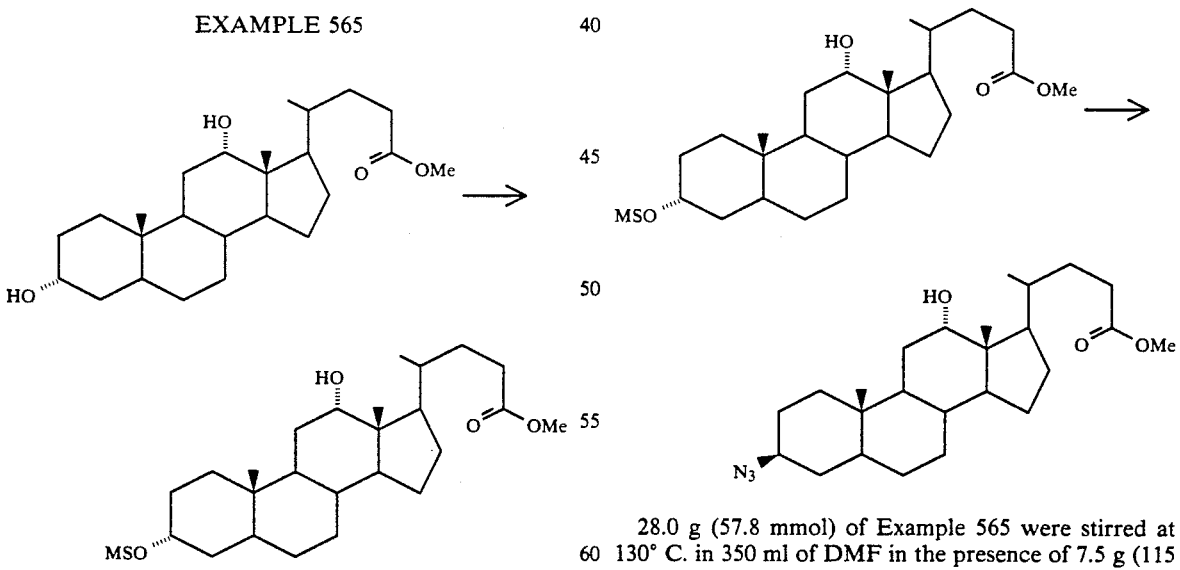

50 g (123 mmol) of methyl deoxycholate were dissolved in 300 ml of pyridine and cooled to 5° C. 15 ml (193 mmol) of methanesulfonyl chloride were added dropwise with stirring and the mixture was then stirred at room temperature for 12 h. It was poured into water and extracted with ethyl acetate. After drying and concentration of the organic phase, the residue was chromatographed on silica gel (ethyl acetate). Yield 29.5 g (49%) of "Example 565"

$C_{26}H_{44}O_6S$ (484), MS (FAB, 3-NBA/LiCl): 491 $(M+Li^+)$.

EXAMPLE 566

28.0 g (57.8 mmol) of Example 565 were stirred at 130° C. in 350 ml of DMF in the presence of 7.5 g (115 mmol) of sodium azide for 1.5 h. The mixture was poured into water and extracted with ethyl acetate. After drying and concentration of the organic phase,, the residue was filtered through silica gel (cyclohexane/ethyl acetate 1:1). Yield 18.5 g (74%) of "Example 566".

$C_{25}H_{41}N_3O_3$ (431), MS (FAB, 3-NBA/LiCl) : 438 $(M+Li^+)$.

EXAMPLE 567

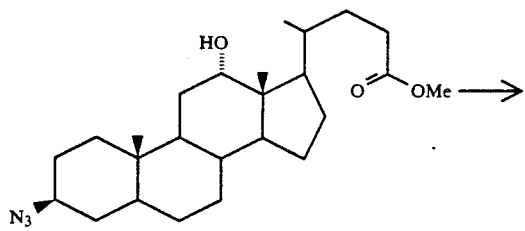

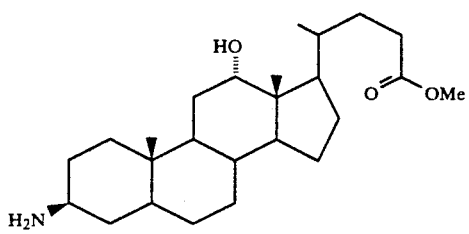

5.0 g (11.6 mmol) of Example 566 were hydrogenated at room temperature and normal pressure in 150 ml of ethyl acetate in the presence of 0.5 g of Pd/C (10%). The catalyst was filtered off and the filtrate was concentrated. Chromatography on silica gel (reethanol, then methanol/triethylamine 98:2) gave 3.1 g (66%) of "Example 567".

$C_{25}H_{43}NO_3$ (405),, MS (FAB, 3-NBA/LiCl): 412(M+Li+).

Examples 568 and 569 were prepared analogously to Examples 565–567.

EXAMPLE 570

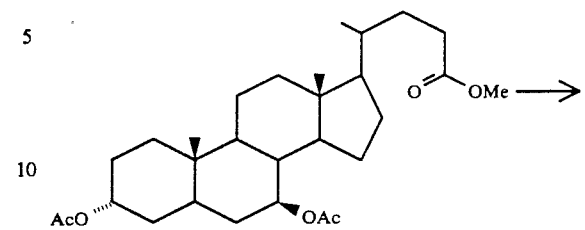

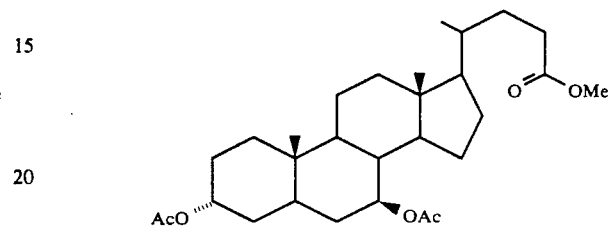

14.4 g (28.4 umol) of methyl 3α, 7β-diacetoxycholate in 100 ml of methanol were added to a solution prepared from 5.75 g (0.25 mol) of sodium and 400 ml of methanol and the mixture was stirred at room temperature. After 15 min, saturated sodium dihydrogenphosphate solution was added and the mixture was extracted several times with ethyl acetate. Drying and concentration of the organic phase gave 1.18 g (90%) of "Example 570" which was further reacted without further purification. $C_{27}H_{44}NO_5$, MS (FABR 3-NBA/LiCl): 455 (M+Li+).

| Ex. | | MS (FAB, 3-NBA/LiCl or LiI |
|---|---|---|
| 568 | 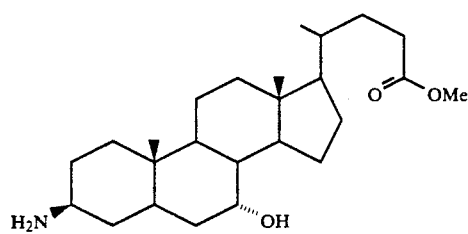 | $C_{25}H_{43}NO_3$; 412 (M + Li+) 405 |
| 569 | 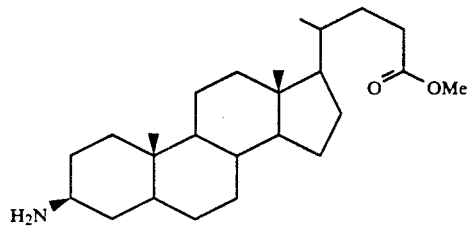 | $C_{25}H_{43}NO_2$; 396 (M + Li+) 389 |

EXAMPLE 571

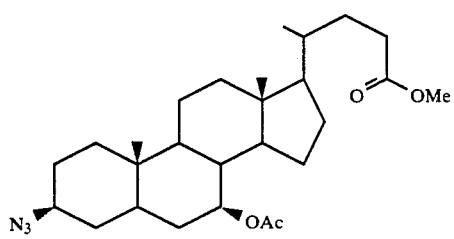

"Example 571" was obtained from Example 570 in analogy to Examples 565 and 566.

$C_{27}H_{43}N_3O_4$ (473), MS (FAB, 3-NBA/LiCl): 480 $(M+Li^+)$.

EXAMPLE 572

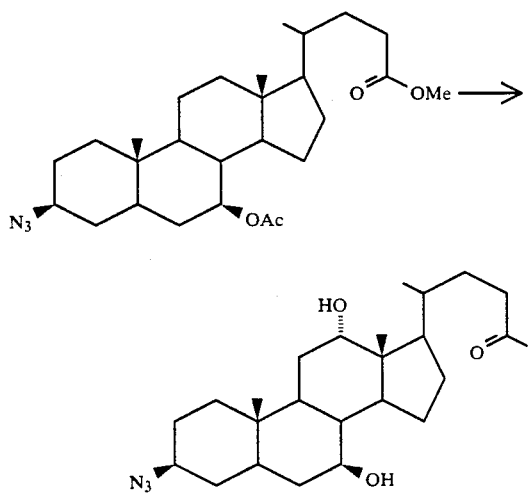

5.7 g (12.0 mmol) of Example 571 were heated under reflux for 1 h in 300 ml of 2M sodium methylate solution in methanol. Working-up was carried out by the process described for Example 570. Chromatography on silica gel (cyclohexane/ethyl acetate 1:1) gave 4.3 g (83%) of "Example 572".

$C_{25}H_{41}N_3O_3$ (431), MS (FAB, 3-NBA/LiCl) 438 $(M+Li^+)$.

EXAMPLE 573

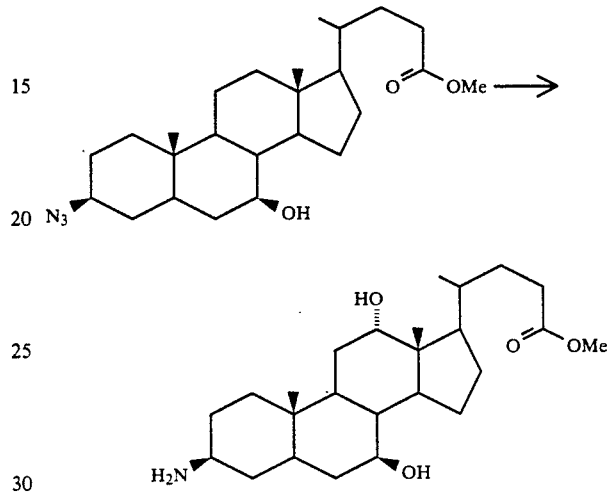

"Example 573" was prepared from Example 572 analogously to Example 567.

$C_{25}H_{43}NO_3$ (405), MS (FAB, 3-NBA/LiCl), 412 $(M+Li^+)$.

EXAMPLE 574

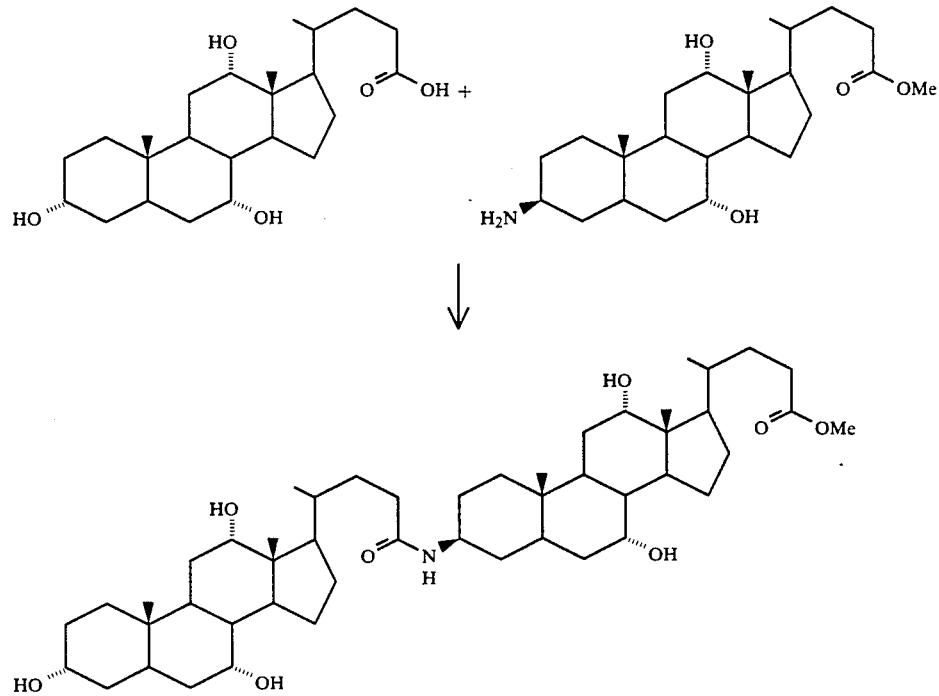

1.0 g (2.45 mmol) of cholic acid, 1.03 g (2.45 mmol) of methyl 3β-amino-7α,12α-dihydroxycholate and 550 mg (4.07 mmol) of hydroxybenzotriazole were stirred at room temperature for 20 min in 40 ml of THF. After cooling to 0° C. 610 mg (2.96 mmol) of dicyclohexylcarbodiimide in 10 ml of THF were added dropwise and the mixture was additionally stirred at room temperature for 12 h. The solid was filtered off, the solvent was concentrated and the residue was chromatographed on silica gel (CHCl$_3$/methanol 9:1). Yield 1.2 g (60%) of "Example 574⇌.

$C_{49}H_{81}NO_9$ (811), MS (FAB, 3-NBA/LiCl): 818 (M+Li$^+$).

EXAMPLE 575

530 mg (0.65 mmol) of Example 574 were stirred at room temperature for 18 h in 10 ml of ethanol and 2 ml of 1M sodium hydroxide solution. After addition of water, the alcohol was distilled off. The aqueous solution was acidified with 1.3 ml of 2M HCl. The precipitate was filtered off with suction and dried and 510 mg (98%) of "Example 575" were obtained.

$C_{48}H_{79}NO_8$ (797), MS (FAB, 3-NBA/LiCl): 804 (M+Li$^+$).

The examples of Table 61 were prepared in analogy to Examples 574 and 575.

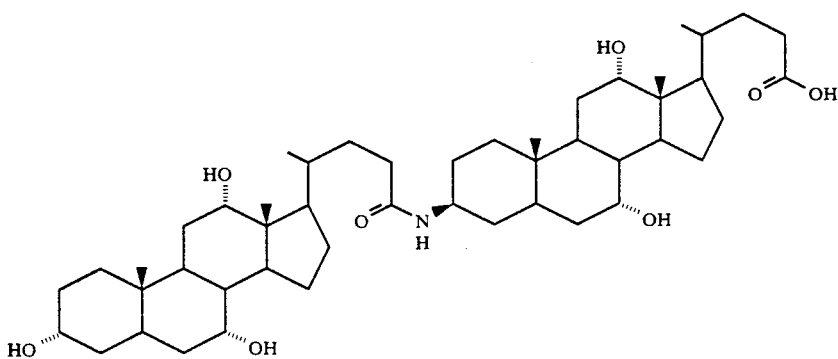

TABLE 61

| Ex. | G1 | MS (FAB, 3-NBA/LiCl or LiI |
|---|---|---|
| 576 | (structure shown) | $C_{48}H_{79}NO_7$ (781) 788 (M + Li$^+$) |
| 577 | (structure shown) | $C_{48}H_{79}NO_7$ (781) 788 (M + Li$^+$) |

TABLE 61-continued
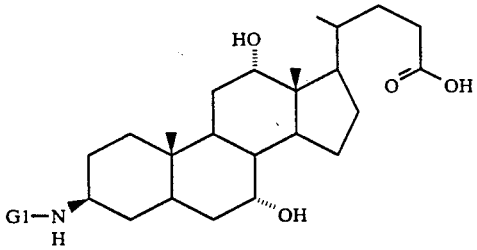
| Ex. | G1 | MS (FAB, 3-NBA/LiCl or LiI) |
|---|---|---|
| 578 | 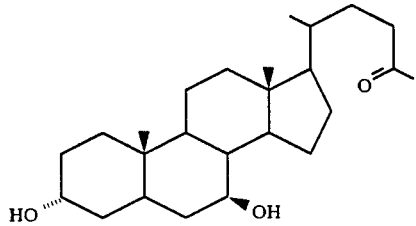 | $C_{48}H_{79}NO_7$ (781) 788 (M + Li$^+$) |
| 579 | 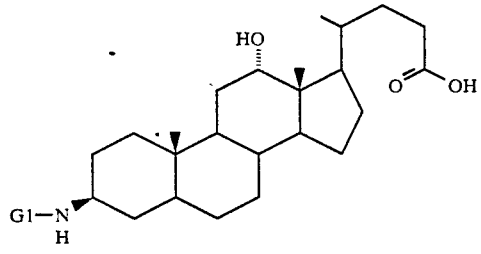 | $C_{48}H_{79}NO_6$ (765) 772 (M + Li$^+$) |
The examples of Table 62 were prepared in analogy to Examples 574 and 575.
TABLE 62
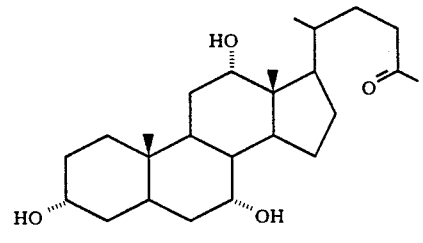
| Ex. | G1 | MS (FAB, 3-NBA/LiCl or LiI) |
|---|---|---|
| 580 | | $C_{48}H_{29}NO_7$ (781) 788 (M + Li$^+$) |
| 581 | | $C_{48}H_{29}NO_6$ (765) 772 (M + Li$^+$) |

TABLE 62-continued
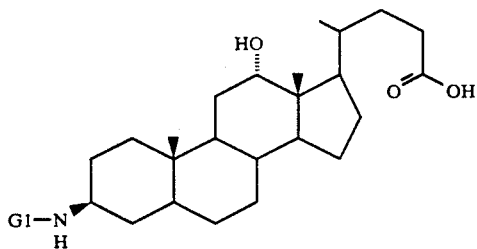
| Ex. | G1 | MS (FAB, 3-NBA/LiCl or LiI |
|---|---|---|
| 582 | 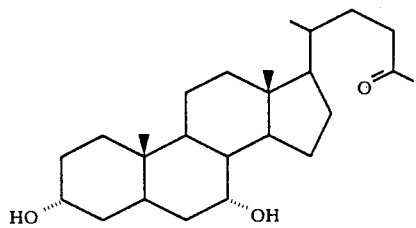 | $C_{48}H_{79}NO_6$ (765) 772 (M + Li$^+$) |
| 583 | 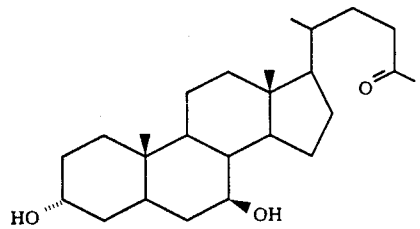 | $C_{48}H_{79}NO_6$ (765) 772 (M + Li$^+$) |
| 584 | 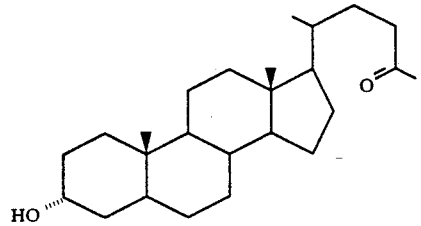 | $C_{48}H_{79}NO_5$ (749) 756 (M + Li$^+$) |
The examples of Table 63 were prepared in analogy to Examples 574 and 575.

TABLE 63
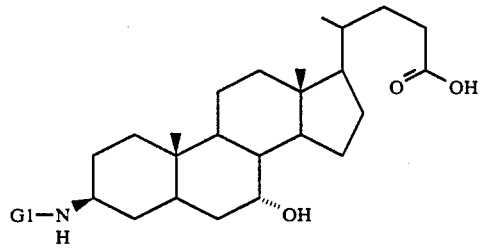
| Ex. | G1 | MS (FAB, 3-NBA/LiCl or LiI) |
|---|---|---|
| 585 | 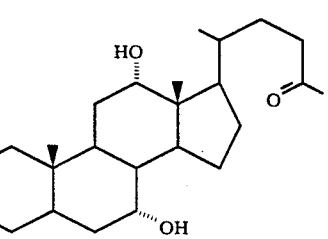 | $C_{48}H_{79}NO_7$ (781) 788 (M + Li$^+$) |
| 586 | 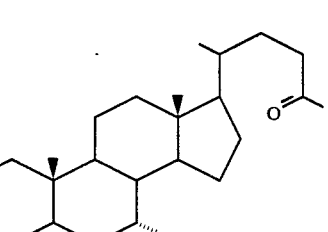 | $C_{48}H_{79}NO_6$ (765) 772 (M + Li$^+$) |
| 587 | 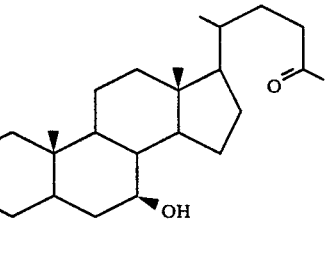 | $C_{48}H_{75}NO_6$ (765) 772 (M + Li$^+$) |
| 588 | 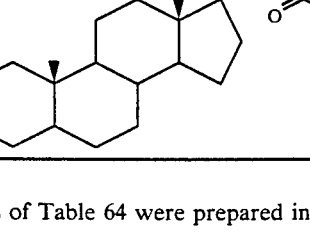 | $C_{48}H_{79}NO_6$ (765) 772 (M + Li$^+$) |
| 589 |  | $C_{48}H_{79}NO_5$ (749) 756 (M + Li$^+$) |
The examples of Table 64 were prepared in analogy to Examples 574 and 575.

TABLE 64

| Ex. | G1 | MS (FAB, 3-NBA/or LiI) |
|---|---|---|
| 590 | (structure: 3α-OH, 7α-OH, 12α-OH cholanoyl) | C₄₈H₇₉NO₇ (781) 788 (M + Li⁺) |
| 591 | (structure: 3α-OH, 12α-OH cholanoyl) | C₄₈H₇₉NO₆ (765) 772 (M + Li⁺) |
| 592 | (structure: 3α-OH, 7α-OH cholanoyl) | C₄₈H₇₉NO₆ (765) 772 (M + Li⁺) |
| 593 | (structure: 3α-OH, 7β-OH cholanoyl) | C₄₈H₇₉NO₆ (765) 772 (M + Li⁺) |
| 594 | (structure: 3α-OH cholanoyl) | C₄₈H₇₉NO₅ (749) 756 (M + Li⁺) |

The examples of Table 65 were prepared in analogy to Examples 574 and 575

TABLE 65

| Ex. | G1 | MS (FAB, 3-NBA/LiCl or LiI |
|---|---|---|
| 595 | | $C_{48}H_{79}NO_6$ (765) 772 (M + Li$^+$) |
| 596 | | $C_{48}H_{79}NO_5$ (749) 756 (M + Li$^+$) |
| 597 | | $C_{48}H_{79}NO_5$ (749) 756 (M + Li$^+$) |
| 598 | | $C_{48}H_{79}NO_5$ (749) 756 (M + Li$^+$) |
| 599 | | $C_{48}H_{79}NO_4$ (733) 740 (M + Li$^+$) |

EXAMPLE 600

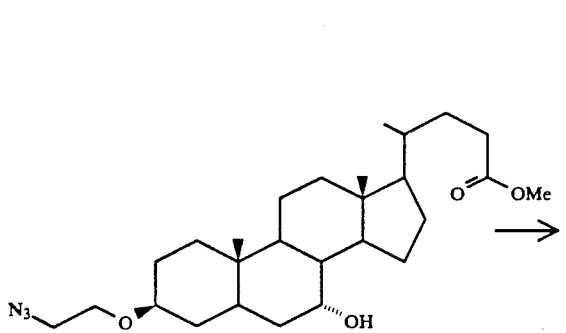

25 ml (0.32 mol) of methanesulfonyl chloride were added dropwise at 0° C. to a solution of 15.0 g (31.5 mmol) of methyl 3β-(2-azidoethoxy)-7α-hydroxycholate in 150 ml of pyridine. After 3 h at room temperature, the mixture was poured into ice-water and extracted with ethyl acetate. After drying and concentration of the organic phases, the residue was chromatographed on silica gel (cyclohexane/ethyl acetate 2:1). 13.8 g (79%) of "Example 600" obtained. $C_{28}H_{47}N_3O_6S$ (553), MS (FAB, 3-NBA/LiCl): 560 (M+Li+).

EXAMPLE 601

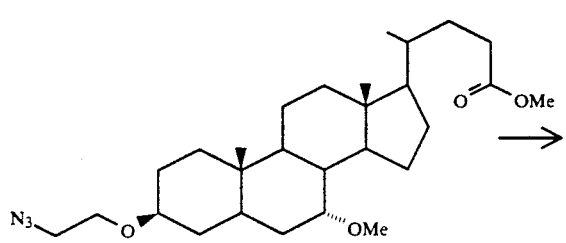

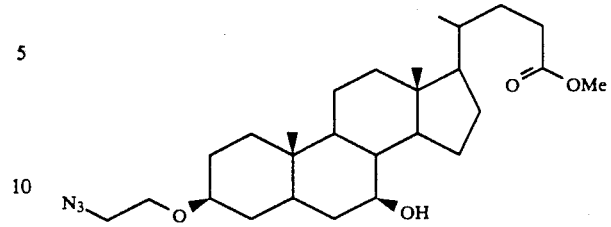

16.8 g (237 mmol) of $KO_2$ and 7.2 g (27.2 mmol) of 18-crown-6 were stirred at room temperature for 15 min in 300 ml of DMSO. 13.0 g (23.5 mmol) of Example 600 in 50 ml of DMSO were added dropwise at 20° C. After 1.5 h at room temperature, the mixture was again cooled to 0° C., saturated NaCl solution was added slowly and the mixture was acidified with 2N HCl. After extracting several times with ethyl acetate, the organic phases were dried and concentrated. The crude product was esterified in a solution prepared from 130 ml of methanol and 13 ml of acetyl chloride. After working-up, the crude product was chromatographed on silica gel (cyclohexane/ethyl acetate 6:4). Yield: 5.65 g (51%) of "Example 601".

$C_{27}H_{45}N_3O_4$ (475), MS (FAB, 3-NBA/LiCl): 482 (M+Li+)

EXAMPLE 602

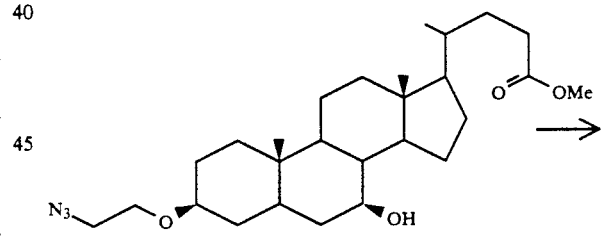

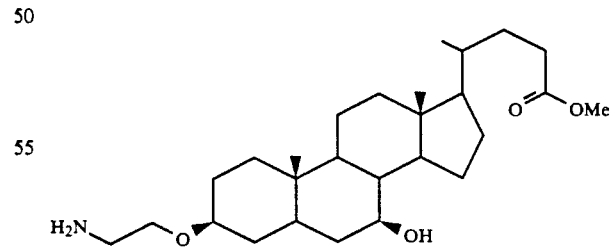

"Example 602" was prepared from Example 601 analogously to Example 567.

$C_{27}H_{47}NO_4$ (449), MS (FAB, 3-NBA/LiCl): 456 (M+Li+)

The examples of Table 66 were prepared analogously to Examples 600–602.

TABLE 66

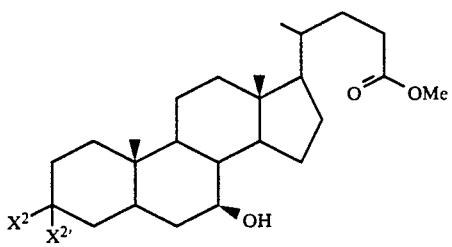

| Ex. | β-X² | α-X²' | MS (FAB, 3-NBA/LiCl or LiI) |
|---|---|---|---|
| 603 | H₂N—(CH₂)₃—O— | H | $C_{28}H_{49}NO_4$ (463), 470 (M + Li⁺) |
| 604 | H₂N—(CH₂)₄—O— | H | $C_{29}H_{51}NO_4$ (477), 484 (M + Li⁺) |
| 605 | H₂N—(CH₂)₅—O— | H | $C_{30}H_{53}NO_4$ (491), 498 (M + Li⁺) |
| 606 | H₂N—(CH₂)₆—O— | H | $C_{31}H_{55}NO_4$ (505), 512 (M + Li⁺) |
| 607 | H₂N—(CH₂)₁₀—O— | H | $C_{25}H_{63}NO_4$ (561), 568 (M + Li⁺) |
| 608 | H₂N—(CH₂)₂—O—(CH₂)₂—O— | H | $C_{29}H_{51}NO_5$ (493), 500 (M + Li⁺) |
| 609 | H₃C—CH—CH₂—O—<br>      \|<br>     NH₂ | H | $C_{28}H_{49}NO_4$ (463), 470 (M + Li⁺) |

EXAMPLE 610

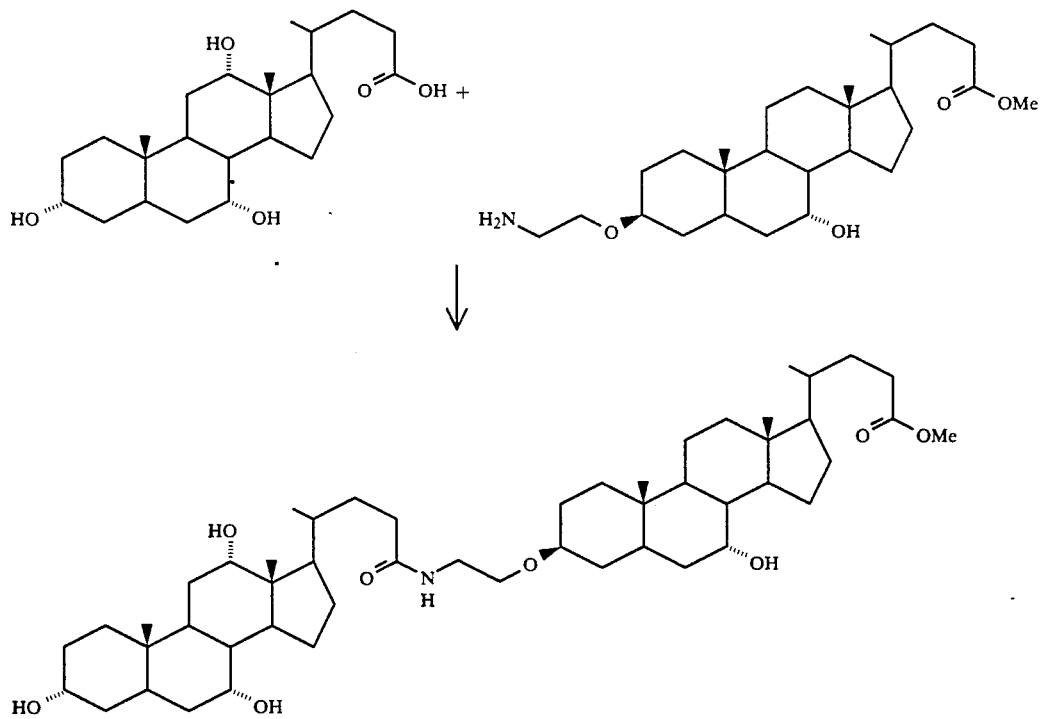

1.7 g (82%) of "Example 610" were prepared from 1.21 g (2.69 mmol) of Example 602 and 1.0 g (2.45 mmol) of cholic acid using 0.55 g (4.07 mmol) of hydroxybenzotriazole and 0.61 g (2.96 mmol) of dicyclohexylcarbodiimide according to the process described for Example 574.

$C_{51}H_{85}NO_8$ (839), MS (FAB, 3-NBA/LiCl): 836 (M+Li⁺)

EXAMPLE 611

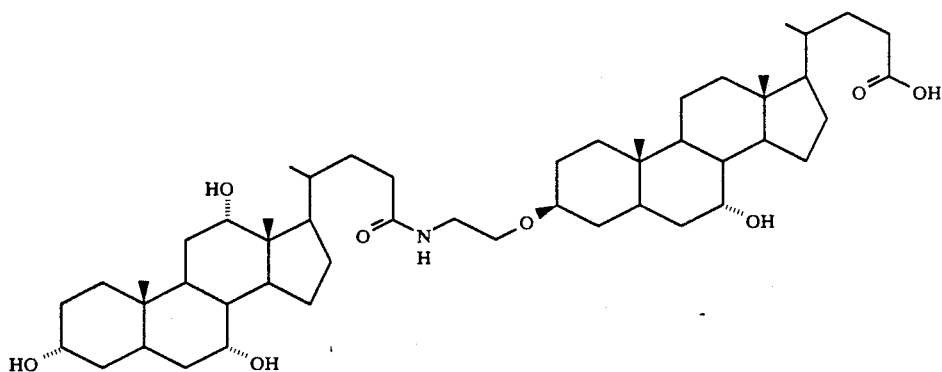

1.5 g (1.79 mmol) of Example 610 were hydrolyzed by the process described for Example 575 to give 1.14 g (77%) of "Example 611".

$C_{50}H_{93}NO_3$ (825), MS (FAB, 3-NBA/LiCl) : 832 (M+Li$^+$)

The examples of Table 67 were obtained in analogy to Examples 610 and 611.

TABLE 67

| Ex. | R$^1$ | MS (FAB, 3-NBA/or LiI |
|---|---|---|
| 612 | benzyl (PhCH$_2$CH$_2$-) | $C_{57}H_{88}NO_8$ (915), 922 (M + Li$^+$) |
| 613 | diphenylethyl (Ph$_2$CHCH$_3$-) | $C_{63}H_{93}NO_8$ (991), 998 (M + Li$^+$) |
| 614 | trityl (Ph$_3$C-) | $C_{69}H_{97}NO_8$ (1067), 1074 (M + Li$^+$) |
| 615 | 4-chlorobenzyl (4-Cl-C$_6$H$_4$-CH$_2$CH$_2$-) | $C_{57}H_{88}ClNO_8$ (949, 956 (M + Li$^+$) |

TABLE 67-continued

[Structure: steroid dimer with R¹—O— group, linked via amide-ethoxy bridge]

| Ex. | R¹ | MS (FAB, 3-NBA/LiCl or LiI) |
|---|---|---|
| 616 | 2,6-dimethyl-3-ethylphenyl (H₃C, CH₃, ethyl substituted benzene) | $C_{59}H_{94}NO_8$ (944), 951 (M + Li⁺) |
| 617 | 4-methoxyphenethyl (H₃CO-C₆H₄-ethyl) | $C_{58}H_{91}NO_8$ (925), 952 (M + Li⁺) |
| 618 | 2,4-dichlorophenethyl | $C_{57}H_{87}Cl_2NO_8$ (983), 990 (M + Li⁺) |
| 619 | 3-pyridylethyl | $C_{56}H_{88}N_2O_8$ (916), 923 (M + Li⁺) |

| Ex. | R¹ | MS (FAB, 3-NBA/LiCl or LiI) |
|---|---|---|
| 620 | 2-naphthylethyl | $C_{61}H_{91}NO_8$ (965), 972 (M + Li⁺) |

The examples of Table 68 were obtained in analogy to Examples 610 and 611.

TABLE 68

[Structure: steroid dimer with R¹—O— group, linked via amide-ethoxy bridge]

| Ex. | R¹ | MS (FAB, 3-NBA/LiCl or LiI) |
|---|---|---|
| 621 | H | $C_{50}H_{83}NO_7$ (809), 816 (M + Li⁺) |

TABLE 68-continued

| Ex. | R¹ | MS (FAB, 3-NBA/LiCl or LiI |
|---|---|---|
| 622 | benzyl (PhCH$_2$CH$_2$–) | C$_{57}$H$_{89}$NO$_7$ (899), 906 (M + Li$^+$) |
| 623 | 1,1-diphenylethyl | C$_{63}$H$_{93}$NO$_7$ (975), 982 (M + Li$^+$) |
| 624 | triphenylmethyl | C$_{59}$H$_{87}$NO$_7$ (1051), 1058 (M + Li$^+$) |
| 625 | 4-chlorophenethyl | C$_{57}$H$_{88}$ClNO$_7$ (933), 940 (M + Li$^+$) |
| 626 | 2,6-dimethylphenethyl | C$_{59}$H$_{94}$NO$_7$ (928), 935 (M + Li$^+$) |
| 627 | 4-methoxyphenethyl | C$_{58}$H$_{91}$NO$_8$ (929), 936 (M + Li$^+$) |
| 628 | 2,4-dichlorophenethyl | C$_{57}$H$_{87}$Cl$_2$NO$_7$ (967), 974 (M + Li$^+$) |
| 629 | pyridin-3-ylethyl | C$_{56}$H$_{88}$N$_2$O$_7$ (900), 907 (M + Li$^+$) |

TABLE 68-continued
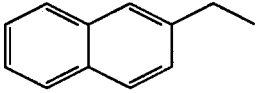
| Ex. | R$^1$ | MS (FAB, 3-NBA/LiCl or LiI |
|---|---|---|
| 630 | (2-ethylnaphthyl) | |
The examples of Table 69 were obtained in analogy to Examples 610 and 611.
TABLE 69
| Ex. | R$^1$ | MS (FAB, 3-NBA/LiCl or LiI |
|---|---|---|
| 631 | H | $C_{50}H_{83}NO_7$ (809), 816 (M + Li$^+$) |
| 632 | (phenethyl) | $C_{57}H_{89}NO_7$ (899), 906 (M + Li$^+$) |
| 633 | (1,1-diphenylethyl) | $C_{63}H_{93}NO_7$ (975), 982 (M + Li$^+$) |

TABLE 69-continued
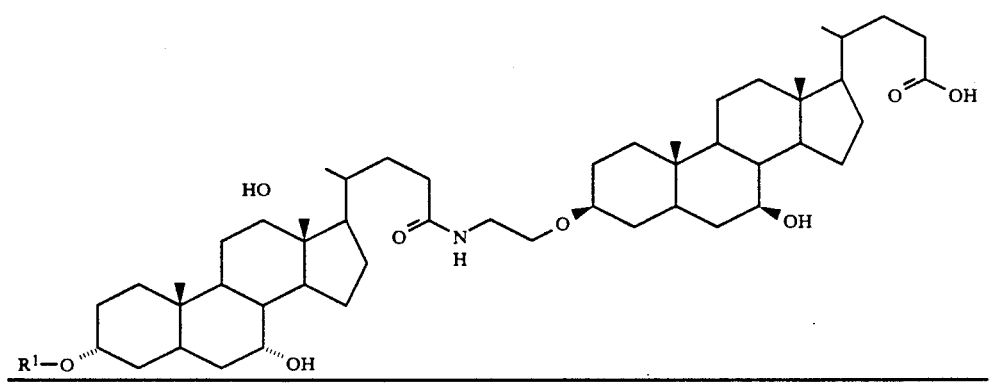
| Ex. | R¹ | MS |
|---|---|---|
| 634 | 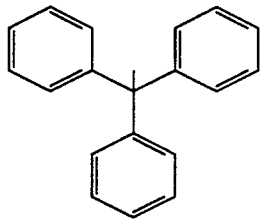 | $C_{69}H_{97}NO_7$ (1051), 1058 (M + Li⁺) |
| 635 | 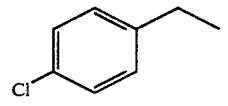 | $C_{57}H_{88}ClNO_7$ (933), 940 (M + Li⁺) |
| 636 | 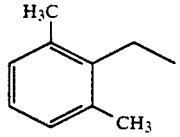 | $C_{59}H_{84}NO_7$ (928), 935 (M + Li⁺) |
| 637 | 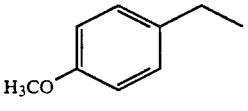 | $C_{58}H_{91}NO_8$ (929), 936 (M + Li⁺) |
| 638 | 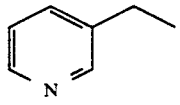 | $C_{56}H_{88}N_2O_7$ (900), 907 (M + Li⁺) |
| 639 | 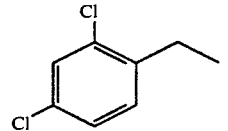 | $C_{57}H_{87}Cl_2NO_7$ (967), 974 (M + Li⁺) |
| Ex. | R¹ | MS (FAB, 3-NBA/LiI or LiI |
|---|---|---|
| 640 | 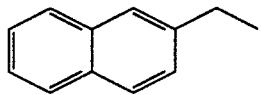 | $C_{61}H_{91}NO_7$ (949), 956 (M + Li⁺) |
The examples of Table 70 were obtained in analogy to Examples 610 and 611.

TABLE 70
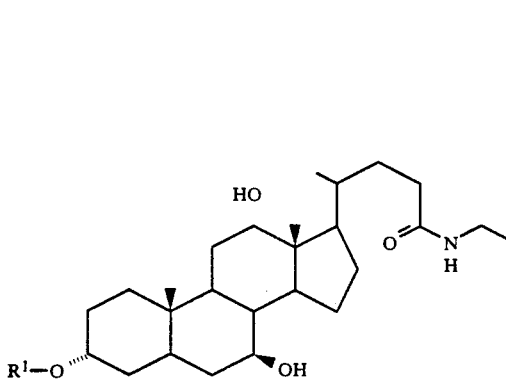
| Ex. | R[1] | MS (FAB, 3-NBA/LiCl or LiI) |
|---|---|---|
| 641 | H | $C_{50}H_{83}NO_7$ (809), 816 (M + Li$^+$). |
| 642 | 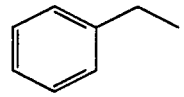 | $C_{57}H_{89}NO_7$ (899), 906 (M + Li$^+$) |
| 643 | 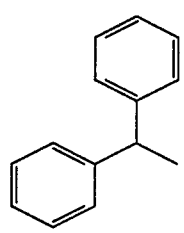 | $C_{63}H_{93}NO_7$ (975), 982 (M + Li$^+$) |
| 644 | 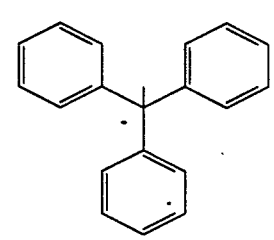 | $C_{59}H_{97}NO_7$ (1051), 1058 (M + Li$^+$) |
| 645 | 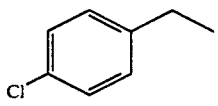 | $C_{57}H_{88}ClNO_7$ (933), 940 (M + Li$^+$) |
| 646 | 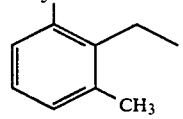 | $C_{59}H_{94}NO_7$ (928), 935 (M + Li$^+$) |
| 647 | 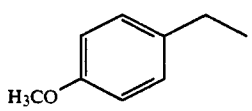 | $C_{58}H_{91}NO_8$ (929), 936 (M + Li$^+$) |
| 648 | 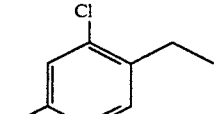 | $C_{57}H_{87}Cl_2NO_7$ (967), 904 (M + Li$^+$) |

TABLE 70-continued
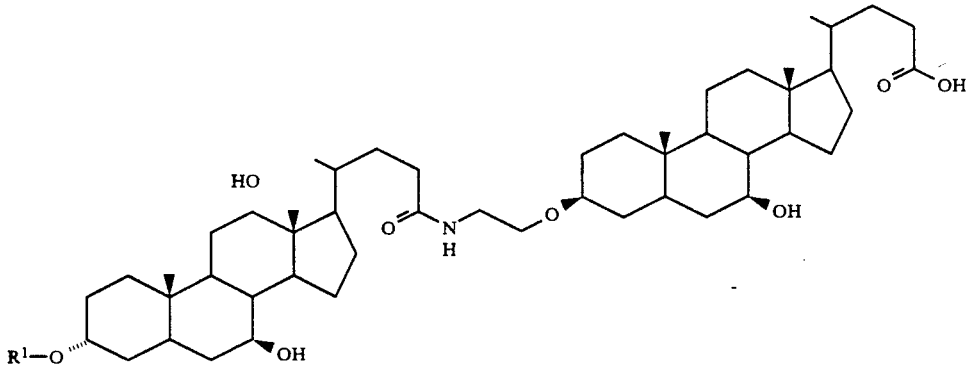
| Ex. | R¹ | MS (FAB, 3-NBA/LiCl or LiI |
|---|---|---|
| 649 | 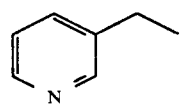 | $C_{56}H_{88}N_2O_7$ (900), 907 (M + Li⁺) |
| 650 | 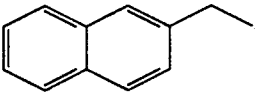 | $C_{51}H_{91}NO_7$ (949), 956 (M + Li⁺) |
The examples of Table 71 were obtained in analogy to Examples 610 and 611.
TABLE 71
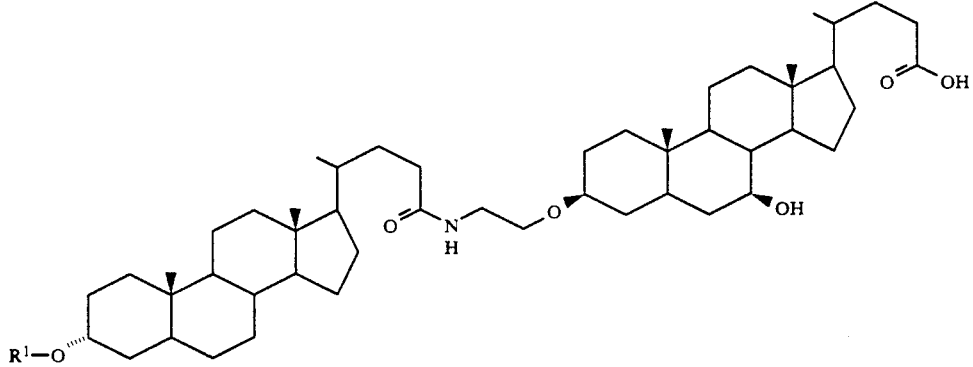
| Ex. | R¹ | MS (FAB, 3-NBA/LiCl or LiI |
|---|---|---|
| 651 | H | $C_{50}H_{83}NO_6$ (793), 800 (M +⁻Li⁺) |
| 652 | 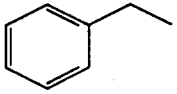 | $C_{57}H_{89}NO_6$ (883), 890 (M + Li⁺) |
| 653 | 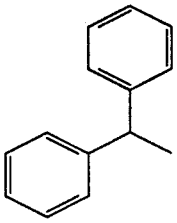 | $C_{63}H_{93}NO_6$ (959), 966 (M + Li⁺) |

TABLE 71-continued
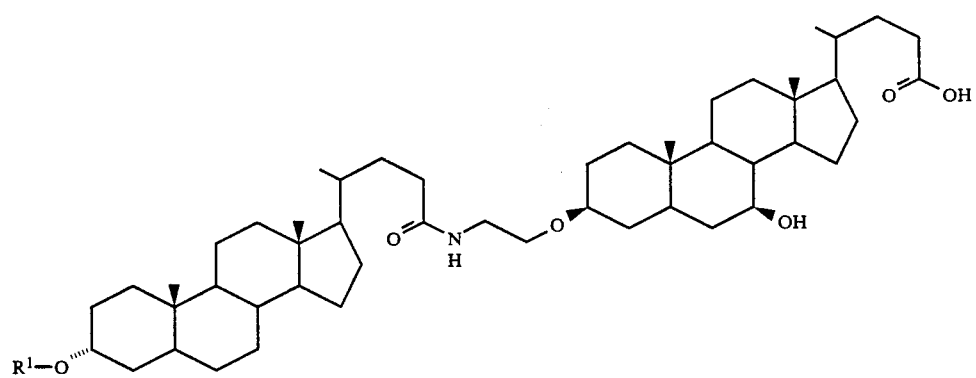
| Ex. | R¹ | MS (FAB, 3-NBA/LiCl or LiI |
|---|---|---|
| 654 | 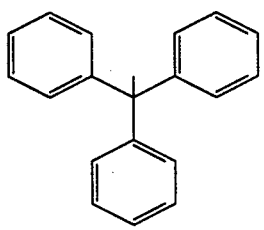 | $C_{69}H_{97}NO_6$ (1035), 1042 (M + Li$^+$) |
| 655 | 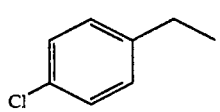 | $C_{57}H_{88}ClNO_6$ (917), 924 (M + Li$^+$) |
| 656 | 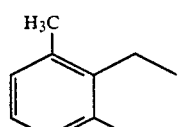 | $C_{59}H_{94}NO_6$ (912), 919 (M + Li$^+$) |
| 657 | 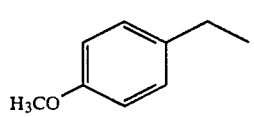 | $C_{58}H_{91}NO_7$ (913), 920 (M + Li$^+$) |
| 658 | 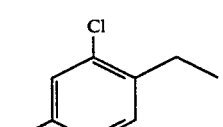 | $C_{57}H_{87}Cl_2NO_6$ (951), 958 (M + Li$^+$) |
| 659 | 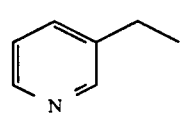 | $C_{56}H_{88}N_2O_6$ (884), 891 (M + Li$^+$) |
| 660 | 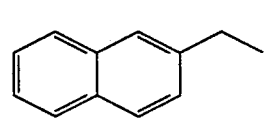 | $C_{81}H_{91}NO_6$ (933), 940 (M + Li$^+$) |

EXAMPLE 661

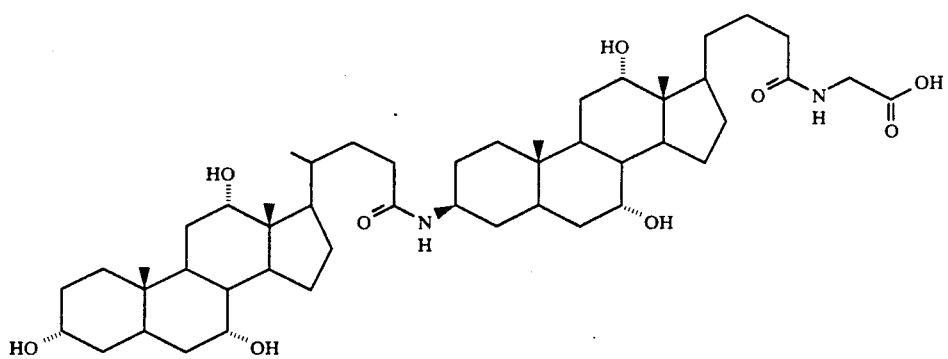

0.036 ml (0.38 mmol) of ethyl chloroformate was added dropwise at 0° C. to 200 mg (0.25 mmol) of Example 575 and 0.052 ml (0.38 mmol) of triethylamine in 30 ml of THF. After 15 min at 0° C., a solution of 66 mg (0.88 mmol) of glycine in 7.55 ml of 0.1M NaOH was added dropwise and the mixture was stirred at room temperature for a further 5 h. Saturated sodium dihydrogenphosphate solution was added and the mixture was extracted 3 times with THF. After drying and concentration of the organic phases, the residue was chromatographed on silica gel (CHCl$_3$/methanol/acetic acid 16:4:1). Yield 180 mg (84%) of "Example 6661".

$C_{50}H_{82}N_2O_9$ (854), MS (FAB, 3-NBA.LiCl): 861 (M+Li$^+$).

The examples of Tables 61-71 were converted into the corresponding glycine derivatives in analogy to Example 661.

EXAMPLE 662

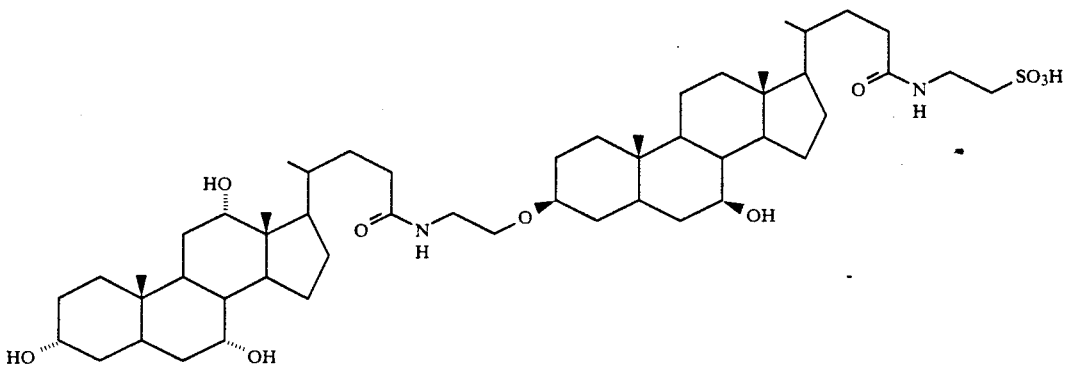

0.13 ml (1.36 mmol) of ethyl chloroformate was added dropwise at 0° C. to 300 mg (0.38 mmol) of Example 611 and 0.19 ml (1.38 mmol) of triethylamine in 50 ml of THF. After 15 min at 0°, a solution of 300 mg (2.4 mmol) of taurine in 12 ml of 1M NaOH was added. After 24 h at room temperature, the mixture was worked up as described for Example 661. 200 mg (59%) of "Example 662" were obtained.

$C_{52}H_{88}N_2$, $O_{10}S$ ( 932 MS (FAB, 3-NBA/LiCl): 939 (M+Li$^+$).

The examples of Tables 61-71 were converted into the corresponding taurine derivatives in analogy to Example 662.

EXAMPLE 663

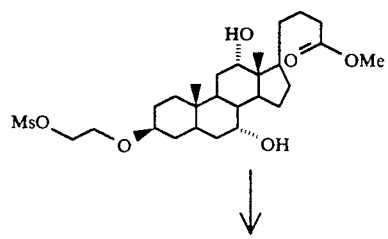

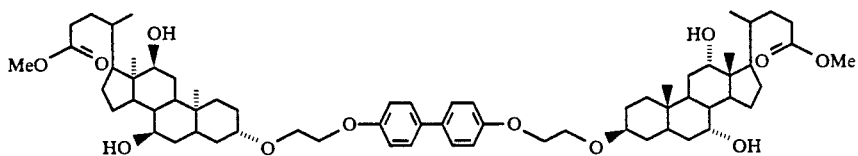

1.0 g (1.84 mmol) of Example 137, 170 mg (0.91 mmol) of 4,4'-dihydroxybiphenyl and 400 mg (2.9 mmol) of potassium carbonate were stirred at 60° C. for 5 h in 20 ml of DMSO. Water was added and the mixture was extracted with ethyl acetate. After drying and concentration of the organic phase, the residue was chromatographed on silica gel (cyclohexane/ethyl acetate 1:4). Yield 340 mg (34%) of "Example 663".

$C_{66}H_{99}O_{12}$ (1082), MS (FAB, 3-NBA/LiCl): 1089 (M+Li+).

EXAMPLE 664

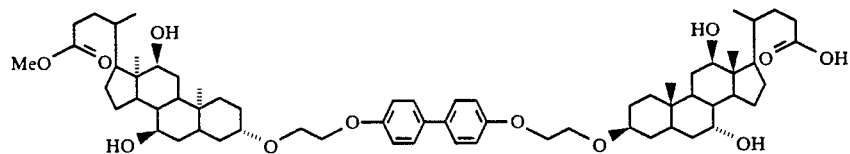

Example 663 was hydrolyzed by the process described for Example 575 to give "Example 664".

$C_{64}H_{94}O_{12}$ (1054) i, MS (FAB, 3-NBA/LiCl) 1061 (M+Li+)

EXAMPLE 665

530 mg (1.16 mmol) of methyl 3-amino-7,α12α-dihydroxycholate hydrochloride, 600 mg (1.19 mmol) of methyl 7,α12α-diacetoxy-3-ketocholate and 180 mg (2.86 mmol) of sodium cyanoborohydride were stirred at room temperature for 24 h in 30 ml of absolute methanol. The mixture was poured into water, brought to pH 9 with 0.1M NaOH and extracted with ethyl acetate. The organic phases were dried and concentrated. Chromatography on silica gel (cyclohexane/ethyl acetate/triethylamine 50:50:2) gave 360 mg (34 %) of "Example 665".

$C_{54}H_{87}NO_{10}$ (909), MS (FAB, 4-NBA/LiCl) : 916 (M+Li+).

EXAMPLE 666

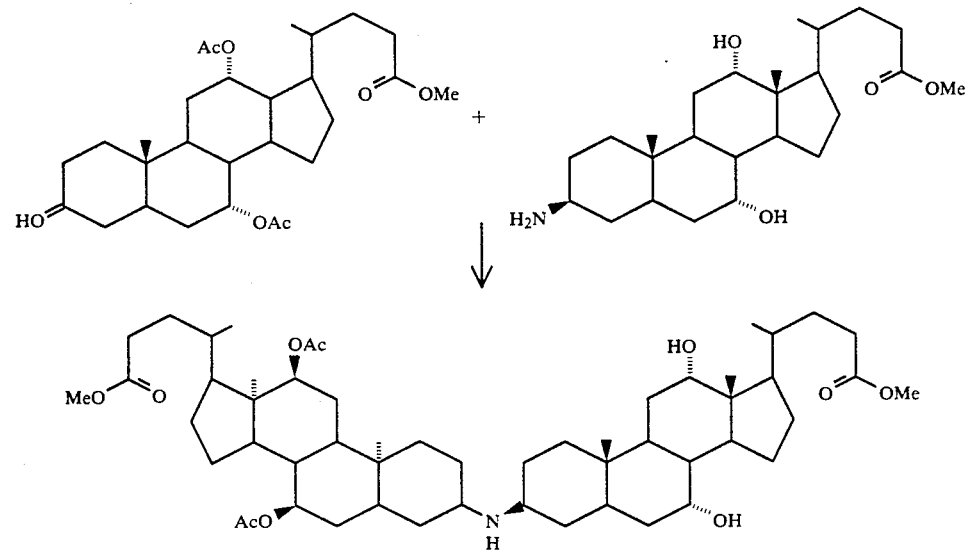

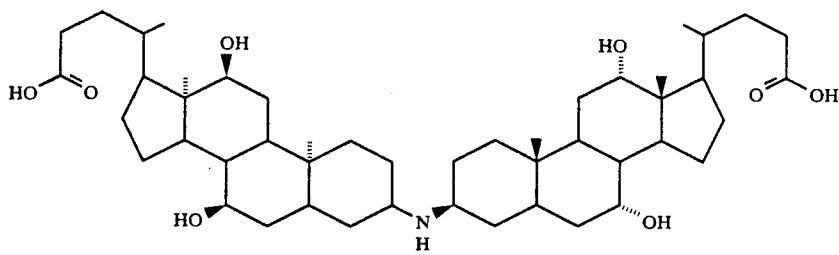

200 mg (0.22 mmol) of Example 665 were heated under reflux for 3 h in 5 ml of ethanol/10 ml of 5M NaOH. The alcohol was then evaporated, the residue was acidified with 1M HCl and the resulting precipitate was filtered off with suction and dried. 170 mg (97%) of "Example 6666" were obtained.

$C_{49}H_{79}NO_9$ (797), MS (FAB, 3-NBA/LiCl): 804 (M+Li$^+$).

EXAMPLE 667

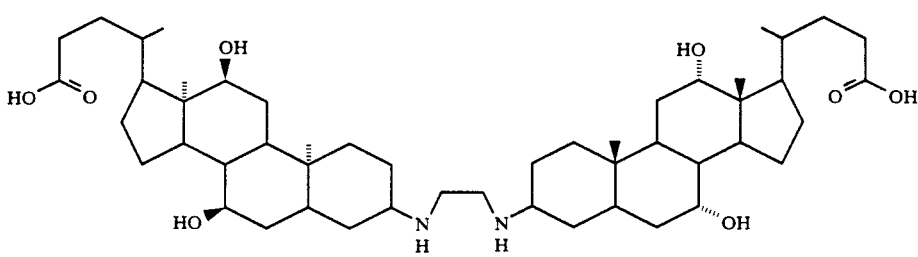

1.0 g (1-98 mmol) of methyl 7α, 12α-diacetoxy-3-ketocholate, 130 mg (0.98 mmol) of 1,2-diaminoethane dihydrochloride and 300 mg (4.8 mmol) of sodium cyanoborohydride were reacted according to the process described for Example 665. 740 mg (71%) of "Example 667", were obtained.

$C_{58}H_{91}NO_{12}$ (993), MS (FAB, 3-NBA/LiCl) 1000 (M+Li$^+$)

EXAMPLE 668

200 mg (1.93 mmol) of Example 667 were hydrolyzed as described for Example 666. 140 mg (86%) of "Example 668" were obtained.

$C_{50}H_{84}N_2O_9$ (840), MS (FAB, 3-NBA/LiCl):847 (M+Li$^+$)

The examples of Table 72 were obtained analogously to Examples 667 and 668.

TABLE 72

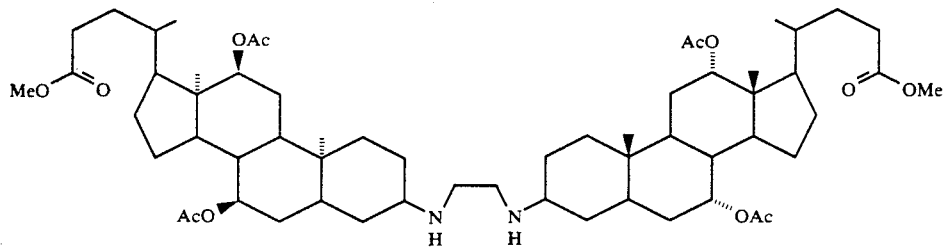

| Ex. | X | MS (FAB, 3-NBA/LiCl or LiI |
|---|---|---|
| 669 | —(CH$_2$)$_3$— | $C_{51}H_{86}N_2O_8$ (854), 861 (M + Li$^+$) |
| 670 | —(CH$_2$)$_6$— | $C_{54}H_{92}N_2O_8$ (896), 903 (M + Li$^+$) |
| 671 | —(CH$_2$)$_{12}$— | $C_{60}H_{104}N_2O_8$ (980), 987 (M + Li$^+$) |
| 672 | —(CH$_2$)$_2$—O—(CH$_2$)$_2$— | $C_{52}H_{88}N_2O_9$ (884), 891 (M + Li$^+$) |

Example 673

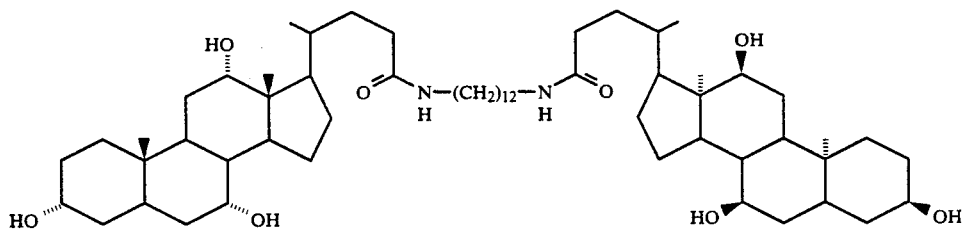

4.09 g (9.8 mmol) of cholic acid, 1.0 g (5 mmol) of 1,12-diaminododecane and 2.46 g (10 mmol) of 2-ethoxy-1-ethoxycarbonyl-1,2-dihydroquinoline were heated under reflux for 3 h in 80 ml of toluene. The solvent was evaporated and the residue was chromatographed on silica gel (chloroform/methanol 6:1). Yield 3.0 g (63%) of "Example 673".

$C_{60}H_{104}N_2O_2$ (980), MS (FAB, 3-NBA/LiCl) : 987 (M+Li$^+$)

The examples of Table 73 were obtained analogously to Example 673.

TABLE 73

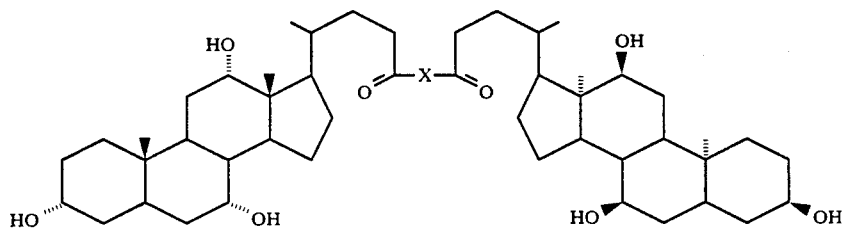

| Ex. | | MS (FAB, 3-NBA/LiCl or LiI |
|---|---|---|
| 674 | —N(H)—(CH$_2$)$_3$—N(H)— | $C_{51}H_{88}N_2O_8$ (856), 863 (M + Li$^+$) |
| 675 | —N(H)—(CH$_2$)$_6$—N(H)— | $C_{54}H_{94}N_2O_6$ (898), 905 (M + Li$^+$) |
| 676 | \N(H)—(CH$_2$)$_3$—N(H)—C(O)—(CH$_2$)$_2$—C(O)—N(H)—(CH$_2$)$_3$—N(H)/ | $C_{58}H_{100}N_4O_{10}$ (1012), 1019 (M + Li$^+$) |
| 677 | \N(H)—CH$_2$CH$_2$—O—CH$_2$CH$_2$—O—CH$_2$CH$_2$—O—CH$_2$CH$_2$—N(H)/ | $C_{56}H_{98}N_2O_{11}$ (974), 981 (M + Li$^+$) |

EXAMPLE 678

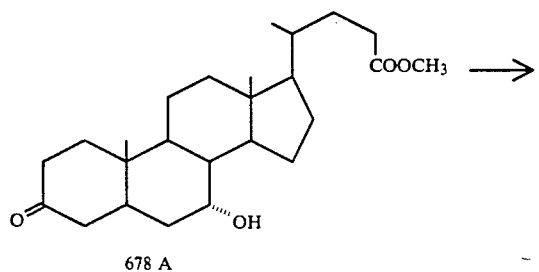
678 A

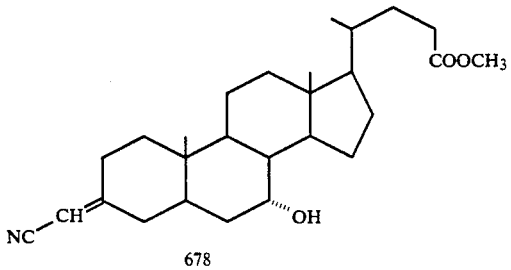
678

2.2 g (0.055 mol) of 60 sodium hydride suspension were added under argon to 150 ml of dry methanol. 9 ml (0.055 mol) of diethyl cyanomethanephosphonate in 50 ml of methanol are added dropwise with cooling to this mixture. After 1 h at room temperature, 20.7 g (0.05 mol) of 678 A in 300 ml of methanol are added to this mixture and it is stirred at room temperature for 1-2 h with TLC checking. The mixture is concentrated in the cold and then partitioned between water and dichloromethane. After separation, it is extracted with dichloromethane, and the organic phase is washed, dried and concentrated. The residue is purified by chromatography on SiO$_2$. Yield: 17.5 g (82%) of 678 MS (FAB, 3-NBA, LiCl): 434 (M+Li$^+$)

EXAMPLE 679

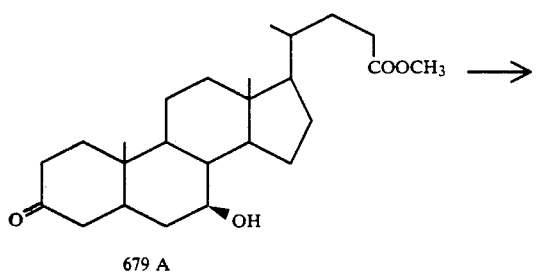

679 A

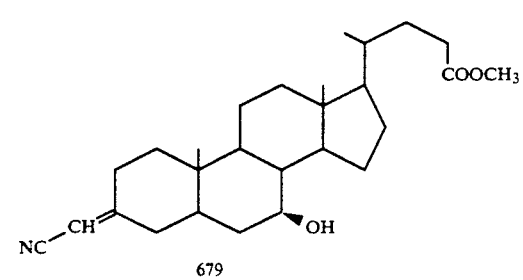

679

Analogously to 678 from 679 A. Yield 49% MS (FAB, 3-NBA, LiCl): 434 (M+Li+)

After chromatography, a double bond isomer product 679 B of identical molecular weight is obtained in 43% yield, which leads in the hydrogenation described below to the same product as 679.

EXAMPLE 680

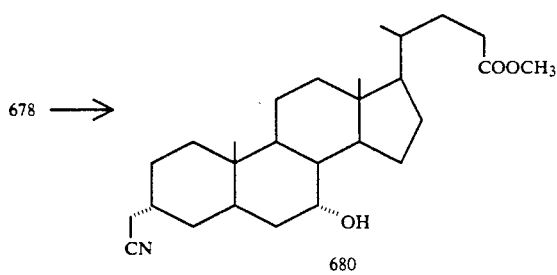

680

15 g (0.035 mol) of 678 were dissolved in 500 ml of methanol and hydrogenated in a duck-shaped shaking apparatus at room temperature with the addition of 5 g of 10% palladium-carbon. The catalyst is separated off, the is filtrate is concentrated and the residue is chromatographed on SiO$_2$. Yield 13.7 g (91%) of 680 (3α-isomer according to analysis of 684)

MS (FAB, 3-NBA, LiCl): 436 (M+Li+).

EXAMPLE 681

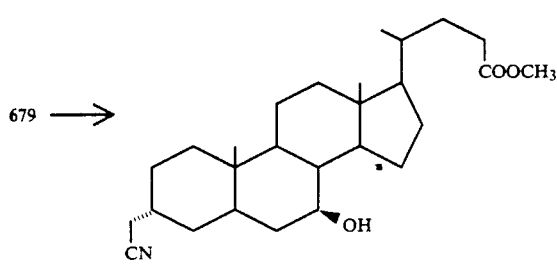

Analogously to 680 from 679. Yield 85% MS (FAB, 3-NBA, LiCl): 436 (M+Li+) (3α-isomer according to information from 685)

EXAMPLE 682

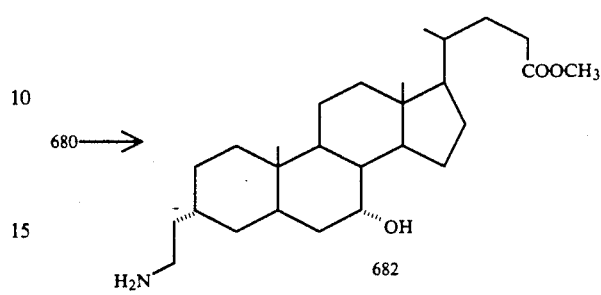

682

12 g (0.028 mol) of 680 are dissolved in 300 ml of methanol and hydrogenated for 24 h at 20 bar and at room temperature with the addition of 30 ml of concentrated ammonia solution and 3.5 g of 5% rhodium on Al$_2$O$_3$. 682 is obtained after removal of the catalyst, concentration and chromatography of the residue (SiO$_2$). Yield 9.8 g (81%) MS (FAB, 3-NBA, LiCl): 440 (M+Li+) 434 (M+H+) (3α-isomer according to analysis of 684).

EXAMPLE 683

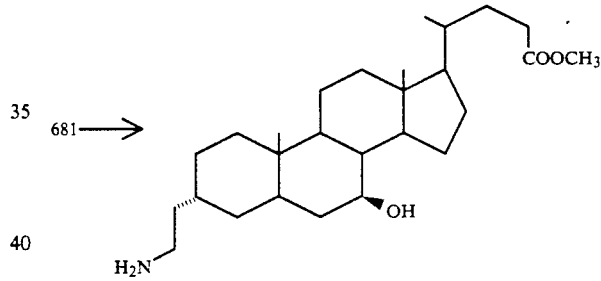

Analogously to 682 from 681. Yield 6.1 g (67%) MS (FAB, 3-NBA, LiCl): 440 (M+Li++) , 434 (M+H) (3α-isomer according to analysis of 685).

EXAMPLE 684

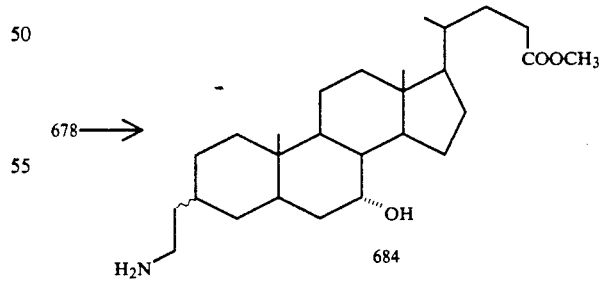

684

15 g (0.035 mol) of 678 are dissolved in 50 ml of methanol and hydrogenated for 24 h at 25 bar and at room temperature with the addition of 50 ml of conc. ammonia solution and 4 g of 5% rhodium Al$_2$O$_3$. After working up as in on 682, a crude product results which is purified by chromatography on SiO$_2$ using dichloromethane/methanol/conc. ammonia solution=100:15:5. 6.4 g (42%) of less polar 3β-684 and 4.2 g (27.6%) of more polar 3α684 are obtained. MS(FAB, 3-NBA, LiCl): 440 (M+Li+), 424 (M+E). Thin layer chromatographic comparison with 682 shows identity with 3α-684 and difference from 3β-684.

EXAMPLE 685

679 ⟶

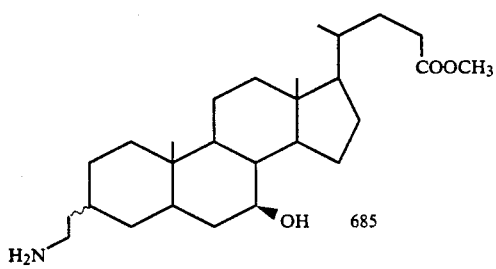

685

Analogously to 684 from 679. Yield 35 of (less polar) 3β-685 and 29% of (more polar) 3α-685. TLC comparison with 683 shows identity with 3α-685.

MS (FAB, 3-NBA, LiCl):440 (M+Li+), 434 (M+H+)

Example 686

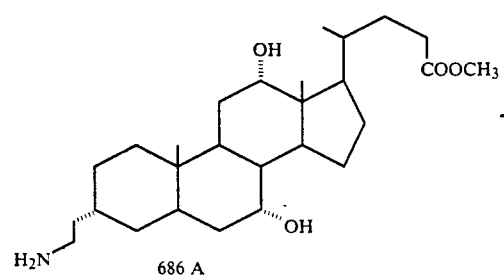

686 A 899.4 mg (2 mmol) of amine 678 are dissolved in 15 ml of dioxane/water=2/1 and treated with 5 ml of 1N NaOH with ice-cooling. 480 mg (2.2 mmol) of di-tert-butyl pyrocarbonate are added to this mixture at 0° C. and it is subsequently stirred at room temperature for 30 min. After reaction is complete, dioxane is removed in vacuo, and the aqueous phase is covered with a layer of ethyl acetate and acidified to pB 2 with dilute KHSO4 solution with ice-cooling. Neutral material is extracted, dried and concentrated, and the residue is purified by chromatography on SiO2. Yield 792 mg (72%) of Example 686, MS (FAB, 3-NBA, LiCl): 556 (M+Li+).

EXAMPLE 687

686 ⟶

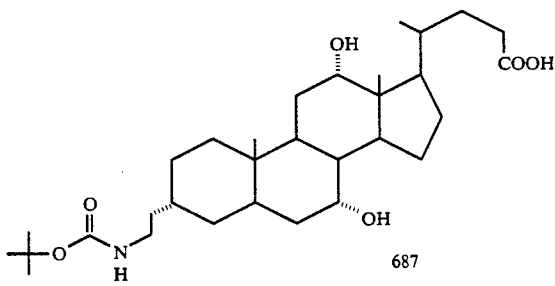

687

2.75 g (5 mmol) of 686 are dissolved in 20 ml of methanol and stirred at room temperature overnight with 2 ml of 2N NaOH. The mixture is diluted with water, methanol is removed in vacuo and the mixture is acidified by dropwise addition of KHSO4 solution until a precipitate is formed. The precipitate is filtered off with suction and the residue is filtered through SiO2. Yield 1.79 g (67%) of 687. MS (FAB, 3-NBA, LiCl): 543 (M+Li+).

EXAMPLE 688

687 ⟶

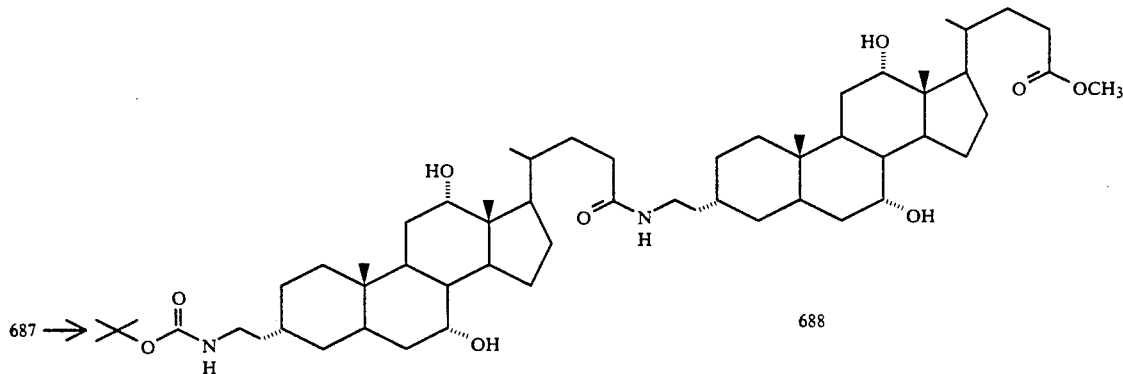

688

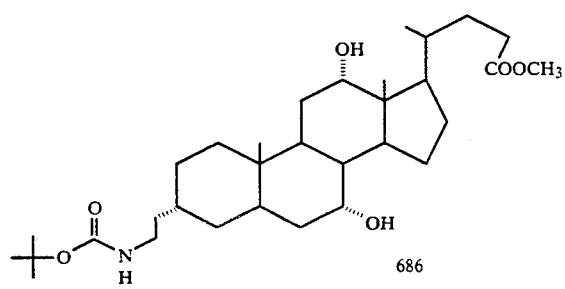

686

1.35 g (3 mmol) of 686 A are dissolved in 50 ml of ethyl acetate and 0.5 ml of triethylamine is added. 0.85 g of ethyl 1,2-dihydro-2-ethoxyquinoline-1-carboxylate (EEDQ) and 1.6 g (3 mmol) of 687 are added to this mixture and it is stirred under reflux for 4-5 h. After reaction is complete, the mixture is diluted with ethyl acetate, washed with saturated potassium hydrogensulphate solution and water, dried and concentrated, and the residue is chromatographed on SiO2. Yield 2.46 g (85 of 688.

221
MS (FAB, 3-NBA, LiCl): 974 (M+Li+).
222
MS (FAB, 3-NBA, LiCl): 944 (M+Li+)
EXAMPLE 689
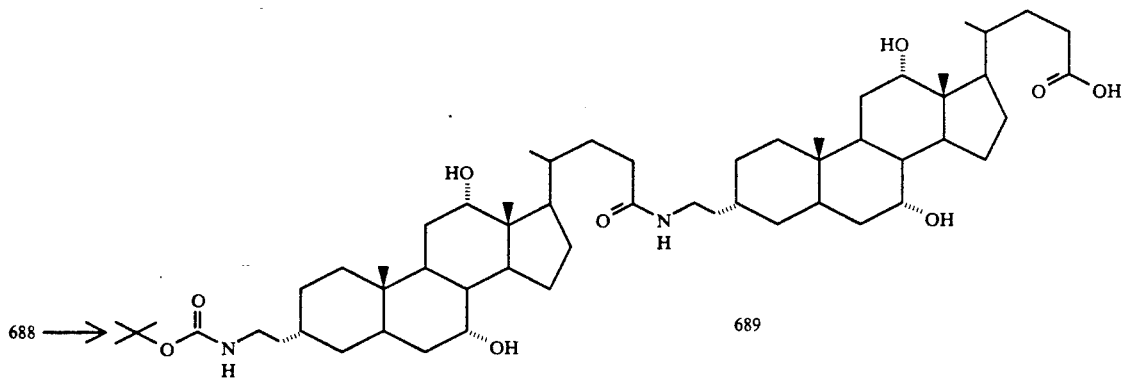
2 g (2.07 mmol) of 688 are hydrolyzed with 2 ml of 2N NaOH in 20 ml of methanol as described under 687.
Yield 1.66 g (84%) of 689. MS (FAB, 3-NBA, LiCl): 960 (M+Li+) The following examples are prepared analogously to the reaction sequence 686 A→686→687→688→689:
EXAMPLE 690 FROM 682
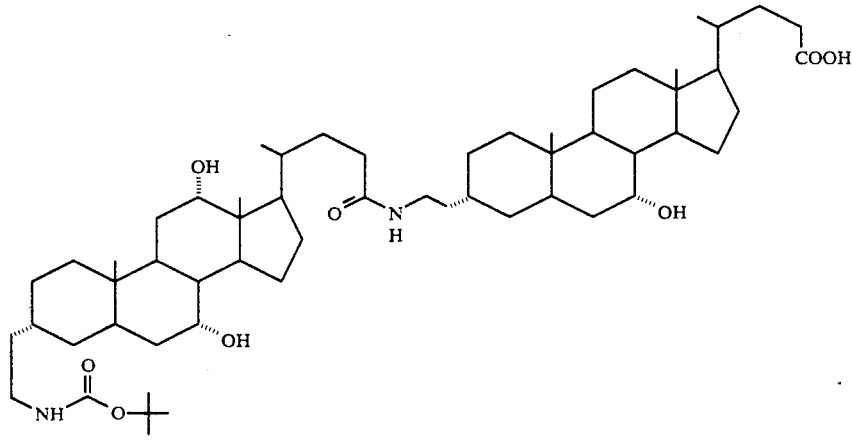
MS (FAB, 3-NBA, LiCl): 944 (M+Li+)
EXAMPLES 691 FROM 683
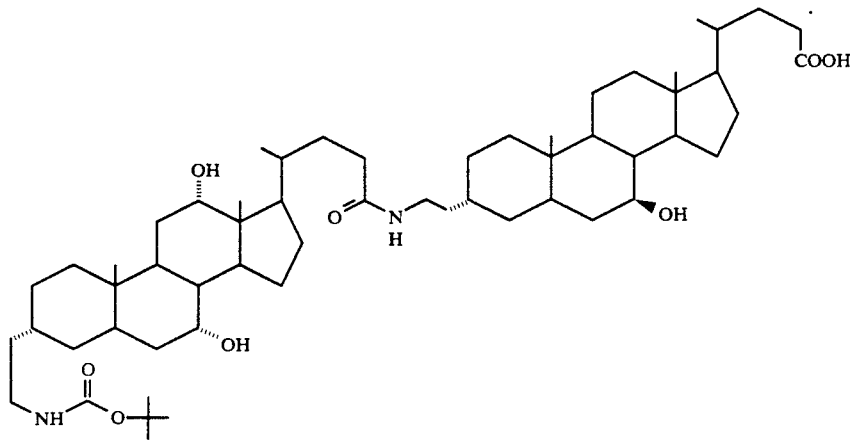

EXAMPLE 692

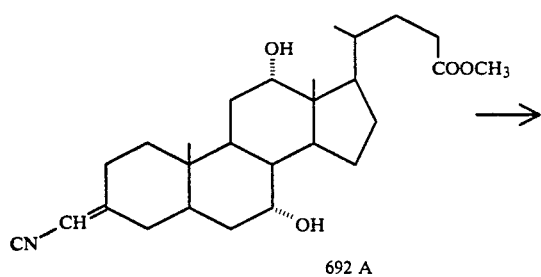

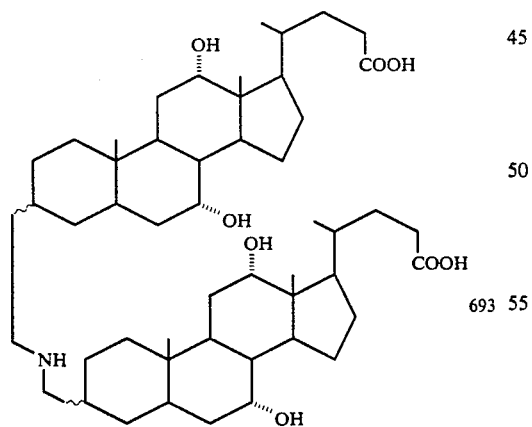

30 g (0.067 mol) of 692 A are dissolved in 1 l methanol and hydrogenated analogously to Example 684. In addition to the main products, chromatographic separation of the crude product yields 1.28 g (4.3%) of 692

MS (FAB, 3-NBA, LiCl): 889 (M+Li$^{30}$)

EXAMPLE 693

692 ⟶

1.2 g (1.36 mmol) of 692 are dissolved in 10 ml of methanol and are hydrolyzed by stirring overnight with 1 ml of 2N NaOH. The mixture is diluted with water, methanol is removed in vacuo and the product is precipitated by addition of 2N HCl. The crude product is purified by column filtration. Yield 0.96 (83%) of 693.

MS (FAB, 3-NBA, LiCl): 861 (M+Li$^+$)

EXAMPLE 694

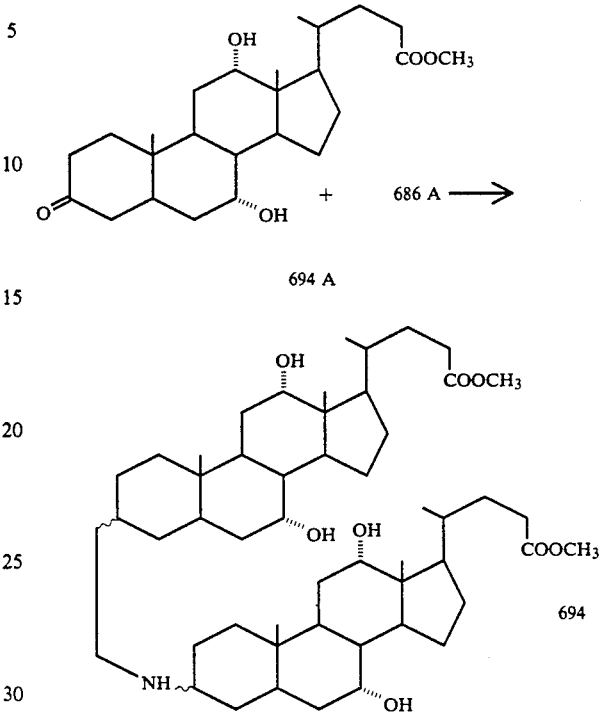

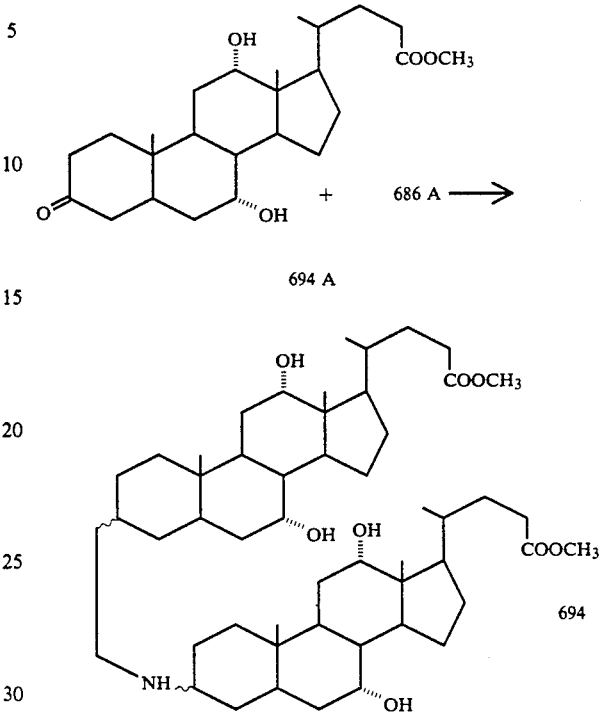

449 mg (1 mmol) of 686A are dissolved in 15 ml of dry methanol. 420 mg (1 mmol) of 694A and 80 mg (1.3 mmol) of sodium cyanoborozhydride are added to this mixture and it is stirred overnight at room temperature. It is then concentrated, the residue is partitioned between water and dichloromethane and the residue of the organic phase is purified by chromatography (SiO$_2$).

Yield: 450 (53%) of 694. MS (FAB, 3-NBA, LiCl): 861 (M+Li$^+$)

EXAMPLE 695

694 ⟶

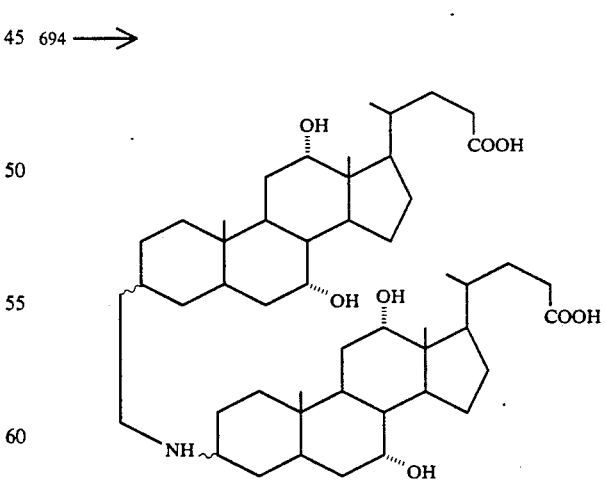

200 mg (0.23 mmol) of 694 are dissolved in 5 ml of methanol and hydrolyzed with 0.5 ml of 2N NaOH as described under 693. Yield 180 mg (95%) of 695. MS (FAB, 3-NBA, LiCl): 823 (M+Li$^+$), 827 (M+H$^+$)

EXAMPLE 696

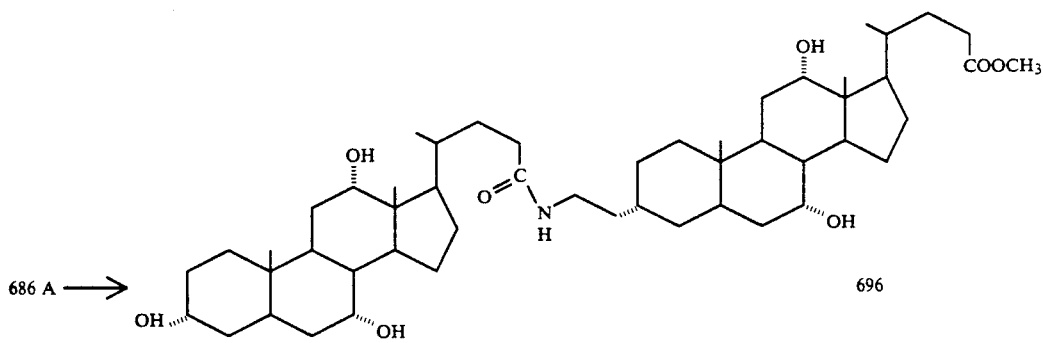

0.15 ml of triethylamine, 273 mg (1.1 mol) of EEDQ and 408 mg (1 mmol) of cholic acid are added to 449 mg (1 mmol) of 686 A in 30 ml of dry ethyl acetate and the mixture is heated to reflux for 4 h. After reaction is complete, the mixture is diluted with about 100 ml of ethyl acetate and washed with $KHSO_4$ solution, and the residue of the organic phase is purified by chromatography. Yield 597 mg (71%) of 696

MS (FAB, 3-NBA, LiCl): 847 (M+Li+)

EXAMPLE 697

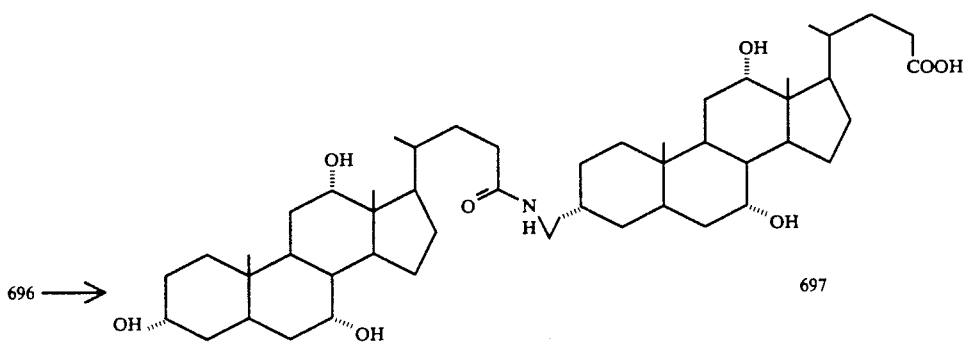

500 mg (0.6 mmol) of 696 are hydrolyzed with 1.5 ml of 2N NaOH in 15 ml of ethanol as described under 693. Yield 452 mg (91%) of 697 MS (FAB, 3-NBA, LiCl): 883 (M+Li+)

EXAMPLE 698

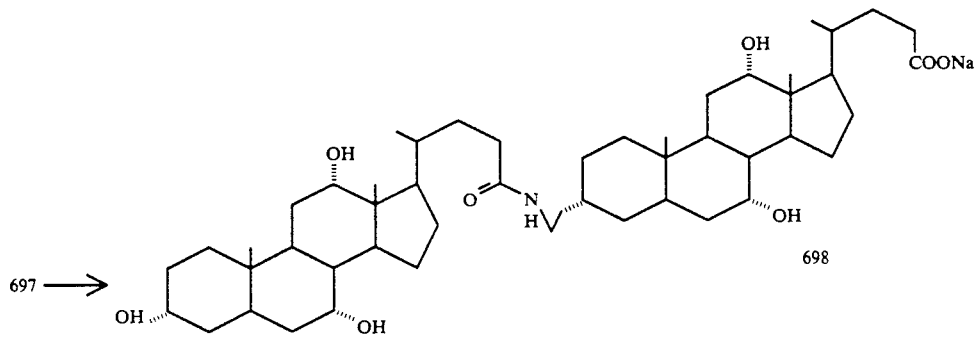

413 mg (0.5 mmol) of 697 are dissolved in 3-5 ml of dry methanol and treated with one equivalent of a 1M solution of NaOH in methanol. The sodium salt 698 is precipitated by addition of dry ether, then filtered off with suction and dried. Yield 390 mg (92%) of 698.

MS (FAB, 3-NBA): 849 (M+E+)

The following example substances (699 to 713) are prepared analogously to the reaction sequence 686 A→696→697

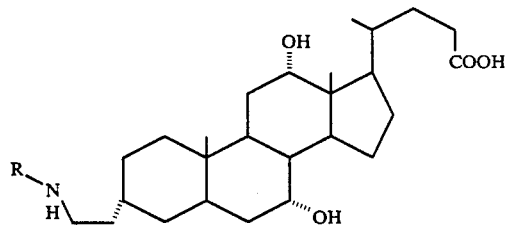
| Ex. | R | Starting materials: 686 A + | MS (FAB, 3-NBA, or LiI |
|---|---|---|---|
| 699 | 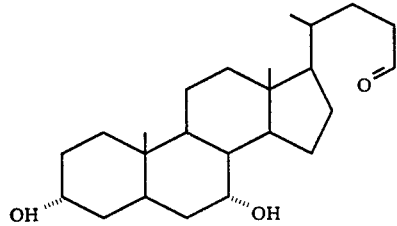 | Chenodeoxycholic acid | 817 (M + Li$^+$) |
| 700 | 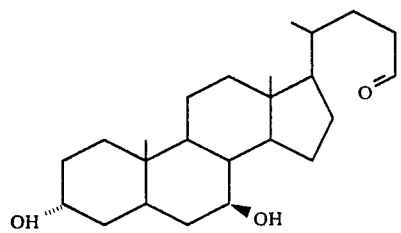 | Ursodeoxycholic acid | 817 (M + Li$^+$) |
| Ex. | R | Starting materials 686 A + | MS (FAB, 3-NBA, LiCl) |
|---|---|---|---|
| 701 | 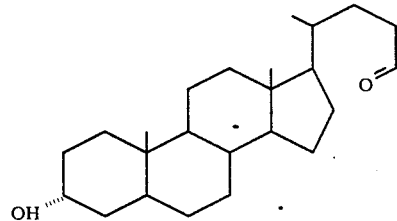 | Lithocholic Acid | 801 (M + Li$^+$) |
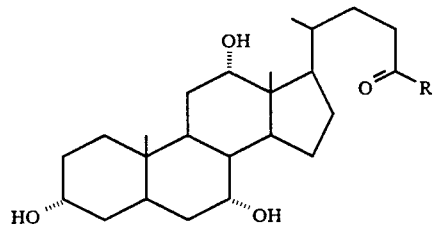
| Ex. | R | Starting materials: cholic acid + | MS (FAB, 3-NBA, LiCl) |
|---|---|---|---|
| 702 | 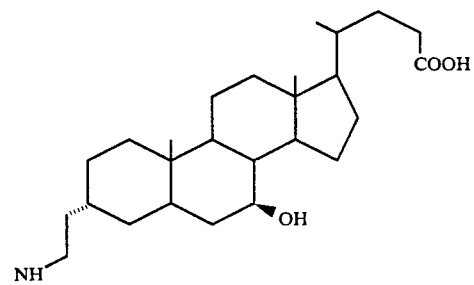 | 682 | 817 (M + Li$^+$) |

-continued
| 703 | | 683 | 817 (M + Li⁺) |
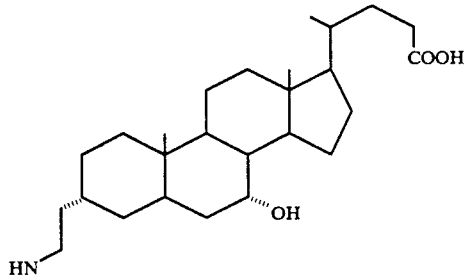
EXAMPLE 704
from ursodeoxycholic acid+683
MS (FAB, 3-NBA, LiCl): 801 (M+Li⁺)
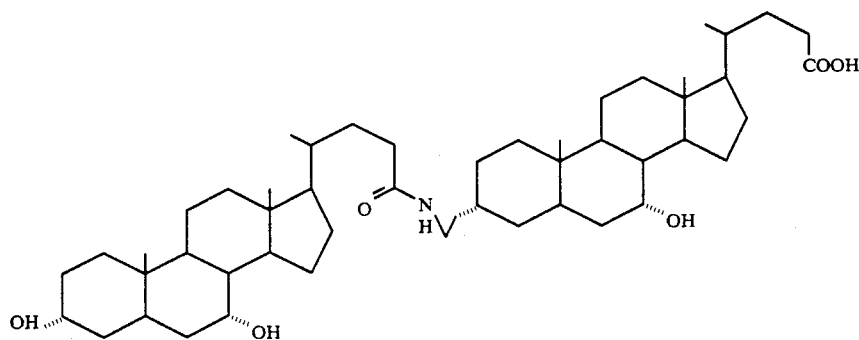
from chenodeoxycholic acid+682
MS (FAB, 3-NBA, LiCl): 801 (M+Li⁺)
EXAMPLE 706
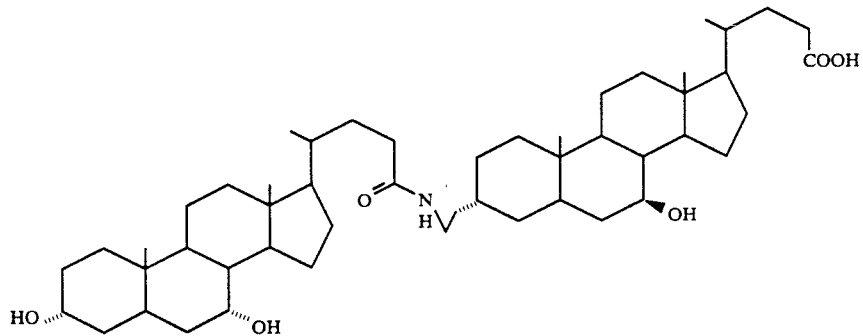
EXAMPLE 705
from ursodeoxycholic acid+682
MS (FAB, 3-NBA, LiCl): 801 (M+Li⁺)
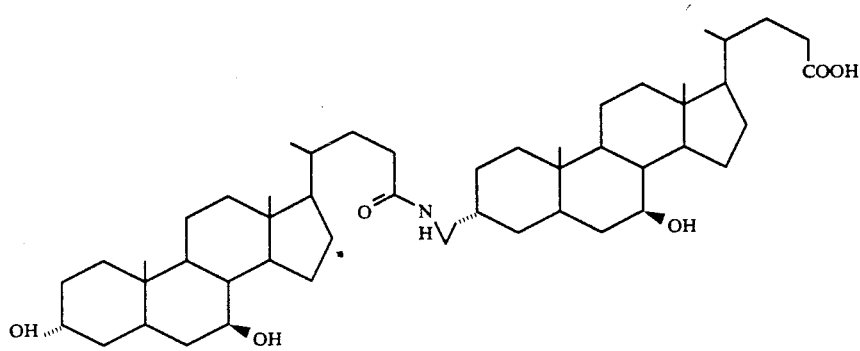

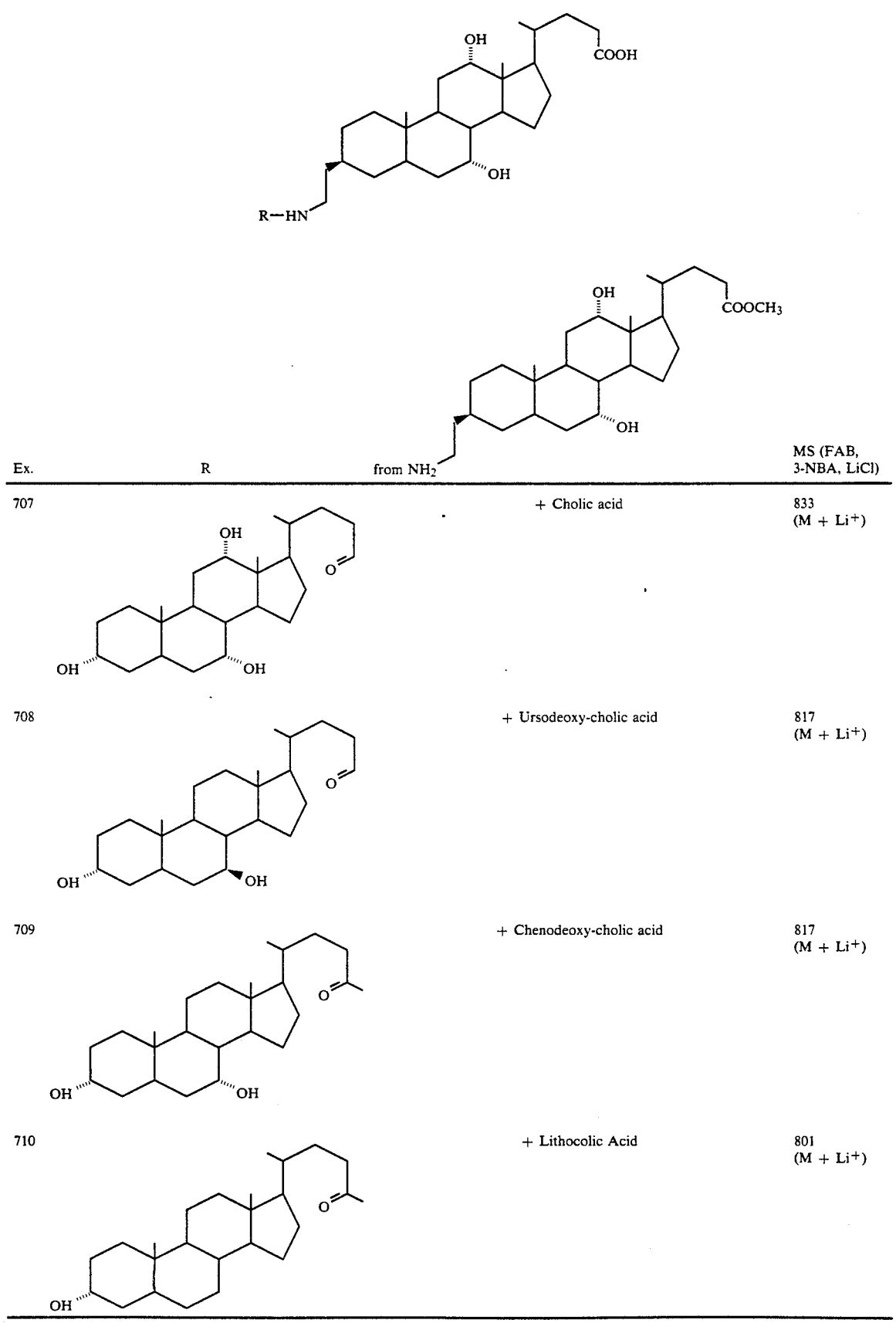

EXAMPLE 711
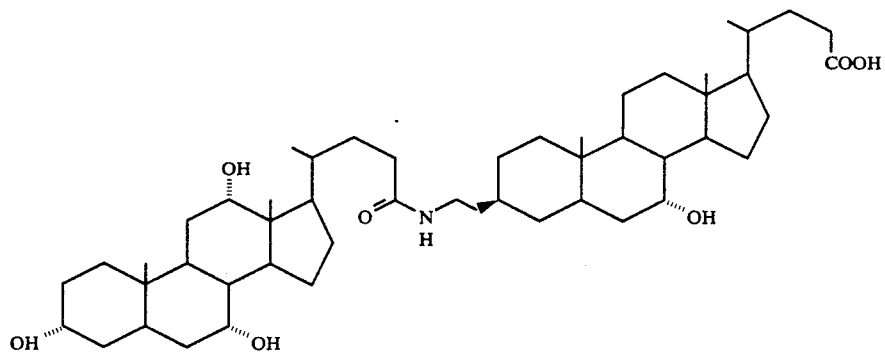
From cholic acid + 3β-684 MS (FAB, 3-NBA, LiCl): 817 (M+Li+)
EXAMPLE 712
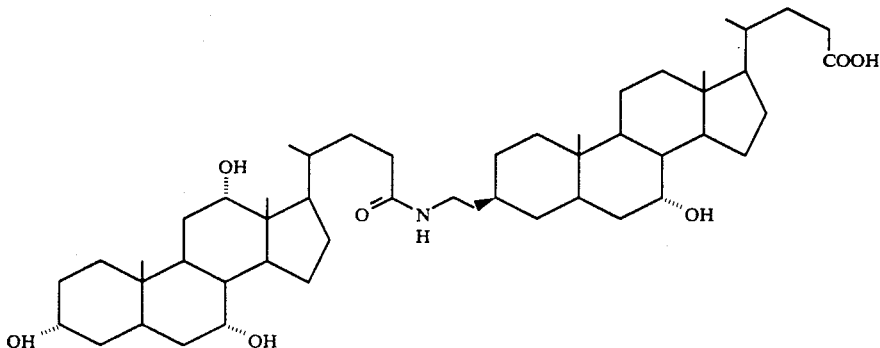
From cholic acid + 3β-685 MS (FAB, 3-NBA, LiCl): 817 (M+Li+)
EXAMPLE 713
From ursodeoxycholic acid + 3β-685 MS (FAB, 3-NBA, LiCl): 801 (M+Li+)
EXAMPLE 714
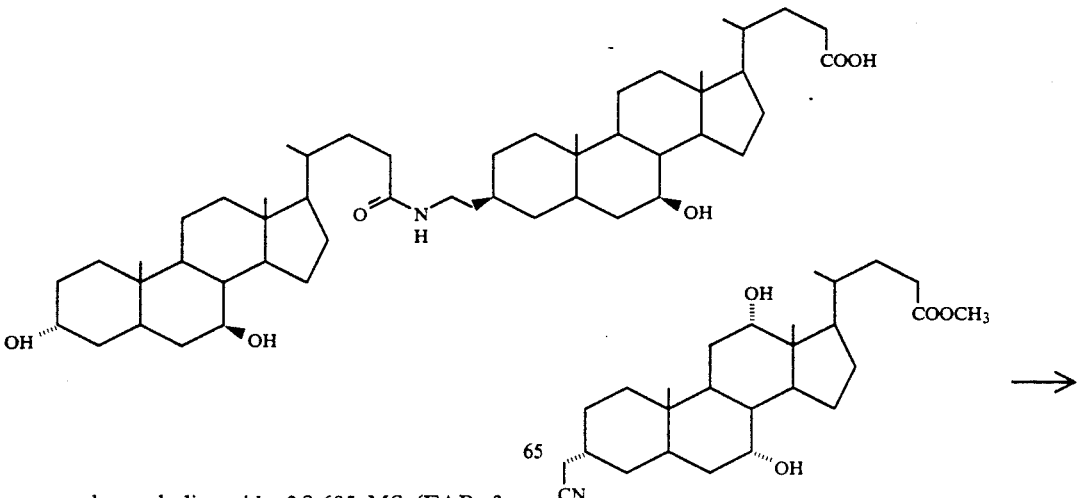
714 A →

-continued

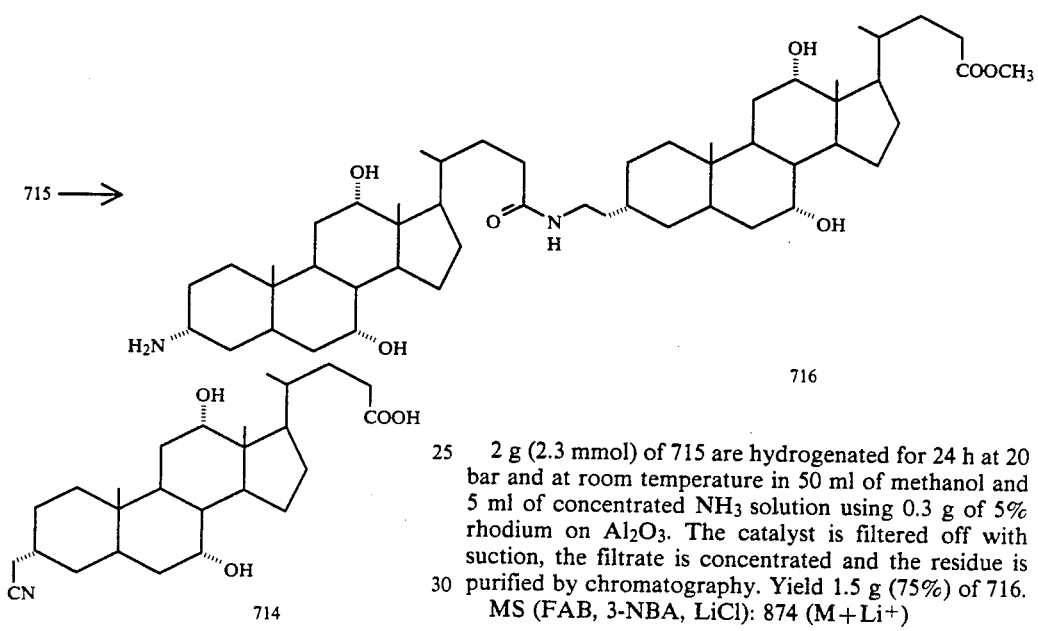

446 mg (1 mmol) of 714 A were hydrolyzed by stirring overnight with 2 ml of half-concentrated sodium hydroxide solution in 40 ml of ethanol. The mixture is diluted with water, ethanol is removed in vacuo and 714 is precipitated by acidification with dilute hydrochloric acid. The product is filtered off with suction, washed with water and dried. Yield: 420 mg (97%).
MS (FAB, 3-NBA, LiCl): 438 (M+Li+)

EXAMPLE 715

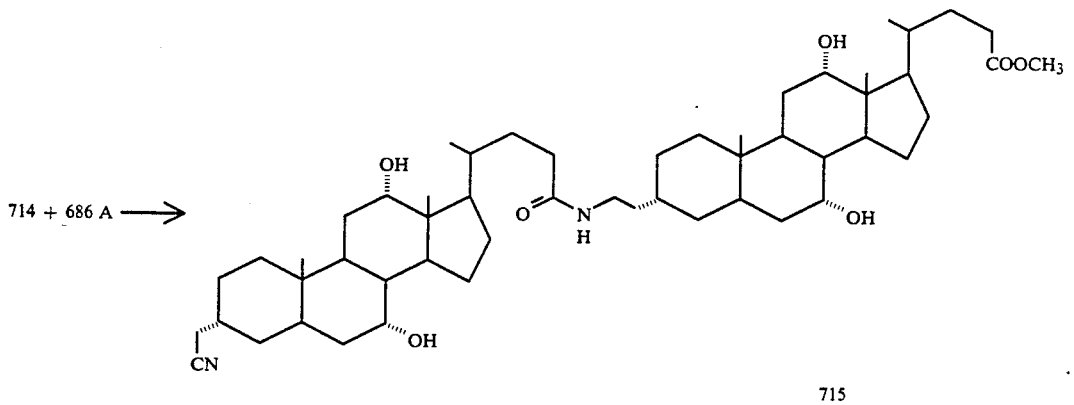

449 mg (1 mmol) of 686 A were dissolved in 30 ml of dry THF and 0.14 ml of triethylamine and 1.1 mol of EEDQ were added. 432 mg (1 mmol) of 714 are added to this mixture and it is heated to reflux for 6 h. After reaction is complete it is concentrated, taken up with ethyl acetate and washed with KHSO₄ solution and water. The residue of the organic phase is purified by chromatography. 587 mg (68%) of 715 are obtained.
MS (FAB, 3-NBA, LiCl): 870 (M+Li+)

EXAMPLE 716

2 g (2.3 mmol) of 715 are hydrogenated for 24 h at 20 bar and at room temperature in 50 ml of methanol and 5 ml of concentrated NH₃ solution using 0.3 g of 5% rhodium on Al₂O₃. The catalyst is filtered off with suction, the filtrate is concentrated and the residue is purified by chromatography. Yield 1.5 g (75%) of 716.
MS (FAB, 3-NBA, LiCl): 874 (M+Li+)

EXAMPLE 716B

699→716

484 mg (0.5 mmol) of 688 were added to a mixture of 25 ml of methanol in 1.5 ml of acetyl chloride prepared with cooling and the mixture was stirred at room temperature (checking of reaction by thin layer chromatography (TLC)) for 2 h. After reaction is complete, the mixture is neutralized with concentrated NH₃ solution and concentrated in vacuo, and the residue is purified by chromatography (SiO₂). 247 mg (58%) of 716 are obtained, identical to the substance prepared according to a) by TLC and MS.

EXAMPLE 717

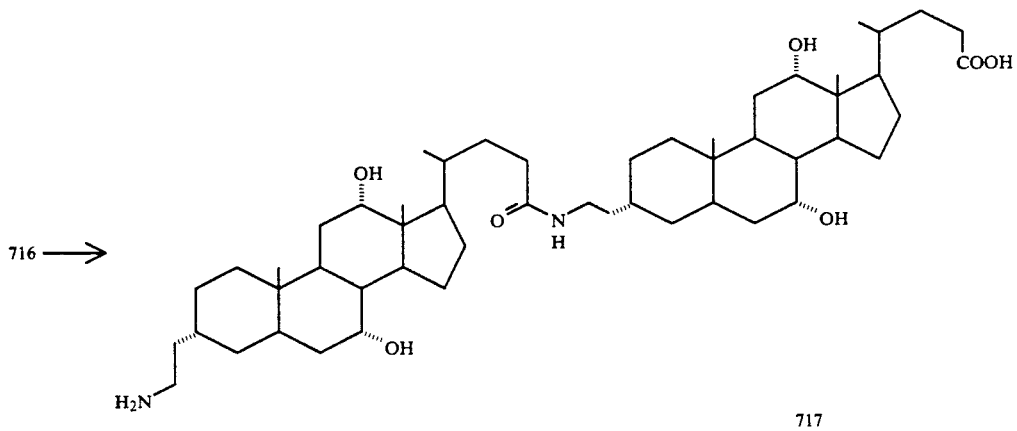

1.2 g (1.38 mmol) of 716 are dissolved in 20 ml of methanol and hydrolyzed by stirring overnight with 2 ml of half-concentrated sodium hydroxide solution. The mixture is diluted with water, methanol is removed in vacuo and the amino acid 717 is precipitated by careful acidification. The precipitate is filtered off with suction, washed with water and dried. Yield 1.1 g (93%).

MS (FAB, 3-NBA, LiCl): 860 (M+Li$^+$).

The following example substances (718→725) are prepared analogously to the reaction sequence (714 A)→714→715→716→717.

| Ex. | G1 | G2 | Starting Materials | MS (FAB, 3-NBA, LiCl or LiI |
|-----|----|----|--------------------|------------------------------|
| 718 | | | 714 + 686 B | 860 (M + Li$^+$) |
| 719 | | | 681 + 686 A | 844 (M + Li$^+$) |
| 720 | | | 680 + 686 B | 844 (M + Li$^+$) |

-continued
G1—NH—G2
| Ex. | G1 | G2 | Starting Materials | MS (FAB, 3-NBA, LiCl or LiI) |
|---|---|---|---|---|
| 721 | | | 714 + 683 | 844 (M + Li+) |
| 722 | | | 714 + 682 | 844 (M + Li+) |
| 723 | | | 681 + 683 | 828 (M + Li+) |
EXAMPLE 724
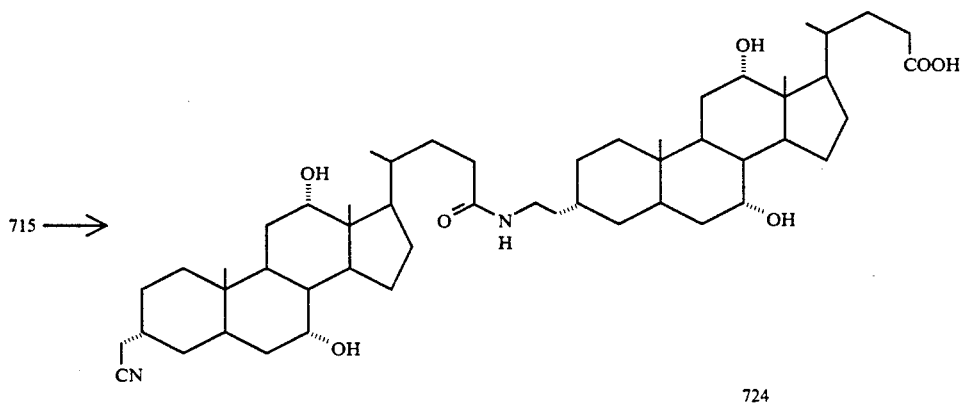
724
432 mg (0.5 mmol) of 715 are hydrolyzed with 1.5 ml of 12N NaOH in 15 ml of methanol as described under 717. Yield 318 mg (75%) of 724.
MS (FAB, 3-NBA, LiCl): 856 (M+Li+).
The following example substances (725→729) are prepared analogously to the reaction sequence 714→715→724:

G1—NH—G2

| Ex. | G1 | G2 | Starting materials | MS (FAB, 3-NBA LiCl) |
|---|---|---|---|---|
| 725 | | | 714 + 686 B | 856 (M + Li+) |
| 726 | | | 714 + 682 | 840 (M + Li+) |
| 727 | | | 714 + 683 | 840 (M + Li+) |
| 728 | | | 680 + 686 A | 840 (M + Li+) |
| 729 | | | 681 + 686 A | 840 (M + Li+) |

EXAMPLE 730

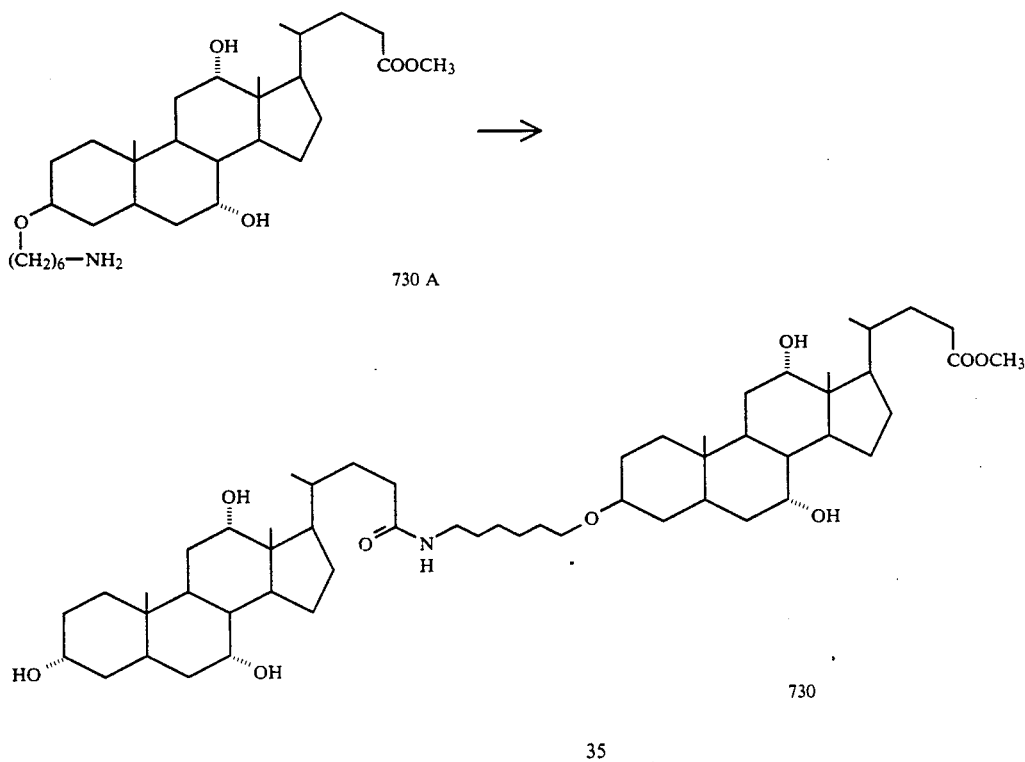

2.1 g (4 mmol) of 730 A are heated to reflux for 8 h in 50 ml of dry THF with 0.6 ml of triethylamine, 1.1 g (4.4 mmol) of EEDQ and 1.64 g (4 mmol) of cholic acid. After reaction is complete, the mixture is concentrated, the residue is taken up with ethyl acetate, the solution is washed with KHSO₄ solution and water and the residue of the organic phase is purified by chromatography. Yield 2.48 g (68%) of 730.

MS (FAB, 3-NBA, LiCl): 919 (M+H⁺)

EXAMPLE 731

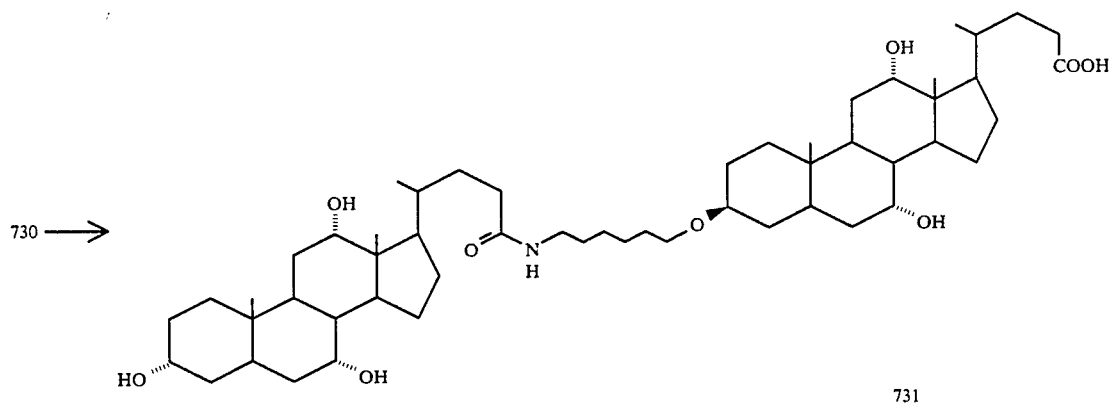

2 g (2.2 mmol) of 730 are hydrolyzed with 3 ml of 2N NaOH in 30 ml of methanol as described under 724. Yield: 1.68 g (85%) of 731.

MS (FAB, 3-NBA, LiCl): 905 (M+Li⁺)

The following example substances (732→734) are prepared analogously to the reaction sequence 730 A→730→731.

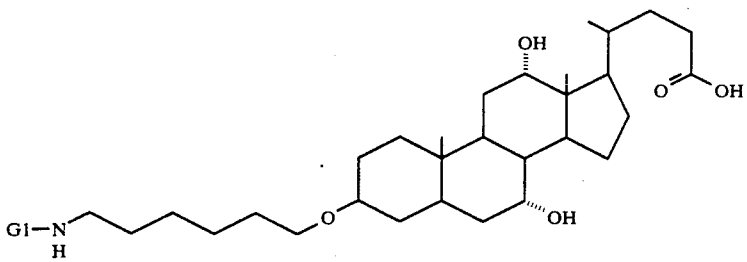

| Ex. | G1 | Starting Materials | MS (FAB, 3-NBA, LiCl) |
|---|---|---|---|
| 732 | (chenodeoxycholic aldehyde structure) | 730 A + Chenodeoxy-cholic acid | 889 (M + Li$^+$) |
| 733 | (ursodeoxycholic aldehyde structure) | 730 A + Ursodeoxy-cholic acid | 889 (M + Li$^+$) |
| 734 | (3β-OH-cholic aldehyde structure) | 730 A + 3β-OH-cholic acid | 905 (M + Li$^+$) |

EXAMPLE 735

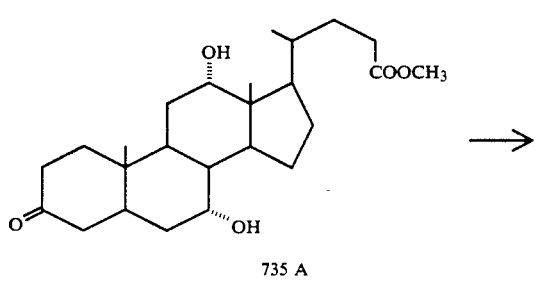

735 A

→

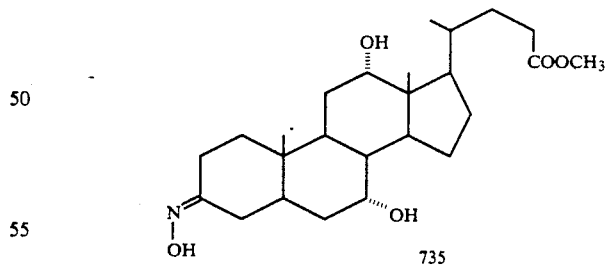

735

A solution of 2.33 g of hydroxylamine hydrochloride and 4.57 g of sodium acetate in 10 ml of water is added to 3.1 g (7.4 mmol) of 735 A in 30 ml of isopropanol under reflux and the mixture is heated to reflux for 4 h. After reaction is complete, water is added, isopropanol is partially removed in vacuo and the mixture is extracted by shaking with plenty of dichloromethane. The residue of the organic phase is purified by chromatography. Yield: 2.7 g (84%) of 735.

MS (FAB, 3-NBA, LiCl) 442 (M+Li$^+$), 436 (M+H$^+$).

EXAMPLE 736

736 ⟶ 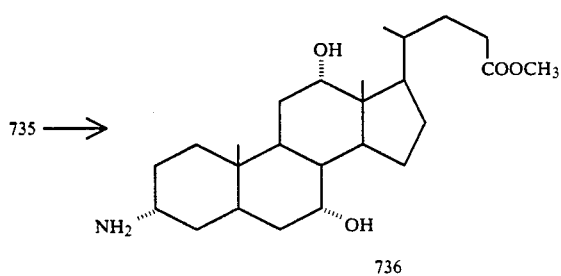

735 ⟶ 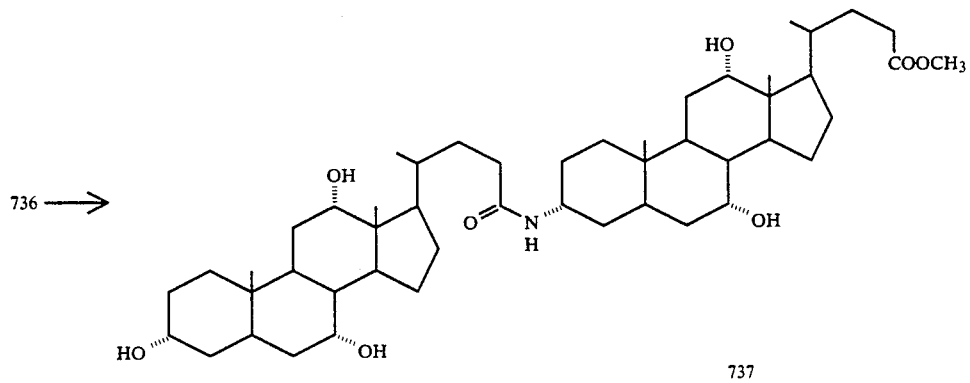

2 g (4.6 mmol) of 735 are hydrogenated for 24 h at 20 bar of H₂ and at room temperature in 50 ml of methanol using 200 mg of 10% palladium/carbon. The catalyst is removed, the mixture is concentrated and the residue is purified by chromatography. Yield 1.56 g (80%) of 736.

MS (FAB, 3-NBA, LiCl): 428 (M+Li⁺), 422 (M+H⁺). According to TLC (SO₂; dichloromethane/methanol/conc. NH₃ solution=100:15:5), 736 is not identical to the 3β-isomeric amine.

EXAMPLE 737

737 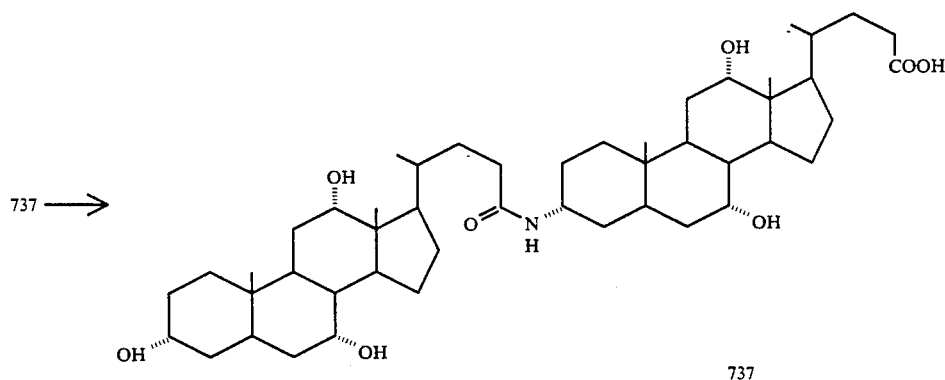

842 mg (2 mmol) of 736 are heated to reflux for 6 h in 50 ml of dry THF with 0.15 ml of triethylamine, 2.2 mmol of EEDQ and 820 mg (2 mmol) of cholic acid. The mixture is concentrated, the residue is taken up with ethyl acetate, the solution is extracted by shaking with KHSO₄ solution and water and the residue of the organic phase is purified by chromatography. Yield 926 mg (57%).

MS (FAB, 3-NBA, LiCl): 819 (M+Li⁺)

EXAMPLE 738

737 ⟶

200 mg (0.25 mmol) of 737 are hydrolyzed with 1.5 ml of half-concentrated NaOH in 15 ml of methanol as described under 724. Yield: 162 mg (82%) of 738.

MS (FAB, 3-NBA,): 798.6 (M+H⁺)

The following example substances are prepared analogously to the reaction sequence 735 A →735→736→737→738.

| Ex. | G1 | G2 | Starting materials | MS(FAB, 3-NBA) |
|---|---|---|---|---|
| | | G1◀NH┈┈G2 | | |
| 739 | | | 736 + Chenodeoxy-cholic acid | 783 (M + H⁺) |
| 740 | | | 736 + Ursodeoxy-cholic acid | 783 (M + H⁺) |
| 741 | | | 678 A + Cholic acid | 783 (M + H⁺) |
| 742 | | | 679 A + Cholic acid | 783 (M + H⁺) |
EXAMPLE 743
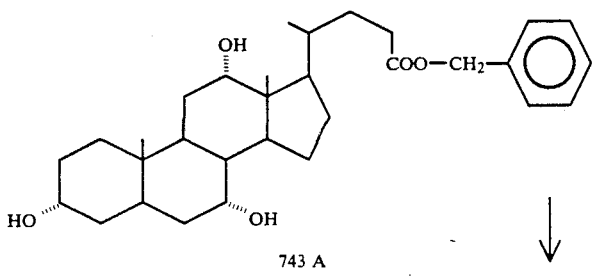
743 A
↓

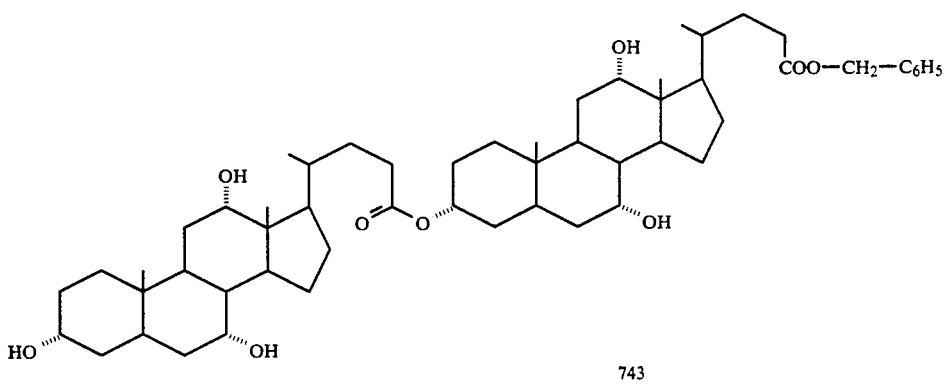

743

1 g of cholic acid (2.45 mmol) is treated with 4 equivalents of trifluoroacetic anhydride at 0° C. in 15 ml of dry THF and the mixture is stirred at room temperature for 2 h. 1.04 g (2.01 mmol) of benzyl cholate in THF are added with ice-cooling and the mixture is stirred overnight at room temperature. About 2.5 ml of concentrated NH$_3$ solution are added with ice-cooling and the mixture is stirred for several hours with TLC checking. After reaction is complete, it is concentrated to a large extent in the cold and the residue is partitioned between plenty of ether and NaHCO$_3$ solution. The organic phase is washed with NaHCO$_3$ solution and water, and concentrated, and the residue is purified by chromatography. Yield 1.14 g (64%) of 743

MS (FAB, 3-NBA, LiCl): 896 (M+H$^+$)

EXAMPLE 744

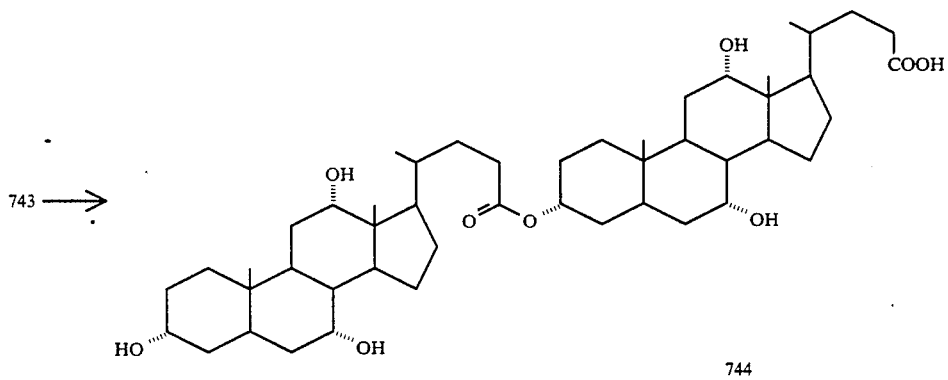

744

1 g (1.12 mmol) of 743 are hydrogenated at room temperature in 10 ml of THF in a duck-shaped shaking apparatus using 200 mg of 10% palladium on carbon. After reaction is complete, the catalyst is removed, the mixture is concentrated and the residue is purified by chromatography.

Yield: 828 mg (92%) of 744.

MS (FAB, 3-NBA, LiCl): 806 (M+Li$^+$)

The following example substances 745–747) were prepared analogously to the reaction sequence 743A→743→744:

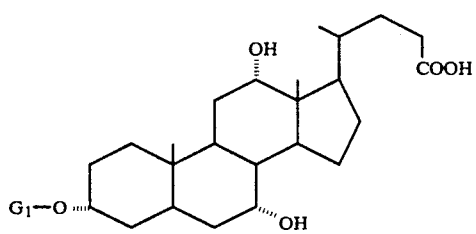
| Ex. | G1 | Starting Materials | MS(FAB, 3-NBA, LiCl) |
|---|---|---|---|
| 745 | | 743 A + Chenodeoxycholic acid | |
| 746 | | 743 A + Lithocolic Acid | |
EXAMPLE 747
MS (FAB, 3-NBA, LiCl): 806 (M+Li+) from 3β-OH-benzyl cholate + cholic acid
EXAMPLE 748
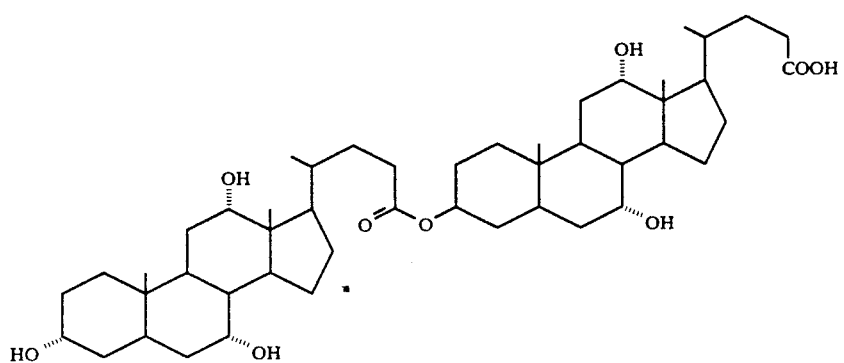

707 → 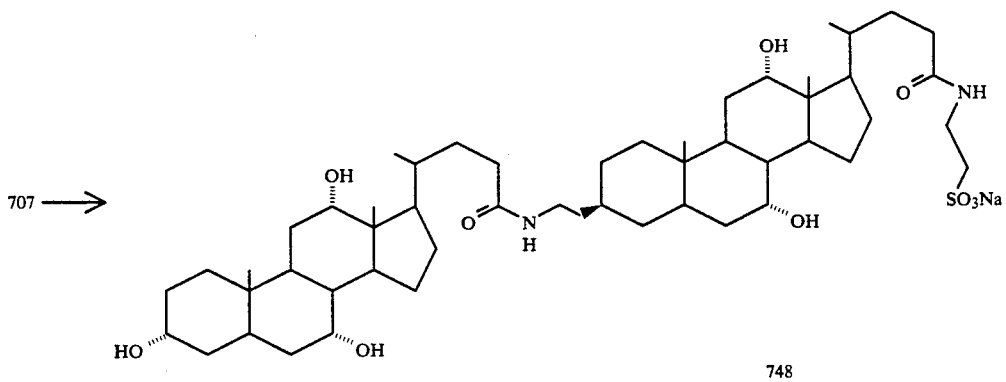

748

826 mg (1 mmol) of 707 and 1.4 mmol of EEDQ were dissolved in 8 ml of dry, purified dimethylformamide and 0.18 ml of triethylamine and 140 mg (1 mmol) of taurine were added. The solution is heated at 90° C. for 15 min. After cooling, 40 ml of dry ether are added. Precipitation of the product is completed by standing overnight in a refrigerator. The solution is decanted, and the precipitate is washed with ether, filtered off with suction and air-dried. The product is dissolved in 5. ml of 0.2N methanolic NaOH, 40 ml of dry ether are added to the solution and it is stirred with ice-cooling for 1 h. The precipitate formed is filtered off with suction and dried in a desiccator. Further purification is carried out by reversed phase chromatography. Yield 806 mg (84%) of 748

MS (FAB, 3-NAB): 956 (M+H$^+$)

The following example substances are prepared analogously to the reaction sequence 707→748.

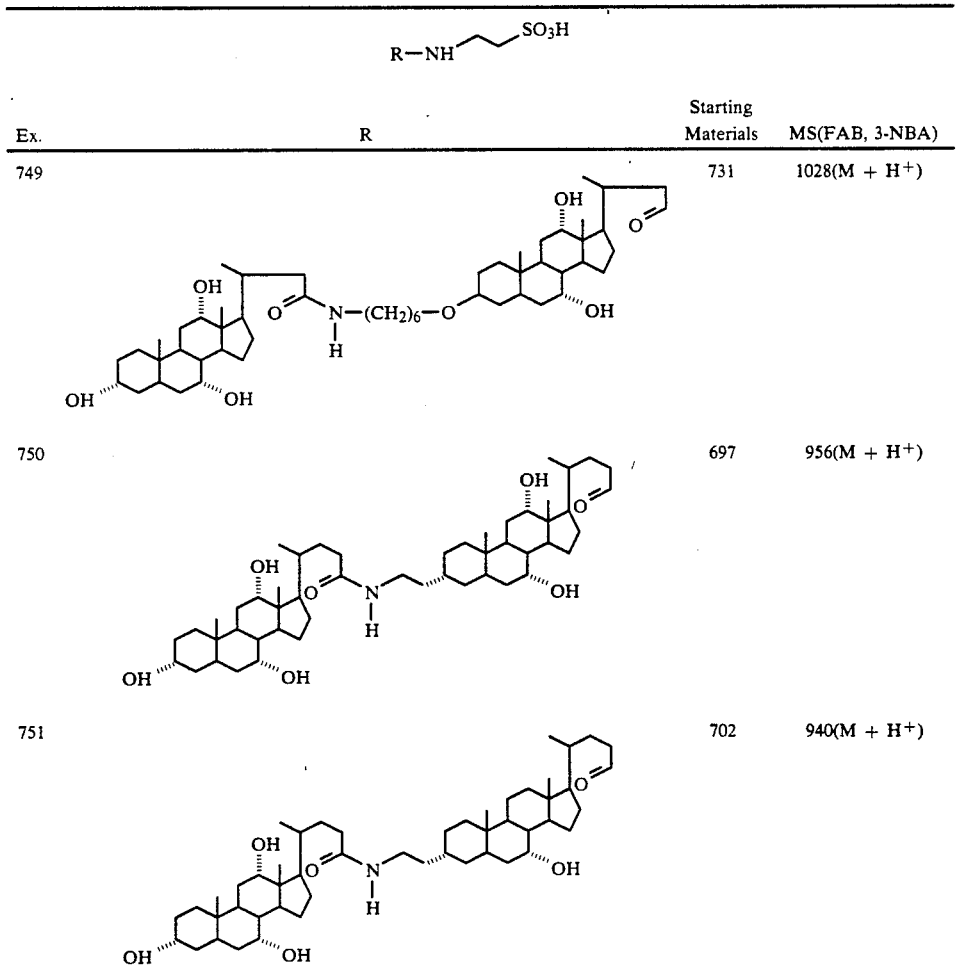

| Ex. | R | Starting Materials | MS(FAB, 3-NBA) |
|---|---|---|---|
| 749 | | 731 | 1028(M + H$^+$) |
| 750 | | 697 | 956(M + H$^+$) |
| 751 | | 702 | 940(M + H$^+$) |

-continued

R—NH—CH$_2$CH$_2$—SO$_3$H

| Ex. | R | Starting Materials | MS(FAB, 3-NBA) |
|---|---|---|---|
| 752 | | 701 | 924(M + H$^+$) |
| 753 | | 700 | 940(M + H$^+$) |
| 754 | | 703 | 940(M + H$^+$) |
| 755 | | 708 | 940(M + H$^+$) |

We claim:

1. A dimeric bile acid derivative of formula (I)

$$G1-X-G2 \quad (I)$$

wherein G1 is a compound of formula (II)

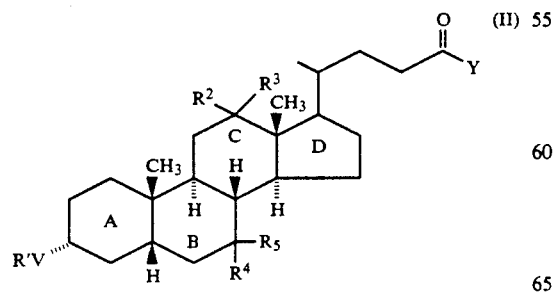

(II)

in which
V is O, NH or CH$_2$

Y is a free valency for bonding the group X of —OL, —NHL, —NL$_2$, an amino acid or aminosulfonic acid bonded via the amino group and their (C$_1$-C$_4$) alkyl esters and alkali metal and alkaline earth metal salts, —O—M, where M is a cation selected from an alkali metal ion, an alkaline earth metal ion or a quarternary ammonium ion, and in which L is H, a saturated or unsaturated alkyl radical having 1-10 carbon atoms, which is branched or unbranched, a cycloalkyl radical having 3-8 carbon atoms, a phenyl radical which is unsubstituted or monosubstituted to trisubstituted by F, Cl, Br, (C$_1$-C$_4$)-alkyl or (C$_{1-4}$)-alkoxy, a benzyl radical which is unsubstituted or monosubstituted to trisubstituted by F, Cl, Br, (C$_1$-C$_4$)-alkyl or (C$_1$-C$_4$)-alkoxy, is methyl, isopropyl, isobutyl, 2-butyl, benzyl, 4-hydroxybenzyl, hydroxymethyl, 1-hydroxyethyl, H$_3$CSCH$_2$CH$_2$—, HO$_2$CCH$_2$— or HO$_2$CCH$_2$CH$_2$—, $R^1$ is a free valency for bonding the group X or H, a saturated or unsaturated alkyl radical having 1–10 carbon atoms, which is branched or unbranched, a cycloalkyl radical having 3–8 carbon atoms, a phenyl radical which is unsubstituted or monosubstituted to trisubstituted by F, Cl, Br, ($C_1$-$C_4$)-alkyl or ($C_1$-$C_4$)-alkoxy, $-N^+H_3$, $-OPO_3^-$, a benzyl radical which is unsubstituted in the ring or monosubstituted to trisubstituted by F, Cl, Br, ($C_1$-$C_4$)-alkyl, ($C_1$-$C_4$)-alkoxy, $-N^+H_3$, $-OPO_3^-$ or phenyl, which can in turn be monosubstituted to trisubstituted by F, Cl, Br, ($C_1$-$C_4$)-alkyl or ($C_1$-$C_4$)-alkoxy, $-N^+H_3$, $-OPO_3^-$, a biphenylmethyl radical which is unsubstituted or monosubstituted to trisubstituted by F, Cl, Br, ($C_1$-$C_4$)-alkyl or ($C_1$-$C_4$)-alkoxy, $-N^+H_3$, $-OPO_3^-$, a triphenylmethylradical which is unsubstituted or monosubstituted to trisubstituted by F, Cl, Br, ($C_1$-$C_4$)-alkyl or ($C_1$-$C_4$)-alkoxy, $-N^+H_3$, $-OPO_3^-$, a 1- or 2-naphthylmethyl radical which is unsubstituted or monosubstituted to trisubstituted by F, Cl, Br, ($C_1$-$C_4$)-alkyl or ($C_1$-$C_4$)-alkoxy, $-N^+H_3$, $-OPO_3^-$, a 9-fluorenyl radical which is unsubstituted or monosubstituted to trisubstituted by F, Cl, Br, ($C_1$-$C_4$)-alkyl or ($C_1$-$C_4$)-alkoxy, $-N^+H_3$, $-OPO_3^-$
a 2-, 3- or 4-pyridyl radical, a radical

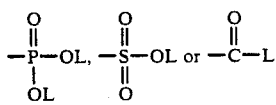

where L has the above-mentioned meaning, $R^2$ to $R^5$, where $R^2$ and $R^3$ or $R^4$ and $R^5$ in each case together are the oxygen of a carbonyl group, or individually and in each case independently of one another are H, OT, $-ST$, $-NHT$, $O-\overset{O}{\underset{\|}{C}}-T$, $-S-\overset{O}{\underset{\|}{C}}-T$,

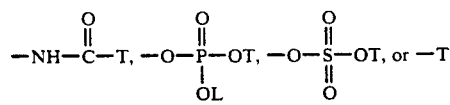

where L has the above mentioned meaning and T has the meaning of L or a free valency for bonding the group X,
with the restriction that altogether only one free valency for bonding the group X starts from G1,
X is a single bond or a group of formula III

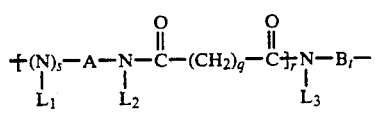

where
A is an alkylene chain which is branched or unbranched, saturated or unsaturated and can be optionally interrupted in the chain by $-O-$, $-S-$ or arylene, where the linkage

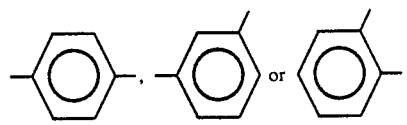

takes place and the chain contains altogether 2 to 12 chain members p;
B is an alkylene chain which is branched or unbranched, saturated or unsaturated and can be optionally interrupted in the chain by $-O-$, $-S-$ or arylene, where the linkage

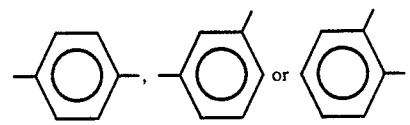

takes place and the chain contains altogether 2 to 18 chain members n,
$L_1$, $L_2$ and $L_3$ are identical or different and have the meaning of L, and
q is 0–5,
r is 0 or 1 and
s is 0 or 1,
t is 0 or 1,
G2 is a compound of formula (IV)

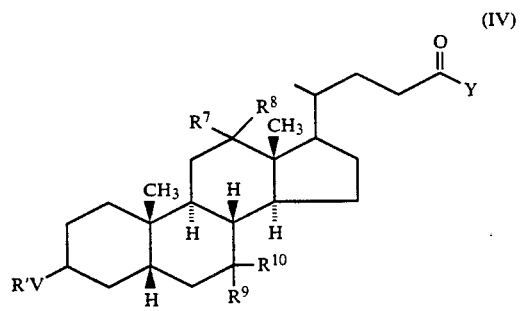

in which V, Y and $R^1$ have the meaning indicated under G1 and $R^7$ to $R^{10}$, where $R^7$ and $R^8$ or $R^9$ and $R^{10}$ in each case are the oxygen of a carbonyl group or individually and in each case independently of one another are H, OT, $-ST$, $-NHT$

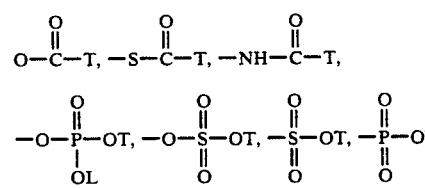

or $-T$ where L and T have the meaning indicated under G1, likewise with the restriction that altogether only one free valency for bonding the group X starts from G2 derivative is not and wherein the linkage of the radicals G1 and G2 is unsymmetrical.

2. A derivative as claimed in claim 1, wherein Y is

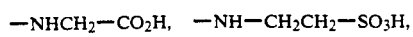

-continued

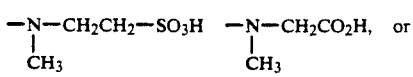

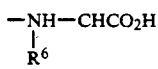

3. A derivative as claimed in claim 1, wherein A is phenylene.

4. A derivative as claimed in claim 1, wherein B is phenylene.

5. A method of reducing cholesterol comprising administering an effective amount of the derivative as claimed in claim 1.

6. A pharmaceutical preparation for reducing cholesterol comprising the derivative as claimed in claim 1 and a pharmaceutically acceptable carrier.

7. A compound as claimed in claim 1, wherein the linkage of the radical G1 takes place through C24 (ring D) via X to one of the positions C3 (ring A), C7 (ring B) or C12 (ring C) of the radical G2.

8. A dimeric bile acid derivative according to claim 1 wherein the alkylene chain of A contains altogether 2 to 6 chain members p.

9. A dimeric bile acid derivative according to claim 1 wherein the alkylene chain of B contains altogether 2 to 12 chain members n.

* * * * *

UNITED STATES PATENT AND TRADEMARK OFFICE
CERTIFICATE OF CORRECTION

PATENT NO. : 5,250,524
DATED : October 05, 1993
INVENTOR(S) : Werner KRAMER et al.

It is certified that error appears in the above-indentified patent and that said Letters Patent is hereby corrected as shown below:

In claim 1, at the bottom of column 257, in Formula (II), change "R'V" to --$R^1V$--.

Claim 1, column 258, line 65, change "alkoxy, is methyl, isopropyl, isobutyl, 2-butyl, ben-" to --alkoxy, $R^5$ is methyl, isopropyl, isobutyl, 2-butyl, ben---.

Claim 1, column 259, lines 17-18, change "triphenylmethylradical" to --triphenylmethyl radical--.

Claim 1, column 260, line 63, delete "derivative is not".

Signed and Sealed this

Thirtieth Day of August, 1994

Attest:

Attesting Officer

BRUCE LEHMAN

Commissioner of Patents and Trademarks